(12) United States Patent
Wang et al.

(10) Patent No.: US 12,398,132 B2
(45) Date of Patent: Aug. 26, 2025

(54) DERIVATIVES OF 4-(IMIDAZO[1,2-A]PYRIDIN-3-YL)-N-(PYRIDINYL)PYRIMIDIN-2-AMINE AS THERAPEUTIC AGENTS

(71) Applicant: AUCENTRA THERAPEUTICS PTY LTD, Dulwich (AU)

(72) Inventors: Shudong Wang, Adelaide (AU); Mingfeng Yu, Marden (AU); Yi Long, Campbelltown (AU)

(73) Assignee: Aucentra Therapeutics Pty Ltd, Dulwich (AU)

( * ) Notice: Subject to any disclaimer, the term of this patent is extended or adjusted under 35 U.S.C. 154(b) by 821 days.

(21) Appl. No.: 17/625,820

(22) PCT Filed: Jul. 10, 2020

(86) PCT No.: PCT/AU2020/000065
§ 371 (c)(1),
(2) Date: Jan. 10, 2022

(87) PCT Pub. No.: WO2021/003517
PCT Pub. Date: Jan. 14, 2021

(65) Prior Publication Data
US 2022/0259203 A1    Aug. 18, 2022

(30) Foreign Application Priority Data
Jul. 10, 2019   (AU) ............... 2019902448

(51) Int. Cl.
| | | |
|---|---|---|
| *C07D 471/04* | (2006.01) | |
| *A61P 35/00* | (2006.01) | |
| *A61P 35/02* | (2006.01) | |
| *C07D 519/00* | (2006.01) | |

(52) U.S. Cl.
CPC ............ *C07D 471/04* (2013.01); *A61P 35/02* (2018.01); *C07D 519/00* (2013.01)

(58) Field of Classification Search
CPC ...... C07D 471/04; C07D 519/00; A61P 35/02
See application file for complete search history.

(56) References Cited

U.S. PATENT DOCUMENTS

| | | | | |
|---|---|---|---|---|
| 2018/0000819 A1* | 1/2018 | Wu | ............. | A61K 31/5386 |
| 2019/0071427 A1* | 3/2019 | Zheng | ............. | A61K 31/506 |

FOREIGN PATENT DOCUMENTS

| | | | | |
|---|---|---|---|---|
| WO | 2006095159 A1 | 9/2006 | | |
| WO | 2010/009155 | 1/2010 | | |
| WO | WO-2012123470 A1 * | 9/2012 | ......... | A61K 31/4985 |
| WO | 2017/020065 | 2/2017 | | |
| WO | 2018/141002 | 8/2018 | | |

OTHER PUBLICATIONS

Britannica, The Editors of Encyclopaedia. "pharmaceutical". Encyclopedia Britannica, Oct. 30, 2024, Accessed Nov. 18, 2024 (Year: 2024).*
Cicenas, J., & Simkus, J., 2024, Cancers, 16(8), 1555 (Year: 2024).*
International Search Report and Written Opinion dated Aug. 6, 2020, from International Application No. PCT/AU2020/000065, 9 pages.
Extended European Search Report issued on Nov. 28, 2022 in European Patent Application No. 20836848.0.

* cited by examiner

*Primary Examiner* — Clinton A Brooks
*Assistant Examiner* — Kendall Nicole Heitmeier
(74) *Attorney, Agent, or Firm* — Meunier Carlin & Curfman LLC

(57) ABSTRACT

A novel class of heteroaryl compounds for use in the prevention and/or treatment of proliferative diseases and conditions including cancers. The compounds are considered to be capable of inhibiting cell proliferation by inhibiting the activity of FLT3 and its mutant forms and/or other protein kinases such as CDKs. The compounds have the general structure I:

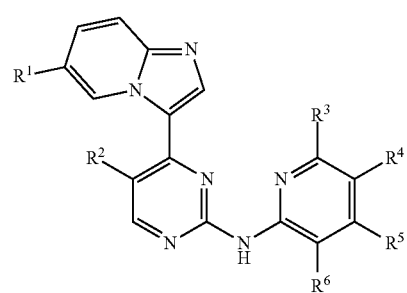

15 Claims, No Drawings

DERIVATIVES OF 4-(IMIDAZO[1,2-A] PYRIDIN-3-YL)-N-(PYRIDINYL)PYRIMIDIN-2-AMINE AS THERAPEUTIC AGENTS

TECHNICAL FIELD

The present disclosure relates to a novel class of inhibitors of protein kinases useful in the treatment of proliferative cell diseases and conditions including cancers.

PRIORITY DOCUMENT

The present application claims priority from Australian Provisional Patent Application No 2019902448 titled "Inhibitors of protein kinases" filed on 10 Jul. 2019, the content of which is hereby incorporated by reference in its entirety.

BACKGROUND

There is an ongoing need to identify and develop new compounds for treating proliferative diseases and conditions including cancers. Among the numerous "targets" for potential anti-proliferative compounds under investigation are the group of enzymes known as protein kinases.

FMS-like tyrosine kinase 3 (FLT3), also known as CD135 antigen and foetal liver kinase-2 (Flk2), is expressed on the surface of many haematopoietic cells and signalling of FLT3 is known to play an important role in the normal development of these cells. The expression or over-expression of FLT3 or its mutations thereof has been associated with certain cancers, particularly blood cancers (ie haematological malignancies). For example, high levels of FLT3 have been found in the blast cells of some patients with acute myeloid leukaemia (AML) (Zheng R et al., *Blood* 103(1): 267-274, 2004), and aberrant FLT3 expression has also been found in acute lymphocytic leukemia (ALL) and chronic lymphocytic leukemia (CLL) (Rosnet O et al., *Leukemia* 10:238-248, 1996). It has been speculated that aberrant- or over-expression of FLT3 might lead to constitutive dimerisation and activation of the receptor (Brasel K et al., *Leukemia* 9:1212-1218, 1995). Moreover, a number of FLT3 "activating" mutations have been identified, most notably the FLT3-ITD mutation comprising an internal tandem duplication (Nakao M et al., *Leukemia* 10:1911-1918, 1996) and known to be associated with very poor prognosis in patients with AML (Kottaridis P D et al., *Blood* 98(6):1752-1759, 2001).

A number of FLT3 inhibitor compounds have been or are under investigation for the treatment of haematological malignancies such as AML and other FLT3-activated cancers. Gilteritinib was the first ever inhibitor drug specifically approved by the US Food and Drug Administration (FDA) for treating AML patients with relapsed or refractory/mutated FLT3, particularly FLT3-ITD or FLT3-TKD (mutation in the tyrosine kinase domain) AML.

Cyclin-dependent kinases (CDKs) are another type of protein kinases. They are known to be associated with various cyclin subunits, playing pivotal roles in the regulation of a variety of important regulatory pathways in cells, including cell-cycle control, apoptosis, neuronal physiology, differentiation and transcription. There are more than 20 CDKs which may be classified into two major groups, reflecting their functions; namely, the cell cycle regulator CDKs and the transcription regulator CDKs. The class of the cell cycle regulator CDKs includes CDK1, CDK2, CDK3, CDK4 and CDK6, and they function with their cyclin partners (eg cyclin A, B, D1, D2, D3, E and F) to regulate promotion of the cell cycle. The class of the transcription regulator CDKs includes CDK7, CDK8, CDK9 and CDK11, which work together with cyclin C, H, K, L1, L2, T1 and T2 and tend to play roles in transcriptional regulation. Given the functions of these two CDK classes, it is perhaps not surprising that CDKs have been implicated in cell proliferation diseases and conditions, particularly cancer. Cell proliferation is a result of the direct or indirect deregulation of the cell division cycle and the CDKs play a critical role in the regulation of the various phases of this cycle. Therefore, inhibitors of CDKs and their associated cyclins are considered to be useful targets for cancer therapy.

Certain pyrimidine-based compounds have been previously investigated for use in treating proliferative disorders and conditions including cancers, for example, 4-thiazol-2-pyridinylamino-pyrimidines and 5-substituted-4-thiazol-pyrimidines (see International patent publications WO 2005/012298 and WO2013/156780, respectively). These compounds inhibit multiple protein kinases, particularly CDKs, including CDK1/cyclin B, CDK2/cyclin E, CDK2/cyclin A, CDK4/cyclin D1, CDK6/cyclin D3, CDK7/cyclin H and CDK9/cyclin TL.

The present applicant has now identified a new class of heteroaryl compounds for use in the prevention and/or treatment of proliferative diseases and conditions including cancers. While not wishing to be bound by theory, it is considered that these novel compounds are capable of inhibiting cell proliferation by inhibiting the activity of FLT3 and its mutant forms and/or other protein kinases such as CDKs.

SUMMARY

According to a first aspect, the present disclosure provides a compound of formula I:

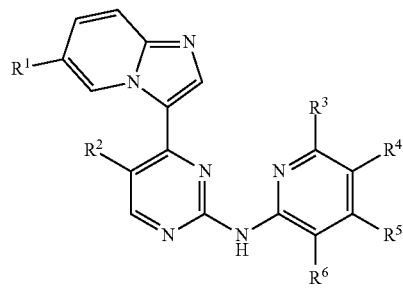

wherein:
$R^1$, $R^2$, $R^3$, $R^4$, $R^5$ and $R^6$ are each independently selected from the group consisting of H, alkyl, alkyl-$R^7$, aryl, aryl-$R^7$, aralkyl, aralkyl-$R^7$, alicyclic, heteroaryl, heterocyclic, halogen, $NO_2$, CN, $CF_3$, OH, O-alkyl, COR, $COOR^7$, O-aryl, O—$R^7$, $NH_2$, NH-alkyl, NH-aryl, N-(alkyl)$_2$, N-(aryl)$_2$, N-(alkyl)(aryl), NH—$R^7$, NH-alkyl-N(alkyl)$_2$, N—($R^7$)($R^8$), N-(alkyl)($R^7$), N-(aryl)($R^7$), COOH, $CONH_2$, CONH-alkyl, CONH-aryl, CON-(alkyl)($R^7$), CON(aryl)($R^7$), CONH—$R^7$, CON—($R^7$)($R^8$), SH-alkyl, $SO_3H$, $SO_2$-alkyl, $SO_2$-alkyl-$R^7$, $SO_2$-aryl, $SO_2$-aryl-$R^7$, $SO_2NH_2$, $SO_2NH$—$R^7$, $SO_2N$—($R^7$)($R^8$), CO-alkyl, CO-alkyl-$R^7$, CO-aryl, CO-aryl-$R^7$ and $R^9$, wherein said alkyl, aryl, aralkyl, alicyclic, heteroaryl and heterocyclic groups may be optionally substituted with one or more groups selected from halogen, CN, OH, alkyl (eg $C_{1-6}$ alkyl), O—$C_{1-6}$ alkyl (eg O-methyl), amino (eg $NH_2$), COOH, $CONH_2$, $CF_3CH(F)_2$ or a heterocyclic group optionally substituted with $C_{1-6}$ alkyl, $CH(F)_2$, COO—$C_{1-6}$ alkyl (eg COO—$C(CH_3)_3$) or phenylsulfonyl; and $R^7$, $R^8$ and $R^9$ are independently selected from water solubilising groups;

or a pharmaceutically acceptable salt, solvate or prodrug thereof.

In a second aspect, the present disclosure provides the use of a compound as defined in the first aspect or a pharmaceutically acceptable salt, solvate or prodrug thereof, for treating cancer or another proliferative disorder or condition.

In a third aspect, the present disclosure provides a method of treating cancer or another proliferative disorder or condition in a subject, the method comprising administering to said subject a therapeutically effective amount of a compound as defined in the first aspect or a pharmaceutically acceptable salt, solvate or prodrug thereof, optionally in combination with a pharmaceutically acceptable carrier, diluent and/or excipient.

In a fourth aspect, the present disclosure provides the use of a compound as defined in the first aspect, or a pharmaceutically acceptable salt, solvate or prodrug thereof, in the manufacture of a medicament for treating cancer or another proliferative cell disease or condition.

In a fifth aspect, the present disclosure provides a pharmaceutical composition or medicament comprising a compound as defined in the first aspect, or a pharmaceutically acceptable salt, solvate or prodrug thereof, and a pharmaceutically acceptable carrier, diluent and/or excipient.

In a sixth aspect, the present disclosure provides a method for modulating protein kinase activity in a cell, comprising introducing to or contacting said cell with an effective amount of a compound as defined in the first aspect or a pharmaceutically acceptable salt, solvate or prodrug thereof.

DETAILED DESCRIPTION

The present applicant has now identified a new class of pyrimidin-2-amine derivatives, particularly derivatives of 4-(imidazo[1,2-a]pyridin-3-yl)-N-(pyridinyl)pyrimidin-2-amine, suitable for use in the prevention and/or treatment of proliferative disorders and conditions including cancers, which possess desirable biological activity (eg the compounds may inhibit cell proliferation and cause cancer cell apoptosis by inhibiting the activity of cell cycle and transcriptional CDKs, and other protein kinases such as FLT3).

According to a first aspect, the present disclosure provides a compound of formula I shown below:

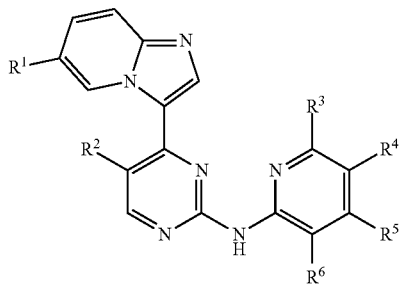

I wherein:

$R^1$, $R^2$, $R^3$, $R^4$, $R^5$ and $R^6$ are each independently selected from the group consisting of H, alkyl, alkyl-$R^7$, aryl, aryl-$R^7$, aralkyl, aralkyl-$R^7$, alicyclic, heteroaryl, heterocyclic, halogen, $NO_2$, CN, $CF_3$, OH, O-alkyl, $COR^7$, $COOR^7$, O-aryl, O—$R^7$, $NH_2$, NH-alkyl, NH-aryl, N-(alkyl)$_2$, N-(aryl)$_2$, N-(alkyl)(aryl), NH—$R^7$, NH-alkyl-N(alkyl)$_2$, N—($R^7$)($R^8$), N-(alkyl)($R^7$), N-(aryl)($R^7$), COOH, $CONH_2$, CONH-alkyl, CONH-aryl, CON-(alkyl)($R^7$), CON (aryl)($R^7$), CONH—$R^7$, CON—($R^7$)($R^8$), SH-alkyl, $SO_3H$, $SO_2$-alkyl, $SO_2$-alkyl-$R^7$, $SO_2$-aryl, $SO_2$-aryl-$R^7$, $SO_2NH_2$, $SO_2NH$—$R^7$, $SO_2N$—($R^7$)($R^8$), CO-alkyl, CO-alkyl-$R^7$, CO-aryl, CO-aryl-$R^7$ and $R^9$, wherein said alkyl, aryl, aralkyl, alicyclic, heteroaryl and heterocyclic groups may be optionally substituted with one or more groups selected from halogen, CN, OH, alkyl (eg $C_{1-6}$ alkyl), O—$C_{1-6}$ alkyl (eg O-methyl), amino (eg $NH_2$), COOH, $CONH_2$, $CF_3CH(F)_2$ or a heterocyclic group optionally substituted with $C_{1-6}$ alkyl, $CH(F)_2$, COO— $C_{1-6}$ alkyl (eg COO—$C(CH_3)_3$) or phenylsulfonyl; and $R^7$, $R^8$ and $R^9$ are independently selected from water solubilising groups;

or a pharmaceutically acceptable salt, solvate or prodrug thereof.

In some embodiments, the compounds of formula I may preferably comprise at least one water solubilising group $R^7$, $R^8$ and $R^9$. That is, in such embodiments, the compound is as defined above in the preceding paragraph with the proviso that said compound comprises at least one of said $R^7$, $R^8$ and $R^9$ groups or, more preferably, comprises at least one of said $R^7$ or $R^8$ groups. The present applicant has found that notwithstanding the addition of such solubilising group(s), the compounds possess desirable biological activity (eg by inhibiting the activity of FLT3). The presence of at least one water solubilising group may enhance in vivo absorption and oral bioavailability.

The compounds of formula I have been found to possess anti-proliferative activity and are therefore considered to be of use in the treatment of proliferative cell diseases and conditions such as cancer, leukaemia, lymphoma and other diseases and conditions associated with uncontrolled cell proliferation (or, in other words, requires control of the cell cycle) such as, for example, some cardiovascular diseases or conditions such as restenosis and cardiomyopathy, some auto-immune diseases such as glomerulonephritis and rheumatoid arthritis, dermatological conditions such as psoriasis, and fungal or parasitic disorders. As used herein, an anti-proliferative effect within the scope of the present disclosure may be demonstrated by the ability to inhibit cell proliferation in an in vitro whole cell assay. An example(s) of such an assay, including methods for performance, are described in more detail in the Example 2 provided hereinafter.

The compounds of formula I may inhibit any of the steps or stages in the cell cycle, for example, formation of the nuclear envelope, exit from the quiescent phase of the cell cycle (G0), G1 progression, chromosome decondensation, nuclear envelope breakdown, START, initiation of DNA replication, progression of DNA replication, termination of DNA replication, centrosome duplication, G2 progression, activation of mitotic or meiotic functions, chromosome condensation, centrosome separation, microtubule nucleation, spindle formation and function, interactions with microtubule motor proteins, chromatid separation and segregation, inactivation of mitotic functions, formation of contractile ring, and cytokinesis functions. In particular, the compounds of formula I may influence certain gene functions such as chromatin binding, formation of replication complexes, replication licensing, phosphorylation or other secondary modification activity, proteolytic degradation, microtubule binding, actin binding, septin binding, microtubule organising centre nucleation activity and binding to components of cell cycle signalling pathways.

Thus, in a second aspect, the present disclosure provides the use of a compound as defined in the first aspect or a pharmaceutically acceptable salt, solvate or prodrug thereof, for treating cancer or another proliferative disorder or condition.

In a third aspect, the present disclosure provides a method of treating cancer or another proliferative disorder or condition in a subject, the method comprising administering to said subject a therapeutically effective amount of a compound as defined in the first aspect or a pharmaceutically acceptable salt, solvate or prodrug thereof, optionally in combination with a pharmaceutically acceptable carrier, diluent and/or excipient.

In a fourth aspect, the present disclosure provides the use of a compound as defined in the first aspect, or a pharmaceutically acceptable salt, solvate or prodrug thereof, in the manufacture of a medicament for treating cancer or another proliferative cell disease or condition.

In a fifth aspect, the present disclosure provides a pharmaceutical composition or medicament comprising a compound as defined in the first aspect, or a pharmaceutically acceptable salt, solvate or prodrug thereof, and a pharmaceutically acceptable carrier, diluent and/or excipient.

In a sixth aspect, the present disclosure provides a method for modulating protein kinase activity in a cell, comprising introducing to or contacting said cell with an effective amount of a compound as defined in the first aspect or a pharmaceutically acceptable salt, solvate or prodrug thereof.

Preferably, the method of the sixth aspect modulates the activity of one or more protein kinases selected from FLT3, FLT3-ITD, and one or more types of FLT3 point mutations, and/or other protein kinases such as CDKs.

In this specification, a number of terms are used which are well known to those skilled in the art. Nevertheless, for the purposes of clarity, a number of these terms are hereinafter defined.

As used herein, the term "treating" includes prophylaxis as well as the alleviation of established symptoms of a condition. As such, the act of "treating" a disease or condition therefore includes: (1) preventing or delaying the appearance of clinical symptoms of the disease or condition developing in a subject afflicted with or predisposed to the disease or condition; (2) inhibiting the disease or condition (ie arresting, reducing or delaying the development of the disease or condition or a relapse thereof (in case of a maintenance treatment) or at least one clinical or subclinical symptom thereof; and (3) relieving or attenuating the disease or condition (ie causing regression of the disease or condition or at least one of its clinical or subclinical symptoms).

As used herein, the term "alkyl" includes both straight chain and branched alkyl groups having from 1 to 8 carbon atoms (eg methyl, ethyl, propyl, isopropyl, butyl, isobutyl, tert-butyl, pentyl, hexyl, cyclopropyl, cyclobutyl, cyclopentyl etc).

As used herein, the term "aryl" refers to a substituted (mono- or poly-) or unsubstituted monoaromatic or polyaromatic group, wherein said polyaromatic group may be fused or unfused. The term therefore includes groups having from 6 to 10 carbon atoms (eg phenyl, naphthyl etc). It is also to be understood that the term "aryl" is synonymous with the term "aromatic".

As used herein, the term "aralkyl" is used as a conjunction of the terms alkyl and aryl as defined above.

The term "aliphatic" takes its normal meaning in the art and includes non-aromatic groups such as alkanes, alkenes and alkynes and substituted derivatives thereof.

As used herein, the term "alicyclic" refers to a cyclic aliphatic group.

The term "halogen" refers to fluoro, chloro, bromo and iodo.

As used herein, the term "heterocyclic" refers to a saturated or unsaturated cyclic group comprising one or more heteroatoms (eg N) in the ring.

The term "derivative" as used herein, includes any chemical modification of an entity. Illustrative of such chemical modifications is the replacement of hydrogen by a halogen group, an alkyl group, an acyl group or an amino group.

As used herein, the phrase "manufacture of a medicament" includes the use of one or more of the compounds of formula I directly as the medicament or in any stage of the manufacture of a medicament comprising one or more of the compounds of formula I.

Some of the compounds of formula I may exist as single stereoisomers, racemates, and/or mixtures of enantiomers and/or diastereomers. All such single stereoisomers, racemates and mixtures thereof, are encompassed within the scope of the present disclosure. The isomeric forms such as diastereomers, enantiomers, and geometrical isomers can be separated by physical and/or chemical methods known to those skilled in the art.

The term "prodrug" means a compound that undergoes conversion to a compound of formula I within a biological system, usually by metabolic means (eg by hydrolysis, reduction or oxidation). For example, an ester prodrug of a compound of formula I containing a hydroxyl group may be convertible by hydrolysis in vivo to the compound of formula I. Suitable esters of the compounds of formula I containing a hydroxyl group may be, for example, acetates, citrates, lactates, tartrates, malonates, oxalates, salicylates, propionates, succinates, fumarates, maleates, methylene-bis-P-hydroxynaphthoates, gentisates, isethionates, di-p-toluoyltartrates, methanesulfonates, ethanesulfonates, benzenesulfonates, p-toluenesulfonates, cyclohexylsulfamates and quinates. As another example, an ester prodrug of a compound of formula I containing a carboxy group may be convertible by hydrolysis in vivo to the compound of formula I. Examples of ester prodrugs include those described by Leinweber F J, Drug Metab Rev 18:379-439 (1987). Similarly, an acyl prodrug of a compound of formula I containing an amino group may be convertible by hydrolysis in vivo to the compound of formula I. Examples of prodrugs for these and other functional groups, including amines, are provided in Prodrugs: challenges and rewards, Valentino J Stella (ed), Springer, 2007.

The term "pharmaceutically acceptable salt" as used herein, refers to salts that retain the desired biological activity of the compounds of formula I, and include pharmaceutically acceptable acid addition salts and base addition salts. Suitable pharmaceutically acceptable acid addition salts of the compounds of formula I may be prepared from an inorganic acid or from an organic acid. Examples of such inorganic acids are hydrochloric, sulfuric and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, fumaric, maleic, alkyl sulfonic and arylsulfonic. Additional information on pharmaceutically acceptable salts can be found in Remington's Pharmaceutical Sciences, 19th Edition, Mack Publishing Co., Easton, PA 1995.

In the case of compounds of formula I that are solid, it will be understood by those skilled in the art that the compounds (or pharmaceutically acceptable salts, solvates or prodrugs thereof) may exist in different crystalline or polymorphic forms, all of which are encompassed within the scope of the present disclosure.

The term "therapeutically effective amount" or "effective amount" is an amount sufficient to effect beneficial or desired clinical results. A therapeutically effective amount can be administered in one or more administrations. Typically, a therapeutically effective amount is sufficient for treating a disease or condition or otherwise to palliate, ameliorate, stabilise, reverse, slow or delay the progression of a disease or condition such as, for example, cancer or another proliferative cell disease or condition. By way of example only, a therapeutically effective amount of a compound of formula I, or a pharmaceutically acceptable salt, solvate or prodrug thereof, may comprise between about 0.1 and about 250 mg/kg body weight per day, more preferably between about 0.1 and about 100 mg/kg body weight per day and, still more preferably between about 0.1 and about 25 mg/kg body weight per day. However, notwithstanding the above, it will be understood by those skilled in the art that the therapeutically effective amount may vary and depend upon a variety of factors including the activity of the particular compound (or salt, solvate or prodrug thereof), the metabolic stability and length of action of the particular compound (or salt, solvate or prodrug thereof), the age, body weight, sex, health, route and time of administration, rate of excretion of the particular compound (or salt, solvate or prodrug thereof), and the severity of, for example, the cancer or other proliferative cell disease or condition to be treated.

The compounds of formula I, and pharmaceutically acceptable salts, solvates and prodrugs thereof, are capable of inhibiting protein kinases may show higher selectivity for (ie to inhibit) FLT3 over one or more CDKs. As mentioned above, FLT3 through its role in the normal development of cells, particularly haematopoietic cells, may promote cancer cell proliferation and resistance to apoptosis. As such, the compounds of formula I, and pharmaceutically acceptable salts, solvates and prodrugs thereof, which are believed to inhibit at least FLT3, have utility in both in vitro and in vivo applications (eg in vitro cell-based assays) and as the basis of a therapeutic method of treating cancer or another proliferative disorder or condition in a subject.

The compounds of formula I may bear at least one water solubilising group (eg provided by $R^7$, $R^8$ and/or $R^9$). The term "water solubilising group" will be well understood by those skilled in the art as referring to any polar functional group which either ionises or is capable of forming hydrogen bonds with water molecules to increase the water solubility of the compound (ie relative to the water solubility of the corresponding compound lacking the water solubilising group). Examples of suitable water solubilising groups and methods and considerations for their introduction are described in, for example, Fundamentals of Medicinal Chemistry by Gareth Thomas (publisher: John Wiley & Sons).

Preferably, where present, $R^7$ and $R^8$ are independently selected from water solubilising groups of the group consisting of:

(i) mono-, di- and poly-hydroxylated alicyclic groups, di- or poly-hydroxylated aliphatic or aryl groups, N-, O- and/or S-containing heterocyclic groups substituted with one or more hydroxyl, amino or alkoxy groups, aliphatic and aryl groups comprising one or more carboxamide, sulfoxide, sulfone or sulfonamide groups, and halogenated alkylcarbonyl groups; and (ii) COOH, $SO_3H$, $OSO_3H$, $SONHCH_3$, $SONHCH_2CH_3$, $SO_2CH_3$, $SO_2CH_2CH_3$, $PO_3H_2$ and $OPO_3H_2$.

Preferably, where present, $R^9$ is selected from water solubilising groups of the group consisting of:

(i) mono-, di- and poly-hydroxylated alicyclic groups, di- or poly-hydroxylated aliphatic or aryl groups; N-, O- and/or S-containing heterocyclic groups optionally substituted with one or more hydroxyl, amino or alkoxy groups, $N(alkyl)_2$, NH-alkyl (optionally substituted with one or more hydroxyl or alkoxy group), alkyl-N(alkyl)$_2$, carbonyl, alkoxy, $SO_2$-alkyl, aliphatic (including alkyl), aryl optionally comprising one or more amino, NH-alkyl (optionally substituted with one or more hydroxyl or alkoxy group), carboxamide, sulfoxide, sulfone or sulfonamide groups, heterocyclic optionally comprising one or more alkyl, or NH-heterocyclic group optionally comprising one or more alkyl or carbonyl, and wherein the N-, O- and/or S-containing heterocyclic group may optionally comprise an alkyl bridge (eg a —$CH_2$— or —$CH_2CH_2$— bridge), amine bridge (eg —NH—, —NH—$CH_2$— and —NH—$CH_2CH_2$—), alkoxy bridge (eg —O—$CH_2$— and —O—$CH_2CH_2$—) or ketone bridge (eg a —C(=O)— bridge) to, for example, the carbon atom at position 4/5 of the pyridine ring of the Formula I compound; and halogenated alkylcarbonyl groups;

(ii) COOH, $SO_3H$, $OSO_3H$, $PO_3H_2$ and $OPO_3H_2$;

(iii) $NHCO(CH_2)_m[NHCO(CH_2)_{m'}]_p[NHCO(CH_2)_{m''}]_qA$ and $NHCO(CH_2)_tNH(CH_2)_{t'}A$ wherein p and q are each independently selected from integers 0 or 1, and m, m', m", t and ' are each independently selected from integers 1 to 10, and A is selected from:

(a) alicyclic, aryl and heterocyclic groups comprising one or more O-, S- or N-heteroatoms, which may further comprise an alkyl bridge (eg a —$CH_2$— or —$CH_2CH_2$— bridge), (b) alicyclic groups comprising one or more of —O—, $NH_2$, —NH—, =N—, quaternary amine salt, and amidine, and (c) morpholine, piperazine or 1,4-diazepane groups, each of which may be optionally substituted by one or more substituents selected from $SO_2$-alkyl, alkyl optionally substituted by one or more OH groups, CO-alkyl, aralkyl, COO-alkyl, and an ether group optionally substituted by one or more OH groups;

(iv) $(CH_2)_n$ $NR^{10}COR^{11}$, $(CH_2)_n NR^{10}SO_2R^{11}$ and $SO_2R^{12}$, wherein $R^{10}$ is selected from H and alkyl, $R^{11}$ and $R^{12}$ are each independently selected from alkyl groups optionally comprising one or more heteroatoms and/or optionally substituted with one or more substituents independently selected from OH, $NH_2$, halogen and $NO_2$, and n and n' are each independently selected from integers 0, 1, 2 and 3;

(v) ether and polyether groups optionally substituted with one or more OH groups or one or more A groups, wherein A is as defined above at (iii);

(vi) $(CH_2)_rNH_2$, wherein r is selected from integers 0, 1, 2 and 3;

(vii) $(CH_2)_{r'}OH$, wherein r' is selected from integers 0, 1, 2 and 3;

(viii) $(CH_2)_{n''}NR^{13}COR^{14}$, wherein $R^{13}$ is H or alkyl, n" is selected from integers 0, 1, 2 and 3, and $R^{14}$ is an aryl group optionally substituted with one or more substituents selected from halogen, NO$_2$, OH, alkoxy, NH$_2$, COOH, CONH$_2$ and CF$_3$; and (ix) SO$_2$NR$^{15}$R$^{16}$, wherein R$^{15}$ and R$^{16}$ are each independently selected from H, alkyl and aryl, with the proviso that at least one of R$^{15}$ and R$^{16}$ is other than H, or R$^{15}$ and R$^{16}$ together form a cyclic group optionally comprising one or more heteroatoms selected from N, O and S, and wherein said alkyl, aryl or cyclic group is optionally substituted by one or more substituents selected from halogen, NO$_2$, OH, alkoxy, NH$_2$, COOH, CONH$_2$ and CF$_3$.

In some embodiments, R$^1$ and R$^2$ are each independently selected from the group consisting of H, alkyl, alkyl-R$^7$, aryl, aryl-R$^7$, aralkyl, aralkyl-R$^7$, alicyclic, heteroaryl, heterocyclic, halogen, NO$_2$, CN, CF$_3$, OH, O-alkyl, COR$^7$, COOR$^7$, O-aryl, O—R$^7$, NH$_2$, NH-alkyl, NH-aryl, N-(alkyl)$_2$, N-(aryl)$_2$, N-(alkyl)(aryl), NH—R$^7$, NH-alkyl-N(alkyl)$_2$, N—(R$^7$)(R$^8$), N-(alkyl)(R$^7$), N-(aryl)(R$^7$), COOH, CONH$_2$, CONH-alkyl, CONH-aryl, CON-(alkyl)(R$^7$), CON(aryl)(R$^7$), CONH—R$^7$, CON—(R$^7$)(R$^8$), SH-alkyl, SO$_3$H, SO$_2$-alkyl, SO$_2$-alkyl-R$^7$, SO$_2$-aryl, SO$_2$-aryl-R$^7$, SO$_2$NH$_2$, SO$_2$NH—R$^7$, SO$_2$N—(R$^7$)(R$^8$), CF$_3$, CO-alkyl, CO-alkyl-R$^7$, CO-aryl, CO-aryl-R$^7$ and R$^9$, wherein said alkyl, aryl, aralkyl, alicyclic, heteroaryl and heterocyclic groups may be optionally substituted with one or more groups selected from halogen, CN, OH, C$_{1-6}$ alkyl, O—C$_{1-6}$ alkyl (eg O-methyl), amino (eg NH$_2$), COOH, CONH$_2$, CF$_3$CH(F)$_2$ or a heterocyclic group optionally substituted with C$_{1-6}$ alkyl, CH(F)$_2$, COO—C$_{1-6}$ alkyl (eg COO—C(CH$_3$)$_3$) or phenylsulfonyl; and R$^3$, R$^4$, R$^5$ and R$^6$ are each independently selected from the group consisting of H, alkyl-R$^7$, aryl, aryl-R$^7$, aralkyl, aralkyl-R$^7$, alicyclic, heterocyclic, CF$_3$, COR$^7$, COOR$^7$, O-aryl, O—R$^7$, NH-aryl, N-(aryl)$_2$, N-(alkyl)(aryl), NH—R$^7$, N—(R$^7$)(R$^8$), N-(alkyl)(R$^7$), N-(aryl)(R$^7$), CONH-alkyl, CONH-aryl, CON-(alkyl)(R$^7$), CON(aryl)(R$^7$), CONH—R$^7$, CON—(R$^7$)(R$^8$), SO$_3$H, SO$_2$-alkyl-R$^7$, SO$_2$-aryl, SO$_2$-aryl-R$^7$, SO$_2$NH—R$^7$, SO$_2$N—(R$^7$)(R$^8$), CO-alkyl-R$^7$, CO-aryl, CO-aryl-R$^7$ and R$^9$, wherein said alkyl, aryl, aralkyl, alicyclic and heterocyclic groups may be optionally substituted with one or more groups selected from halogen, CN, OH, O-methyl, NH$_2$, COOH, CONH$_2$ and CF$_3$.

In some embodiments, R$^1$ is H, alkyl (eg a C$_{1-6}$ alkyl or, preferably, a C$_{1-3}$ alkyl such as methyl, ethyl and C(CH$_3$)$_2$), aryl, CN, CF$_3$, NH$_2$, heteroaryl, optionally substituted heterocyclic (eg a saturated or unsaturated 5- or 6-membered cyclic group comprising one or two N, O or S heteroatoms), O-alkyl (eg a O—C$_{1-3}$ alkyl such as O—CH$_3$), NH-alkyl (eg a NH—C$_{1-6}$ alkyl such as NH(C$_5$H$_9$) (ie NH-cyclopentyl) or, preferably, a NH—C$_{1-3}$ alkyl such as NH—CH$_3$), NH-alkyl-N(alkyl)$_2$ (eg a NH-alkyl-(C$_{1-6}$ alkyl)$_2$ such as NH(C$_{1-3}$ alkyl)-N(C$_{1-3}$ alkyl)$_2$), NH-aryl, N-(alkyl)$_2$ such as N(CH$_3$)$_2$, N-(alkyl)(aryl), SH-alkyl (eg a SH—C$_{1-6}$ alkyl or, preferably, a SH—C$_{1-3}$ alkyl such as SHCH$_3$ and SHC(CH$_3$)), halogen (preferably F, Br or Cl) or R$^9$. Where R$^1$ is R$^9$, preferably R$^9$ is a mono-, di- or poly-hydroxylated alicyclic group, or an N-, O- and/or S-containing heterocyclic group substituted with one or more hydroxyl, amino or alkoxy group. Most preferably, R$^1$ is H, C$_{1-3}$ alkyl such as methyl, aryl, CF$_3$, heterocyclic group optionally substituted with C$_{1-6}$ alkyl, O—C$_{1-6}$ alkyl (eg O-methyl), amino (eg NH$_2$), CH(F)$_2$, phenylsulfonyl or piperazine optionally substituted with C$_{1-6}$ alkyl (eg piperazine optionally substituted with a C$_{1-6}$ alkyl, pyridine optionally substituted with a C$_{1-6}$ alkyl, pyrimidine optionally substituted with a C$_{1-6}$ alkyl, O-methyl, NH$_2$ or an optionally substituted piperazine, pyrrole, pyrazole optionally substituted with a C$_{1-6}$ alkyl, CH(F)$_2$ or piperazine optionally substituted with COO—C$_{1-6}$ alkyl (eg COO—C(CH$_3$)$_3$), thiophenyl, furan optionally substituted with a C$_{1-6}$ alkyl, and including bicyclic structures such as benzofuran, benzo-thiophenyl, indole optionally substituted with C$_{1-6}$ alkyl or phenylsulfonyl, and pyrrolopyridine optionally substituted with phenylsulfonyl), O—C$_{1-6}$ alkyl (eg O-methyl), amino (eg NH$_2$), NH-aryl or halogen (preferably F or Br).

In some embodiments, R$^2$ is H, alkyl (eg a C$_{1-6}$ alkyl or, preferably, a C$_{1-3}$ alkyl such as methyl or ethyl), CN or halogen (preferably F).

In some embodiments, at least one of R$^3$, R$^4$, R$^5$ and R$^6$, but preferably R$^4$ or R$^5$, is C$_{1-6}$ alkyl or, preferably, a C$_{1-3}$ alkyl such as methyl, halogen, alkyl-R$^7$ (eg a C$_{1-3}$alkyl-R$^7$) wherein R$^7$ is preferably selected from COOH, SO$_3$H, OSO$_3$H, SONHCH$_3$, SONHCH$_2$CH$_3$, SO$_2$CH$_3$, SO$_2$CH$_2$CH$_3$, PO$_3$H$_2$ and OPO$_3$H$_2$, but more preferably is SONHCH$_3$ or SONHCH$_2$CH$_3$, NH—R$^7$ wherein R$^7$ is preferably selected from COOH, SO$_3$H, OSO$_3$H, SONHCH$_3$, SONHCH$_2$CH$_3$, SO$_2$CH$_3$, SO$_2$CH$_2$CH$_3$, PO$_3$H$_2$ and OPO$_3$H$_2$, but more preferably is SO$_2$CH$_3$ or SO$_2$CH$_2$CH$_3$, or is R$^9$ wherein R$^9$ is preferably an N-, O- and/or S-containing heterocyclic group substituted with one or more hydroxyl, amino or alkoxy (eg —OCH$_3$) group. Preferably, the heteroatom(s) is/are N.

In some embodiments, where R$^3$, R$^5$ and R$^6$ are H, R$^4$ is preferably other than COOH, C(=)NHOH, C(=O)NHO-tetrahydropyran or CONH-aryl substituted with NH$_2$.

In some embodiments, where at least one of R$^3$, R$^4$, R$^5$ and R$^6$ is R$^9$, R$^9$ is preferably selected from the following:

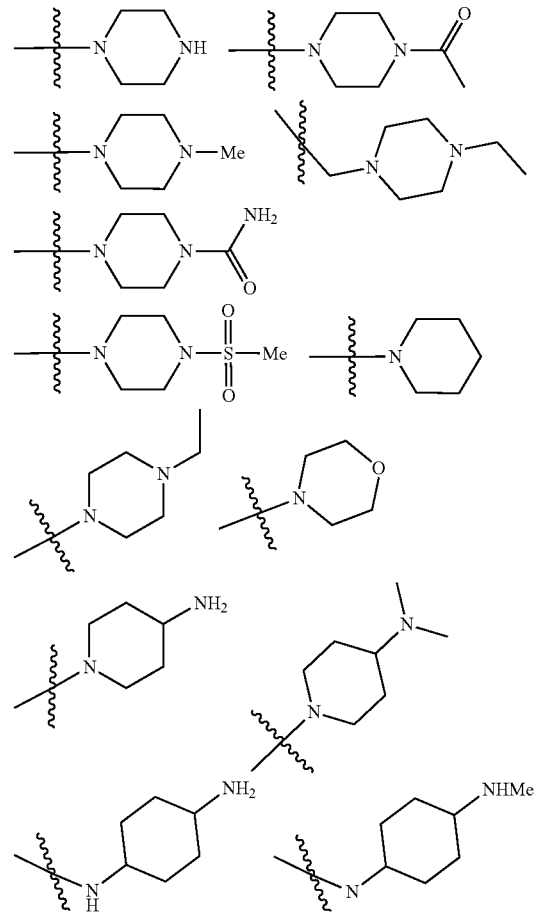

-continued

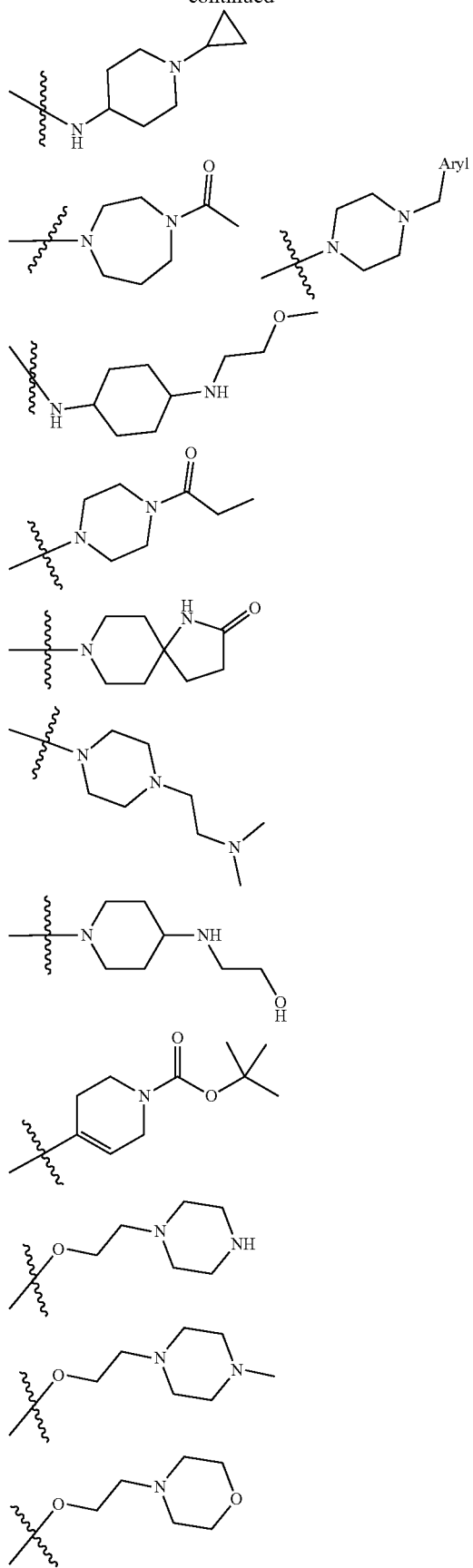

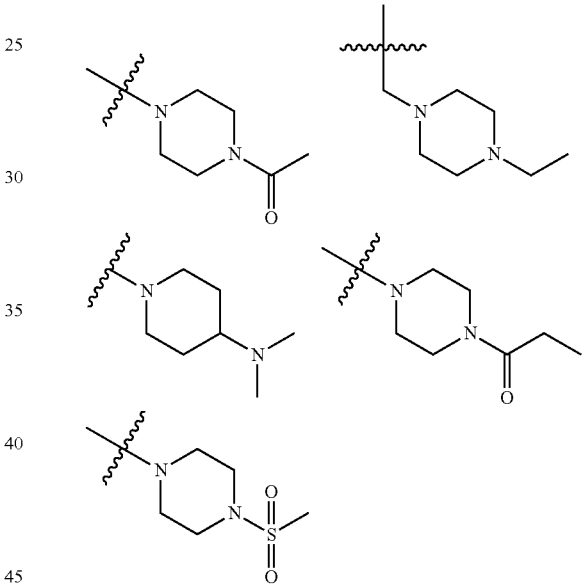

Optionally, the $R^9$ substituents shown in the preceding paragraph may further comprise an alkyl bridge (eg a —$CH_2$— or —$CH_2CH_2$— bridge), amino bridge (eg —NH—), alkoxy bridge (eg —O—$CH_2$—) or ketone bridge (eg a —C(=O)— bridge) to the carbon atom at position 4/5 of the pyridine ring.

Where $R^3$ is $R^9$, $R^4$, $R^5$ and $R^6$ are preferably H. Similarly, where $R^4$ is $R^9$, $R^3$, $R^5$ and $R^6$ are preferably H. Also, where $R^5$ is $R^9$, $R^3$, $R^4$ and $R^6$ are preferably H. And where $R^6$ is $R^9$, $R^3$, $R^4$ and $R^5$ are preferably H.

In some embodiments, $R^3$ and $R^6$ are H.

In some particularly preferred embodiments, $R^3$, $R^5$ and $R^6$ are each H, and $R^4$ is $R^9$, wherein $R^9$ is:

In some other preferred embodiments, the compound is of formula II:

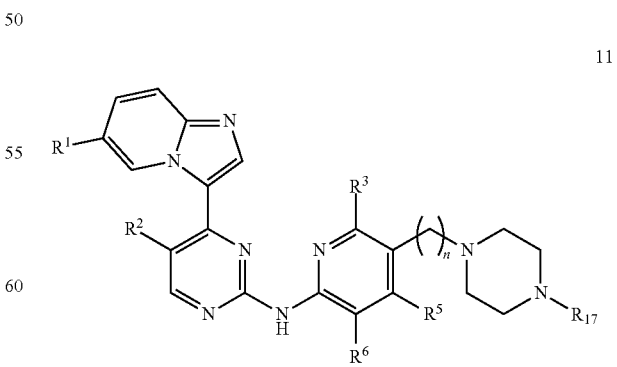

wherein n is 0 or 1, $R^1$, $R^2$, $R^3$, $R^4$, $R^5$ and $R^6$ are as defined above in respect of Formula I; and $R^{17}$ is selected from H, alkyl (eg a $C_{1-6}$ alkyl or, preferably, a $C_{1-3}$ alkyl such as methyl or ethyl), alkoxy (eg —OCH₃ or —OCH₂CH₃), carbonyl (eg a ketone group such as CO—CH₃ or carboxylate such as COO—C(CH₃)₃), methylsulfonyl, NH-alkyl (eg N(CH₃)₂) and carboxamide (eg CONH₂).

In some preferred embodiments, the compound is selected from the group consisting of 1-(4-(6-((4-(imidazo[1,2-a]pyridin-3-yl)pyrimidin-2-yl)amino)pyridin-3-yl)piperazin-1-yl)ethan-1-one;

1-(4-(6-((4-(6-(thiophen-2-yl)imidazo[1,2-a]pyridin-3-yl)pyrimidin-2-yl)amino)pyridin-3-yl)piperazin-1-yl)ethan-1-one;

1-(4-(6-((5-fluoro-4-(6-methylimidazo[1,2-a]pyridin-3-yl)pyrimidin-2-yl)amino)pyridin-3-yl)piperazin-1-yl)ethan-1-one;

N-(5-((4-ethylpiperazin-1-yl)methyl)pyridin-2-yl)-5-fluoro-4-(6-phenylimidazo[1,2-a]pyridin-3-yl)pyrimidin-2-amine;

N-(5-(4-(dimethylamino)piperidin-1-yl)pyridin-2-yl)-5-fluoro-4-(6-phenylimidazo[1,2-a]pyridin-3-yl)pyrimidin-2-amine;

1-(4-(6-((4-(6-chloroimidazo[1,2-a]pyridin-3-yl)pyrimidin-2-yl)amino)pyridin-3-yl)piperazin-1-yl)ethan-1-one;

1-(4-(6-((4-(6-(trifluoromethyl)imidazo[1,2-a]pyridin-3-yl)pyrimidin-2-yl)amino)pyridin-3-yl)piperazin-1-yl)ethan-1-one;

1-(4-(6-((4-(6-methylimidazo[1,2-a]pyridin-3-yl)pyrimidin-2-yl)amino)pyridin-3-yl)piperazin-1-yl)ethan-1-one;

1-(4-(6-((4-(6-phenylimidazo[1,2-a]pyridin-3-yl)pyrimidin-2-yl)amino)pyridin-3-yl)piperazin-1-yl)ethan-1-one;

1-(4-(6-((4-(6-(pyridin-3-yl)imidazo[1,2-a]pyridin-3-yl)pyrimidin-2-yl)amino)pyridin-3-yl)piperazin-1-yl)ethan-1-one;

1-(4-(6-((4-(6-(benzofuran-2-yl)imidazo[1,2-a]pyridin-3-yl)pyrimidin-2-yl)amino)pyridin-3-yl)piperazin-1-yl)ethan-1-one;

1-(4-(6-((4-(6-(benzo[b]thiophen-2-yl)imidazo[1,2-a]pyridin-3-yl)pyrimidin-2-yl)amino)pyridin-3-yl)piperazin-1-yl)ethan-1-one;

1-(4-(6-((4-(6-(1H-pyrrol-3-yl)imidazo[1,2-a]pyridin-3-yl)pyrimidin-2-yl)amino)pyridin-3-yl)piperazin-1-yl)ethan-1-one;

1-(4-(6-((4-(6-(1H-pyrazol-4-yl)imidazo[1,2-a]pyridin-3-yl)pyrimidin-2-yl)amino)pyridin-3-yl)piperazin-1-yl)ethan-1-one;

1-(4-(6-((4-(6-(furan-3-yl)imidazo[1,2-a]pyridin-3-yl)pyrimidin-2-yl)amino)pyridin-3-yl)piperazin-1-yl)ethan-1-one;

1-(4-(6-((4-(6-(thiophen-3-yl)imidazo[1,2-a]pyridin-3-yl)pyrimidin-2-yl)amino)pyridin-3-yl)piperazin-1-yl)ethan-1-one;

1-(4-(6-((4-(6-(1-methyl-1H-pyrazol-4-yl)imidazo[1,2-a]pyridin-3-yl)pyrimidin-2-yl)amino)pyridin-3-yl)piperazin-1-yl)ethan-1-one;

1-(4-(6-((4-(6-(phenylamino)imidazo[1,2-a]pyridin-3-yl)pyrimidin-2-yl)amino)pyridin-3-yl)piperazin-1-yl)ethan-1-one;

1-(4-(6-((4-(6-(benzofuran-3-yl)imidazo[1,2-a]pyridin-3-yl)pyrimidin-2-yl)amino)pyridin-3-yl)piperazin-1-yl)ethan-1-one;

1-(4-(6-((4-(6-(benzo[b]thiophen-3-yl)imidazo[1,2-a]pyridin-3-yl)pyrimidin-2-yl)amino)pyridin-3-yl)piperazin-1-yl)ethan-1-one;

1-(4-(6-((4-(6-(1-methyl-1H-indol-3-yl)imidazo[1,2-a]pyridin-3-yl)pyrimidin-2-yl)amino)pyridin-3-yl)piperazin-1-yl)ethan-1-one;

1-(4-(6-((4-(6-(1H-indol-3-yl)imidazo[1,2-a]pyridin-3-yl)pyrimidin-2-yl)amino)pyridin-3-yl)piperazin-1-yl)ethan-1-one;

1-(4-(6-((4-(6-(1H-pyrrolo[2,3-b]pyridin-3-yl)imidazo[1,2-a]pyridin-3-yl)pyrimidin-2-yl)amino)pyridin-3-yl)piperazin-1-yl)ethan-1-one;

1-(4-(6-((4-(6-iodoimidazo[1,2-a]pyridin-3-yl)pyrimidin-2-yl)amino)pyridin-3-yl)piperazin-1-yl)ethan-1-one;

N-(5-(4-methylpiperazin-1-yl)pyridin-2-yl)-4-(6-phenylimidazo[1,2-a]pyridin-3-yl)pyrimidin-2-amine;

4-(6-bromoimidazo[1,2-a]pyridin-3-yl)-N-(5-(4-(methylsulfonyl)piperazin-1-yl)pyridin-2-yl)pyrimidin-2-amine;

N-(5-(4-(methylsulfonyl)piperazin-1-yl)pyridin-2-yl)-4-(6-phenylimidazo[1,2-a]pyridin-3-yl)pyrimidin-2-amine;

1-(4-(6-((4-(6-(1H-pyrazol-3-yl)imidazo[1,2-a]pyridin-3-yl)pyrimidin-2-yl)amino)pyridin-3-yl)piperazin-1-yl)ethan-1-one;

1-(4-(6-((4-(6-(1-methyl-1H-pyrazol-3-yl)imidazo[1,2-a]pyridin-3-yl)pyrimidin-2-yl)amino)pyridin-3-yl)piperazin-1-yl)ethan-1-one;

1-(4-(6-((4-(6-(1-(difluoromethyl)-1H-pyrazol-4-yl)imidazo[1,2-a]pyridin-3-yl)pyrimidin-2-yl)amino)pyridin-3-yl)piperazin-1-yl)ethan-1-one;

tert-butyl 4-(4-(3-(2-((5-(4-acetylpiperazin-1-yl)pyridin-2-yl)amino)pyrimidin-4-yl)imidazo[1,2-a]pyridin-6-yl)-1H-pyrazol-1-yl)piperidine-1-carboxylate;

1-(4-(6-((4-(6-(5-methylfuran-2-yl)imidazo[1,2-a]pyridin-3-yl)pyrimidin-2-yl)amino)pyridin-3-yl)piperazin-1-yl)ethan-1-one; and 4-(6-(1-methyl-1H-pyrazol-4-yl)imidazo[1,2-a]pyridin-3-yl)-N-(5-(4-methylpiperazin-1-yl)pyridin-2-yl)pyrimidin-2-amine.

In some preferred embodiments, the compounds of the present disclosure exhibit anti-proliferative activity in human cell lines, as measured by a standard cytotoxicity assay. Preferably, the compound exhibits an $IC_{50}$ value of less than 5 µM, even more preferably less than 1 µM as measured by the cell viability assay described in Example 2 hereinafter. More preferably still, the compound exhibits an $IC_{50}$ value of less than 0.5 µM.

In some preferred embodiments, the compounds of the present disclosure inhibit one or more protein kinases, as measured by any standard assay well known to those skilled in the art. Preferably, the compound exhibits an $IC_{50}$ value of less than 1 µM or less than 0.5 µM as measured by the kinase assay described in Example 2 hereinafter, more preferably still less than 0.1 µM.

Particular examples of compounds according to the first aspect are shown in Table 1 below.

TABLE 1

Chemical structure of selected compounds of the present disclosure

| No. | Structure | Name | Mass |
|---|---|---|---|
| 1 | 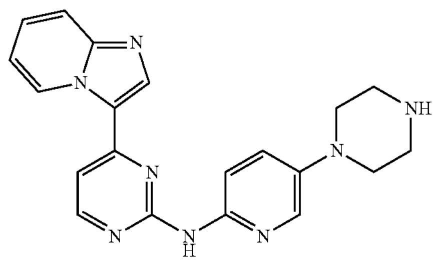 [SMILES: c1ccn2c(-c3ccnc(Nc4ccc(N5CCNCC5)cn4)n3)cnc2c1] | 4-(imidazo[1,2-α]pyridin-3-yl)-N-(5-(piperazin-1-yl)pyridin-2-yl)pyrimidin-2-amine | 372.4 |
| 2 | 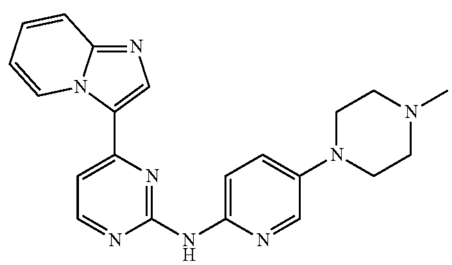 [SMILES: CN1CCN(c2ccc(Nc3nccc(-c4cnc5ccccn45)n3)nc2)CC1] | 4-(imidazo[1,2-α]pyridin-3-yl)-N-(5-(4-methylpiperazin-1-yl)pyridin-2-yl)pyrimidin-2-amine | 386.5 |
| 3 | 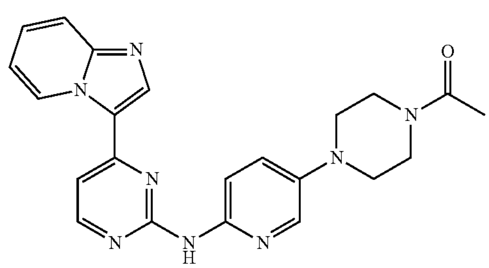 [SMILES: CC(=O)N1CCN(c2ccc(Nc3nccc(-c4cnc5ccccn45)n3)nc2)CC1] | 1-(4-(6((4-(imidazo[1,2-α]pyridin-3-yl)pyrimidin-2-yl)amino)pyridin-3-yl)piperazin-1-yl)ethan-1-one | 414.5 |
| 4 | 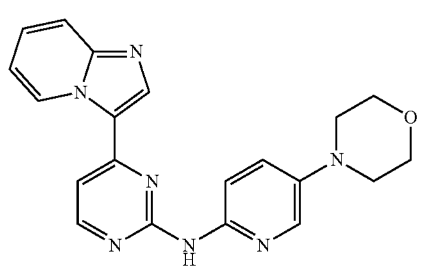 [SMILES: c1ccn2c(-c3ccnc(Nc4ccc(N5CCOCC5)cn4)n3)cnc2c1] | 4-(imidazo[1,2-α]pyridin-3-yl)-N-(5-morpholinopyridin-2-yl)pyrimidin-2-amine | 373.4 |
| 5 | 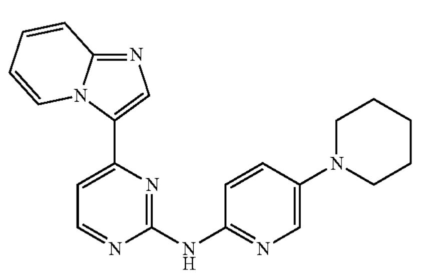 [SMILES: c1ccn2c(-c3ccnc(Nc4ccc(N5CCCCC5)cn4)n3)cnc2c1] | 4-(imidazo[1,2-α]pyridin-3-yl)-N-(5-(p peridin-1-yl)pyridin-2-yl)pyrimidin-2-amine | 371.4 |

TABLE 1-continued

Chemical structure of selected compounds of the present disclosure

| No. | Structure | Name | Mass |
|---|---|---|---|
| 6 | 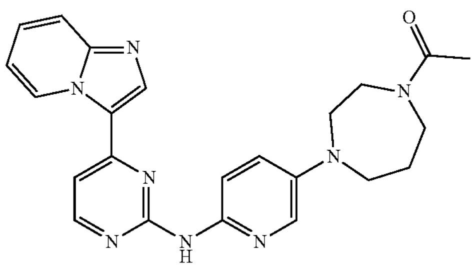 [SMILES: CC(=O)N1CCCN(c2ccc(Nc3nccc(-c4cnc5ccccn45)n3)nc2)CC1] | 1-(4-(6-((4-(imidazo[1,2-α]pyridin-3-yl)pyrimidin-2-yl)amino)pyridin-3-yl)-1,4-diazepan-1-yl)ethan-1-one | 428.5 |
| 7 | 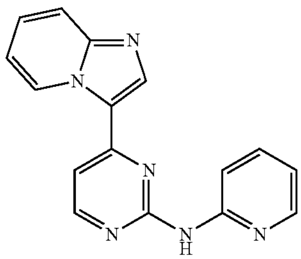 [SMILES: c1ccc(Nc2nccc(-c3cnc4ccccn34)n2)nc1] | 4-(imidazo[1,2-α]pyridin-3-yl)-N-(pyridin-2-yl)pyrimidin-2-amine | 288.3 |
| 8 | 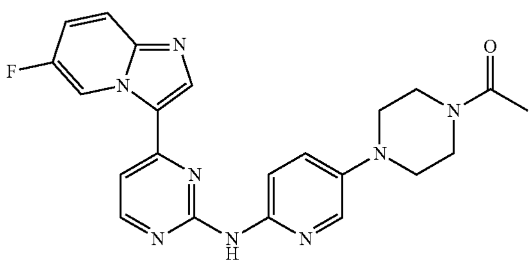 [SMILES: CC(=O)N1CCN(c2ccc(Nc3nccc(-c4cnc5ccc(F)cn45)n3)nc2)CC1] | 1-(4-(6-((4-(6-fluoroimidazo[1,2-α]pyridin-3-yl)pyrimidin-2-yl)amino)pyridin-3-yl)piperazin-1-yl)ethan-1-one | 432.5 |
| 9 | 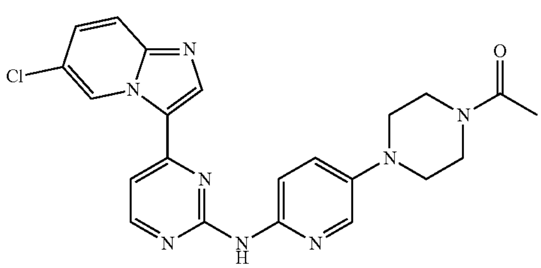 [SMILES: CC(=O)N1CCN(c2ccc(Nc3nccc(-c4cnc5ccc(Cl)cn45)n3)nc2)CC1] | 1-(4-(6-((4-(6-chloroimidazo[1,2-α]pyridin-3-yl)pyrimidin-2-yl)amino)pyridin-3-yl)piperazin-1-yl)ethan-1-one | 448.9 |
| 10 | 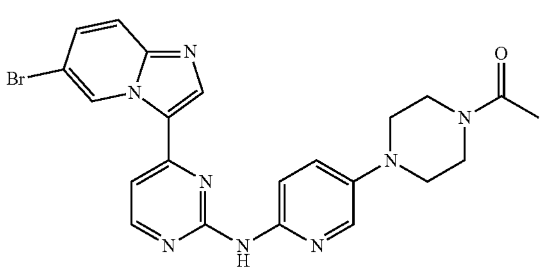 | 1-(4-(6-((4-(6-bromoimidazo[1,2-α]pyridin-3-yl)pyrimidin-2-yl)amino)pyridin-3-yl)piperazin-1-yl)ethan-1-one | 493.4 |

TABLE 1-continued

Chemical structure of selected compounds of the present disclosure

| No. | Structure | Name | Mass |
|-----|-----------|------|------|
| 11 | 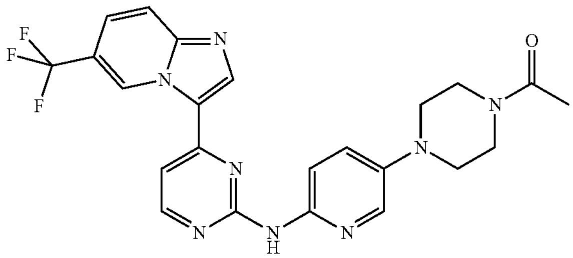 [SMILES: CC(=O)N1CCN(c2ccc(Nc3nccc(-c4cnc5ccc(C(F)(F)F)cn45)n3)nc2)CC1] | 1-(4-(6-((4-(6-(trifluoromethyl)imidazo[1,2-α]pyridin-3-yl)pyrimidin-2-yl)amino)pyridin-3-yl)piperazin-1-yl)ethan-1-one | 482.5 |
| 12 | 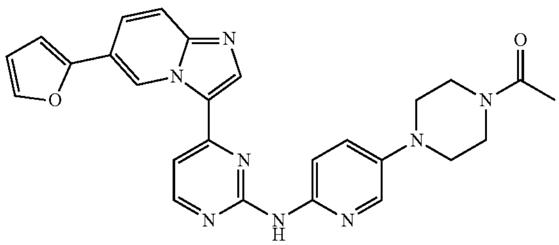 [SMILES: CC(=O)N1CCN(c2ccc(Nc3nccc(-c4cnc5ccc(-c6ccco6)cn45)n3)nc2)CC1] | 1-(4-(6-((4-(6-(furan-2-yl)imidazo[1,2-α]pyridin-3-yl)pyrimidin-2-yl)amino)pyridin-3-yl)piperazin-1-yl)ethan-1-one | 480.5 |
| 13 | 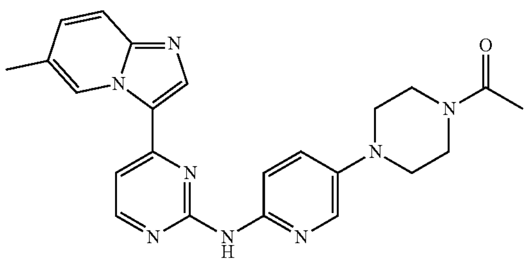 [SMILES: CC(=O)N1CCN(c2ccc(Nc3nccc(-c4cnc5ccc(C)cn45)n3)nc2)CC1] | 1-(4-(6-((4-(6-methylimidazo[1,2-α]pyridin-3-yl)pyrimidin-2-yl)amino)pyridin-3-yl)piperazin-1-yl)ethan-1-one | 428.5 |
| 14 | 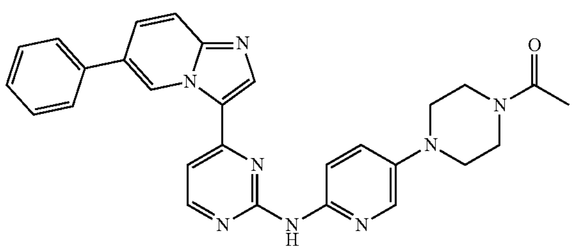 [SMILES: CC(=O)N1CCN(c2ccc(Nc3nccc(-c4cnc5ccc(-c6ccccc6)cn45)n3)nc2)CC1] | 1-(4-(6((4-(6-phenylimidazo[1,2-α]pyridin-3-yl)pyrimidin-2-yl)amino)pyridin-3-yl)piperazin-1-yl)ethan-1-one | 490.6 |
| 15 | 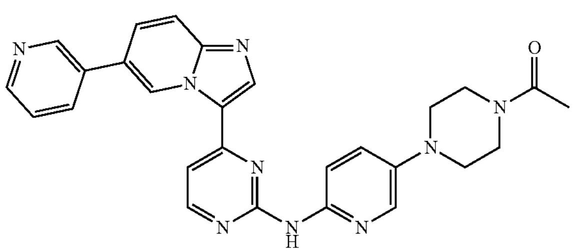 [SMILES: CC(=O)N1CCN(c2ccc(Nc3nccc(-c4cnc5ccc(-c6cccnc6)cn45)n3)nc2)CC1] | 1-(4-(6-((4-(6-(pyridin-3-yl)imidazo[1,2-α]pyridin-3-yl)pyrimidin-2-yl)amino)pyridin-3-yl)piperazin-1-yl)ethan-1-one | 491.6 |
| 16 | 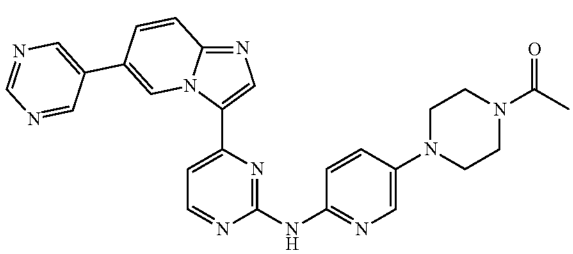 [SMILES: CC(=O)N1CCN(c2ccc(Nc3nccc(-c4cnc5ccc(-c6cncnc6)cn45)n3)nc2)CC1] | 1-(4-(6-((4-(6-(pyrimidin-5-yl)imidazo[1,2-α]pyridin-3-yl)pyrimidin-2-yl)amino)pyridin-3-yl)piperazin-1-yl)ethan-1-one | 492.5 |

TABLE 1-continued

Chemical structure of selected compounds of the present disclosure

| No. | Structure | Name | Mass |
|---|---|---|---|
| 17 | 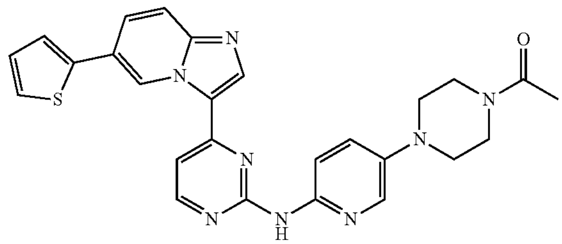 [SMILES: CC(=O)N1CCN(c2ccc(Nc3nccc(-c4cnc5ccc(-c6cccs6)cn45)n3)nc2)CC1] | 1-(4-(6-((4-(6-(thiophen-2-yl)imidazo[1,2-α]pyridin-3-yl)pyrimidin-2-yl)amino)pyridin-3-yl)piperazin-1-yl)ethan-1-one | 496.6 |
| 18 | 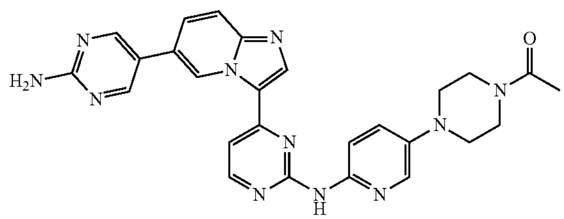 | 1-(4-(6-((4-(6-(2-aminopyrimidin-5-yl)imidazo[1,2-α]pyridin-3-yl)pyrimidin-2-yl)amino)pyridin-3-yl)piperazin-1-yl)ethan-1-one | 507.6 |
| 19 | 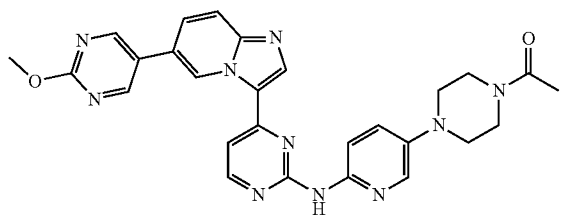 [SMILES: COc1ncc(-c2ccc3ncc(-c4ccnc(Nc5ccc(N6CCN(C(C)=O)CC6)cn5)n4)n3c2)cn1] | 1-(4-(6-((4-(6-(2-methoxypyrimidin-5-yl)imidazo[1,2-α]pyridin-3-yl)pyrimidin-2-yl)amino)pyridin-3-yl)piperazin-1-yl)ethan-1-one | 522.6 |
| 20 | 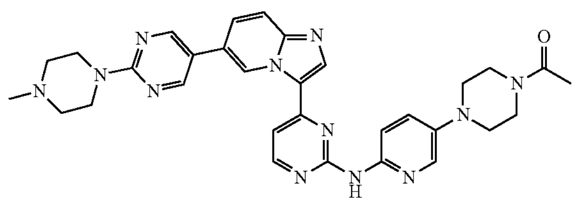 [SMILES: CC(=O)N1CCN(c2ccc(Nc3nccc(-c4cnc5ccc(-c6cnc(N7CCN(C)CC7)nc6)cn45)n3)nc2)CC1] | 1-(4-(6-((4-(6-(2-(4-methylpiperazin-1-yl)pyrimidin-5-yl)imidazo[1,2-α]pyridin-3-yl)pyrimidin-2-yl)amino)pyridin-3-yl)piperazin-1-yl)ethan-1-one | 590.7 |
| 21 | 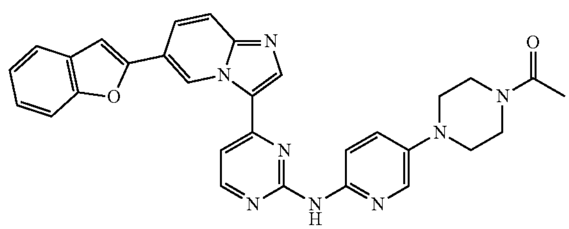 | 1-(4-(6-((4-(6-(benzofuran-2-yl)imidazo[1,2-α]pyridin-3-yl)pyrimidin-2-yl)amino)pyridin-3-yl)piperazin-1-yl)ethan-1-one | 530.6 |
| 22 | 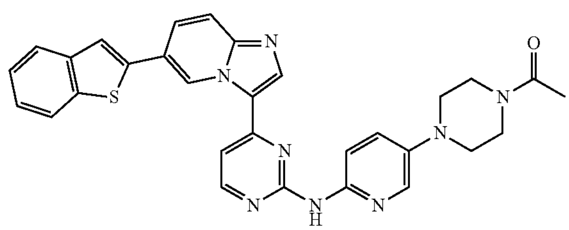 [SMILES: CC(=O)N1CCN(c2ccc(Nc3nccc(-c4cnc5ccc(-c6cc7ccccc7s6)cn45)n3)nc2)CC1] | 1-(4-(6-((4-(6-(benzo[b]thiophen-2-yl)imidazo[1,2-α]pyridin-3-yl)pyrimidin-2-yl)amino)pyridin-3-yl)piperazin-1-yl)ethan-1-one | 546.6 |

TABLE 1-continued

Chemical structure of selected compounds of the present disclosure

| No. | Structure | Name | Mass |
| --- | --- | --- | --- |
| 23 | 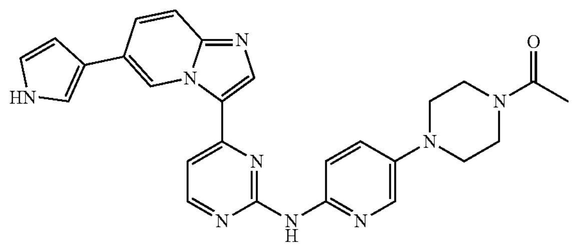 [SMILES: CC(=O)N1CCN(c2ccc(Nc3nccc(-c4cnc5ccc(-c6cc[nH]c6)cn45)n3)nc2)CC1] | 1-(4-(6-((4-(6-(1H-pyrrol-3-yl)imidazo[1,2-α]pyridin-3-yl)pyrimidin-2-yl)amino)pyridin-3-yl)piperazin-1-yl)ethan-1-one | 479.5 |
| 24 | 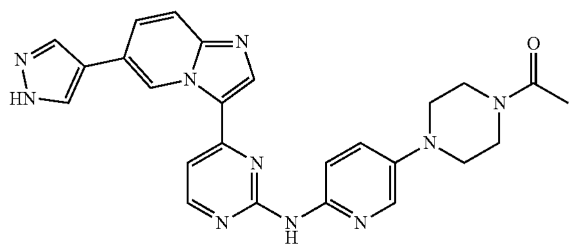 [SMILES: CC(=O)N1CCN(c2ccc(Nc3nccc(-c4cnc5ccc(-c6cn[nH]c6)cn45)n3)nc2)CC1] | 1-(4-(6-((4-(6-(1H-pyrazol-4-yl)imidazo[1,2-α]pyridin-3-yl)pyrimidin-2-yl)amino)pyridin-3-yl)piperazin-l-yl)ethan-1-one | 480.5 |
| 25 | 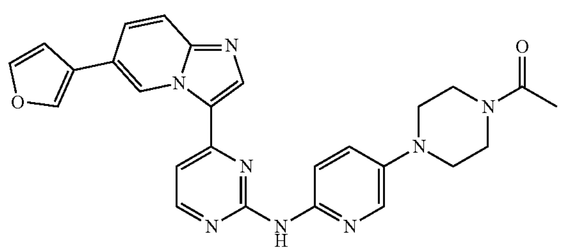 [SMILES: CC(=O)N1CCN(c2ccc(Nc3nccc(-c4cnc5ccc(-c6ccoc6)cn45)n3)nc2)CC1] | 1-(4-(6-((4-(6-(furan-3-yl)imidazo[1,2-α]pyridin-3-yl)pyrimidin-2-yl)amino)pyridin-3-yl)piperazin-1-yl)ethan-l-one | 480.5 |
| 26 | 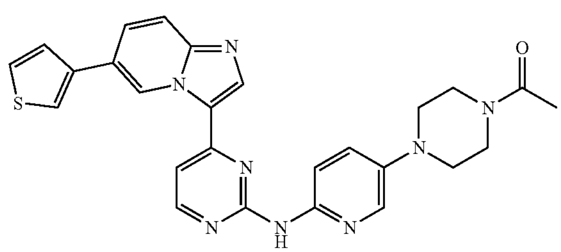 [SMILES: CC(=O)N1CCN(c2ccc(Nc3nccc(-c4cnc5ccc(-c6ccsc6)cn45)n3)nc2)CC1] | 1-(4-(6((4-(6-(thiophen-3-yl)imidazo[1,2-α]pyridin-3-yl)pyrimidin-2-yl)amino)pyridin-3-yl)piperazin-l-yl)ethan-1-one | 496.6 |
| 27 | 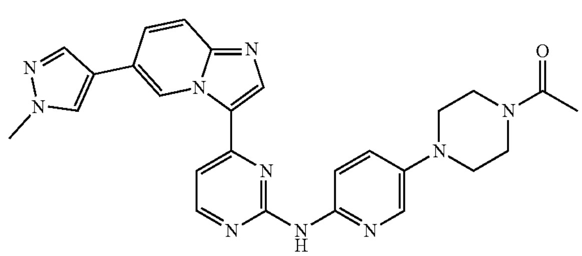 [SMILES: CC(=O)N1CCN(c2ccc(Nc3nccc(-c4cnc5ccc(-c6cnn(C)c6)cn45)n3)nc2)CC1] | 1-(4-(6-((4-(6-(1-methyl-1H-pyrazol-4-yl)imidazo[1,2-α]pyridin-3-yl)pyrimidin-2-yl)amino)pyridin-3-yl)piperazin-l-yl)ethan-l-one | 494.6 |
| 28 | 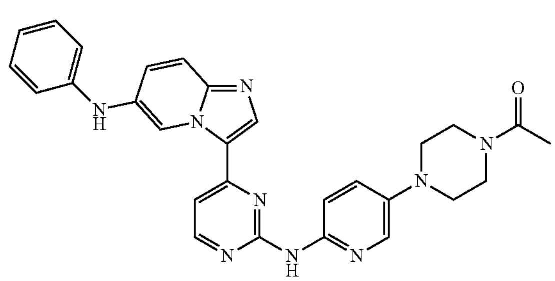 [SMILES: CC(=O)N1CCN(c2ccc(Nc3nccc(-c4cnc5ccc(Nc6ccccc6)cn45)n3)nc2)CC1] | 1-(4-(6-((4-(6-(phenylamino)imidazo[1,2-α]pyridin-3-yl)pyrimidin-2-yl)amino)pyridin-3-yl)piperazin-1-yl)ethan-l-one | 505.6 |

TABLE 1-continued

Chemical structure of selected compounds of the present disclosure

| No. | Structure | Name | Mass |
|---|---|---|---|
| 29 | 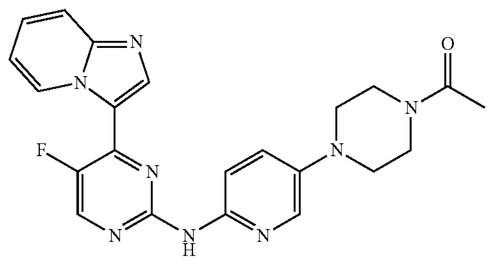 [SMILES: CC(=O)N1CCN(c2ccc(Nc3ncc(F)c(-c4cnc5ccccn45)n3)nc2)CC1] | 1-(4-(6-((5-fluoro-4-(imidazo[1,2-α]pyridin-3-yl)pyrimidin-2-yl)amino)pyridin-3-yl)piperazin-1-yl)ethan-1-one | 432.5 |
| 30 | 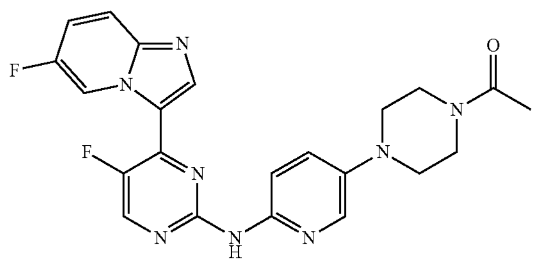 [SMILES: CC(=O)N1CCN(c2ccc(Nc3ncc(F)c(-c4cnc5ccc(F)cn45)n3)nc2)CC1] | 1-(4-(6-((5-fluoro-4-(6-fluoroimidazo[1,2-α]pyridin-3-yl)pyrimidin-2-yl)amino)pyridin-3-yl)piperazin-1-yl)ethan-1-one | 450.4 |
| 31 | 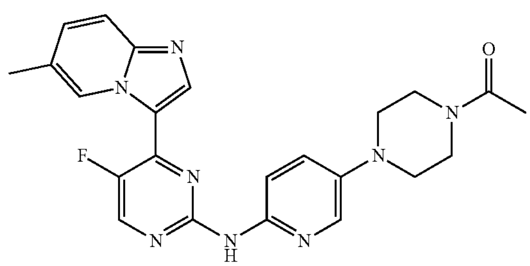 [SMILES: CC(=O)N1CCN(c2ccc(Nc3ncc(F)c(-c4cnc5ccc(C)cn45)n3)nc2)CC1] | 1-(4-(6-((5-fluoro-4-(6-methylimidazo[1,2-α]pyridin-3-yl)pyrimidin-2-yl)amino)pyridin-3-yl)piperazin-1-yl)ethan-1-one | 446.5 |
| 32 | 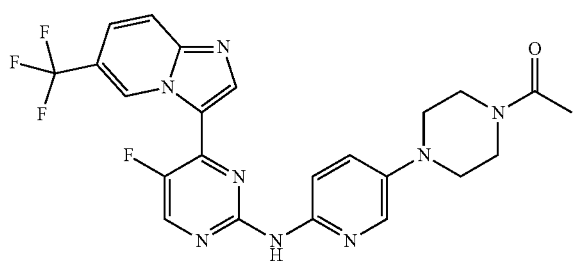 [SMILES: CC(=O)N1CCN(c2ccc(Nc3ncc(F)c(-c4cnc5ccc(C(F)(F)F)cn45)n3)nc2)CC1] | 1-(4-(6-((5-fluoro-4-(6-(trifluoromethyl)imidazo[1,2-α]pyridin-3-yl)pyrimidin-2-ylamino)pyridin-3-yl)piperazin-1-yl)ethan-1-one | 500.5 |
| 33 | 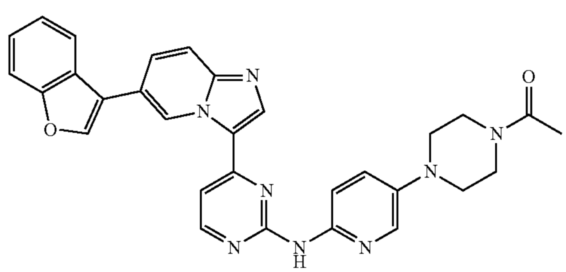 | 1-(4-(6-((4-(6-(benzofuran-3-yl)imidazo[1,2-α]pyridin-3-yl)pyrimidin-2-yl)amino)pyridin-3-yl)piperazin-1-yl)ethan-1-one | 530.6 |
| 34 | 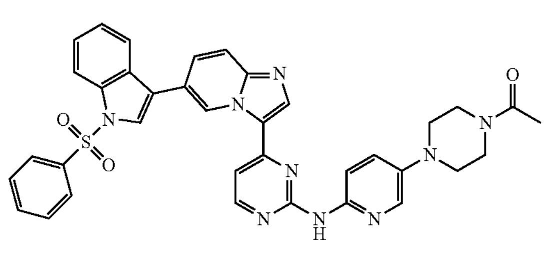 [SMILES: CC(=O)N1CCN(c2ccc(Nc3nccc(-c4cnc5ccc(-c6cn(S(=O)(=O)c7ccccc7)c7ccccc67)cn45)n3)nc2)CC1] | 1-(4-(6-((4-(6-(1-(phenylsulfonyl)-1H-indol-3-yl)imidazo[1,2-α]pyridin-3-yl)pyrimidin-2-yl)amino)pyridin-3-yl)piperazin-1-yl)ethan-1-one | 669.8 |

TABLE 1-continued

Chemical structure of selected compounds of the present disclosure

| No. | Structure | Name | Mass |
|---|---|---|---|
| 35 | 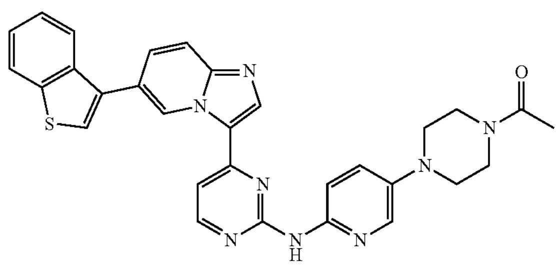 [SMILES: CC(=O)N1CCN(c2ccc(Nc3nccc(-c4cnc5ccc(-c6csc7ccccc67)cn45)n3)nc2)CC1] | 1-(4-(6-((4-(6-(benzo[b]thiophen-3-yl)imidazo[1,2-α]pyridin-3-yl)pyrimidin-2-yl)amino)pyridin-3-yl)piperazin-1-yl)ethan-1-one | 546.6 |
| 36 | 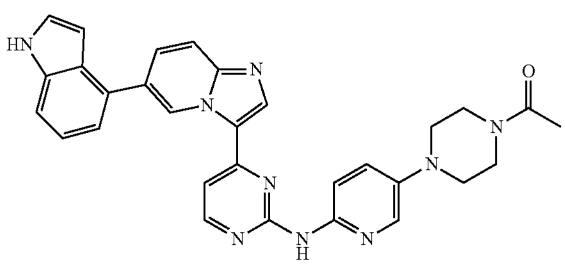 [SMILES: CC(=O)N1CCN(c2ccc(Nc3nccc(-c4cnc5ccc(-c6cccc7[nH]ccc67)cn45)n3)nc2)CC1] | 1-(4-(6-((4-(6-(1H-indol-4-yl)imidazo[1,2-α]pyridin-3-yl)pyrimidin-2-yl)amino)pyridin-3-yl)piperazin-1-yl)ethan-1-one | 529.6 |
| 37 | 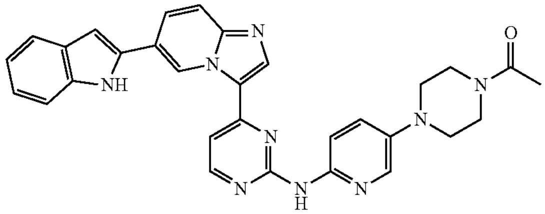 [SMILES: CC(=O)N1CCN(c2ccc(Nc3nccc(-c4cnc5ccc(-c6cc7ccccc7[nH]6)cn45)n3)nc2)CC1] | 1-(4-(6-((4-(6-(1H-indol-2-yl)imidazo[1,2-α]pyridin-3-yl)pyrimidin-2-yl]amino)pyridin-3-yl)piperazin-1-yl)ethan-1-one | 529.6 |
| 38 | 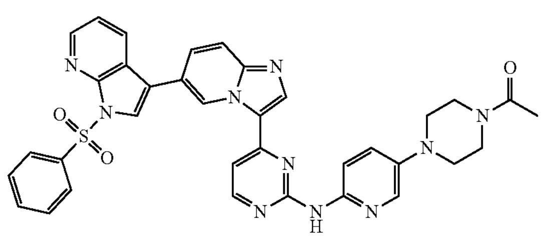 [SMILES: CC(=O)N1CCN(c2ccc(Nc3nccc(-c4cnc5ccc(-c6cn(S(=O)(=O)c7ccccc7)c7ncccc67)cn45)n3)nc2)CC1] | 1-(4-(6-((4-(6-(1-(phenylsulfonyl)-1H-pyrrolo[2,3-b]pyridin-3-yl)imidazo[1,2-α]pyridin-3-yl)pyrimidin-2-yl)amino)pyridin-3-yl)piperazin-1-yl)ethan-1-one | 670.8 |
| 39 | 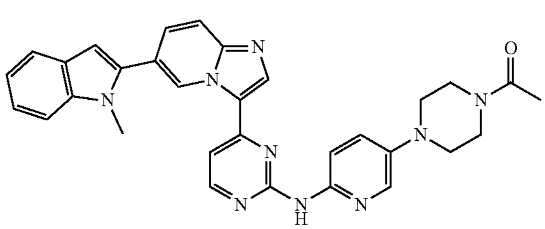 [SMILES: CC(=O)N1CCN(c2ccc(Nc3nccc(-c4cnc5ccc(-c6cc7ccccc7n6C)cn45)n3)nc2)CC1] | 1-(4-(6-((4-(6-(1-methyl-1H-indol-2-yl)imidazo[1,2-α]pyridin-3-yl)pyrimidin-2-yl)amino)pyridin-3-yl)piperazin-1-yl)ethan-1-one | 543.6 |
| 40 | 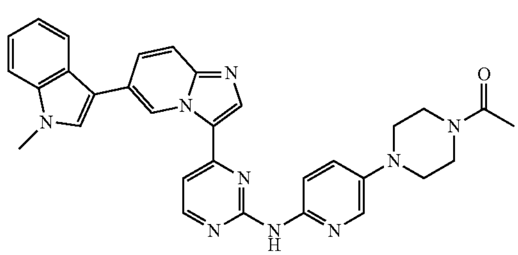 [SMILES: CC(=O)N1CCN(c2ccc(Nc3nccc(-c4cnc5ccc(-c6cn(C)c7ccccc67)cn45)n3)nc2)CC1] | 1-(4-(6-((4-(6-(1-methyl-1H-indol-3-yl)imidazo[1,2-α]pyridin-3-yl)pyrimidin-2-yl)amino)pyridin-3-yl)piperazin-1-yl)ethan-1-one | 543.6 |

TABLE 1-continued

Chemical structure of selected compounds of the present disclosure

| No. | Structure | Name | Mass |
|---|---|---|---|
| 41 | 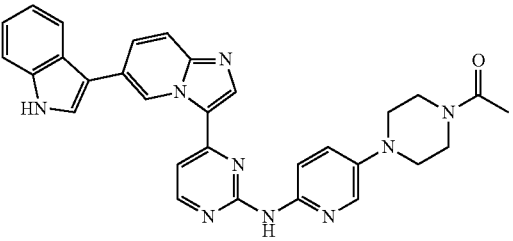 [SMILES: CC(=O)N1CCN(c2ccc(Nc3nccc(-c4cnc5ccc(-c6c[nH]c7ccccc67)cn45)n3)nc2)CC1] | 1-(4-(6-((4-(6-(1H-indol-3-yl)imidazo[1,2-α]pyridin-3-yl)pyrimidin-2-yl)amino)pyridin-3-yl)piperazin-1-yl)ethan-1-one | 529.6 |
| 42 | 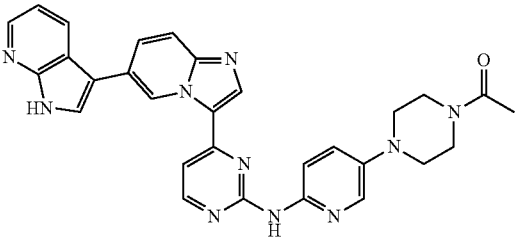 [SMILES: CC(=O)N1CCN(c2ccc(Nc3nccc(-c4cnc5ccc(-c6c[nH]c7ncccc67)cn45)n3)nc2)CC1] | 1-(4-(6-((4-(6-(1H-pyrrolo[2,3-b]pyridin-3-yl)imidazo[1,2-α]pyridin-3-yl)pyrimidin-2-yl)amino)pyridin-3-yl)piperazin-1-yl)ethan-1-one | 530.6 |
| 43 | 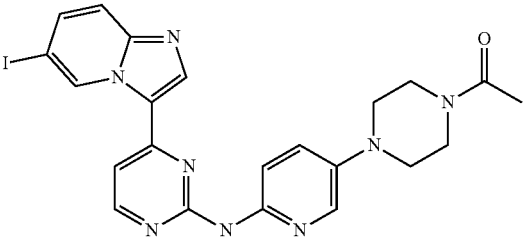 | 1-(4-(6-((4-(6-iodoimidazo[1,2-α]pyridin-3-yl)pyrimidin-2-yl)amino)pyridin-3-yl)piperazin-1-yl)ethan-1-one | 540.4 |
| 44 | 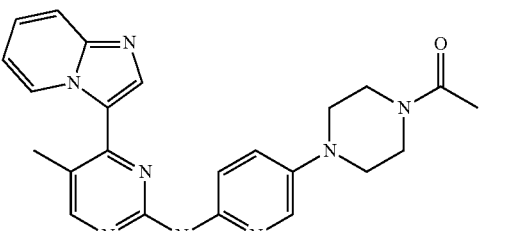 | 1-(4-(6-((4-(imidazo[1,2-α]pyridin-3-yl)-5-methylpyrimidin-2-yl)amino)pyridin-3-yl)piperazin-1-yl)ethan-1-one | 428.5 |
| 45 | 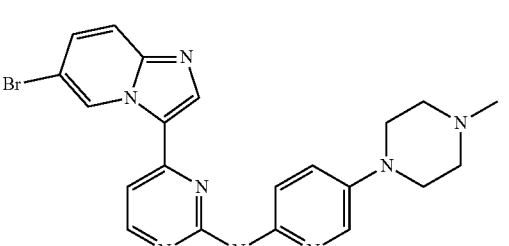 | 4-(6-bromoimidazo[1,2-α]pyridin-3-yl)-N-(5-(4-methylpiperazin-1-yl)pyridin-2-yl)pyrimidin-2-amine | 465.4 |
| 46 | 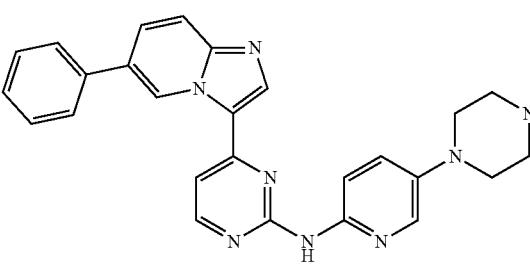 | N-(5-(4-methylpiperazin-1-yl)pyridin-2-yl)-4-(6-phenylimidazo[1,2-α]pyridin-3-yl)pyrimidin-2-amine | 462.6 |

TABLE 1-continued

Chemical structure of selected compounds of the present disclosure

| No. | Structure | Name | Mass |
|---|---|---|---|
| 47 | 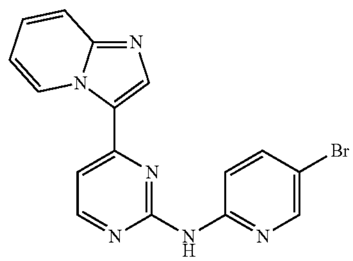 [SMILES: Brc1ccc(Nc2nccc(-c3cnc4ccccn34)n2)nc1] | N-(5-bromopyridin-2-yl)-4-(imidazo[1,2-α]pyridin-3-yl)pyrimidin-2-amine | 367.2 |
| 48 | 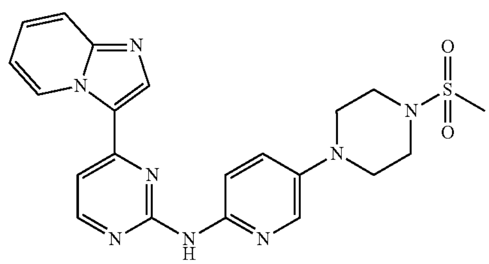 [SMILES: CS(=O)(=O)N1CCN(c2ccc(Nc3nccc(-c4cnc5ccccn45)n3)nc2)CC1] | 4-(imidazo[1,2-α]pyridin-3-yl)-N-(5-(4-(methylsulfonyl)piperazin-1-yl)pyridin-2-yl)pyrimidin-2-amine | 450.5 |
| 49 | 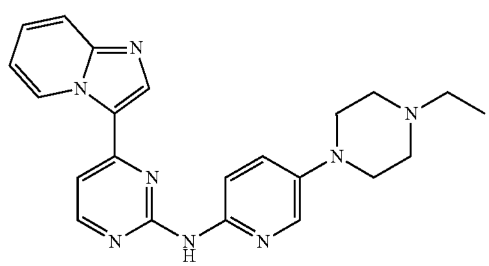 [SMILES: CCN1CCN(c2ccc(Nc3nccc(-c4cnc5ccccn45)n3)nc2)CC1] | 1-ethyl-4-(6-((4-(imidazol[1,2-α]pyridin-3-yl)pyrimidin-2-yl)ammonio)pyridin-3-yl)piperazin-1-ium formate | 492.5 |
| 50 | 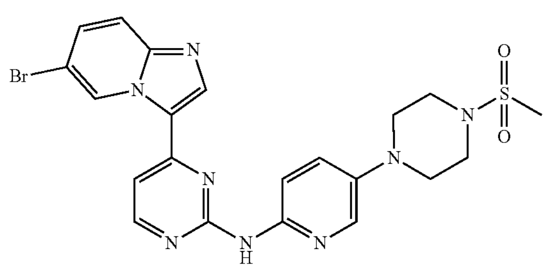 [SMILES: CS(=O)(=O)N1CCN(c2ccc(Nc3nccc(-c4cnc5ccc(Br)cn45)n3)nc2)CC1] | 4-(6-bromoimidazo[1,2-α]pyridin-3-yl)-N-(5-(4-(methylsulfonyl)piperazin-1-yl)pyridin-2-yl)pyrimidin-2-amine | 529.4 |
| 51 | 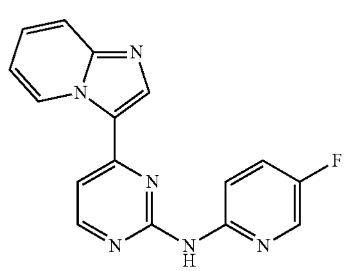 [SMILES: Fc1ccc(Nc2nccc(-c3cnc4ccccn34)n2)nc1] | N-(5-fluoropyridin-2-yl)-4-(imidazo[1,2-α]pyridin-3-yl)pyrimidin-2-amine | 306.3 |

TABLE 1-continued

Chemical structure of selected compounds of the present disclosure

| No. | Structure | Name | Mass |
|---|---|---|---|
| 52 | 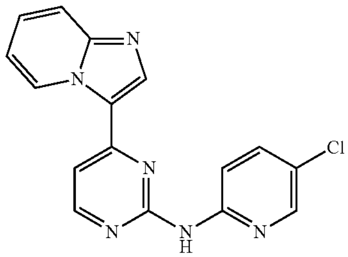 [SMILES: Clc1ccc(Nc2nccc(-c3cnc4ccccn34)n2)nc1] | N-(5-chloropyridin-2-yl)-4-(imidazo[1,2-α]pyridin-3-yl)pyrimidin-2-amine | 322.8 |
| 53 | 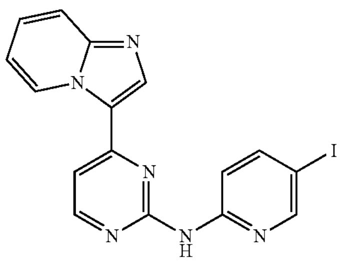 [SMILES: Ic1ccc(Nc2nccc(-c3cnc4ccccn34)n2)nc1] | 4-(imidazo[1,2-α]pyridin-3-yl)-N-(5-iodopyridin-2-yl)pyrimidin-2-amine | 414.2 |
| 54 | 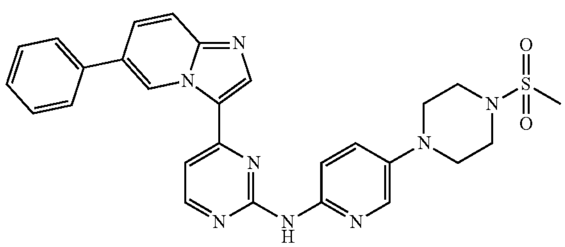 [SMILES: CS(=O)(=O)N1CCN(c2ccc(Nc3nccc(-c4cnc5ccc(-c6ccccc6)cn45)n3)nc2)CC1] | N-(5-(4-(methylsulfonyl)piperazin-l-yl)pyridin-2-yl)-4-(6-phenylimidazo[1,2-α]pyridin-3-yl)pyrimidin-2-amine | 526.6 |
| 55 | 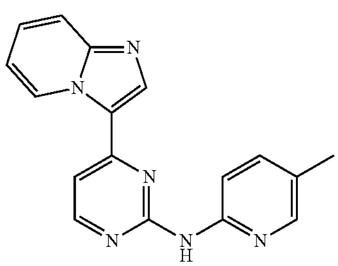 [SMILES: Cc1ccc(Nc2nccc(-c3cnc4ccccn34)n2)nc1] | 4-(imidazo[1,2-α]pyridin-3-yl)-N-(5-methylpyridin-2-yl)pyrimidin-2-amine | 302.3 |
| 56 | 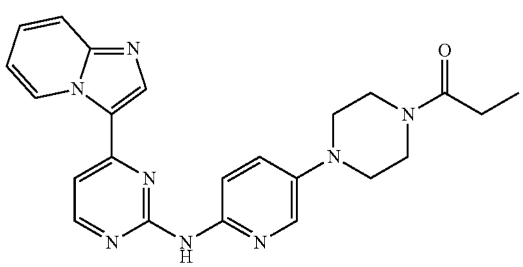 [SMILES: CCC(=O)N1CCN(c2ccc(Nc3nccc(-c4cnc5ccccn45)n3)nc2)CC1] | 1-(4-(6-((4-(imidazo[1,2-α]pyridin-3-yl)pyrimidin-2-yl)amino)pyridin-3-yl)piperazin-l-yl)propan-1-one | 428.5 |
| 57 | 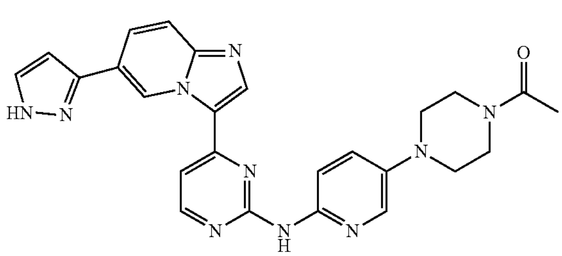 [SMILES: CC(=O)N1CCN(c2ccc(Nc3nccc(-c4cnc5ccc(-c6cc[nH]n6)cn45)n3)nc2)CC1] | 1-(4-(6-((4-(6-(1H-pyrazol-3-yl)imidazo[1,2-α]pyridin-3-yl)pyrimidin-2-yl)amino)pyridin-3-yl)piperazin-1-yl)ethan-1-one | 480.5 |

TABLE 1-continued

Chemical structure of selected compounds of the present disclosure

| No. | Structure | Name | Mass |
|---|---|---|---|
| 58 | 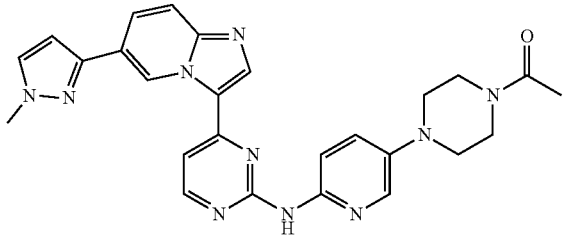 [SMILES: CC(=O)N1CCN(c2ccc(Nc3nccc(-c4cnc5ccc(-c6ccn(C)n6)cn45)n3)nc2)CC1] | 1-(4-(6-((4-(6-(1-methyl-1H-pyrazol-3-yl)imidazo[1,2-α]pyridin-3-yl)pyrimidin-2-yl)amino)pyridin-3-yl)piperazin-1-yl)ethan-1-one | 494.6 |
| 59 | 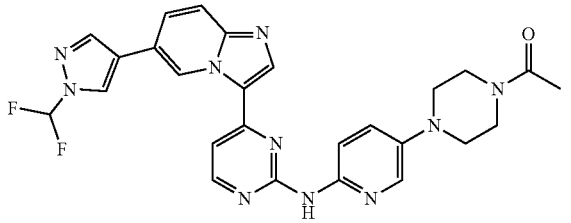 [SMILES: CC(=O)N1CCN(c2ccc(Nc3nccc(-c4cnc5ccc(-c6cnn(C(F)F)c6)cn45)n3)nc2)CC1] | 1-(4-(6-((4-(6-(1-(difluoromethyl)-1H-pyrazol-4-yl)imidazo[1,2-α]pyridin-3-yl)pyrimidin-2-yl)amino)pyridin-3-yl)piperazin-1-yl)ethan-1-one | 530.5 |
| 60 | 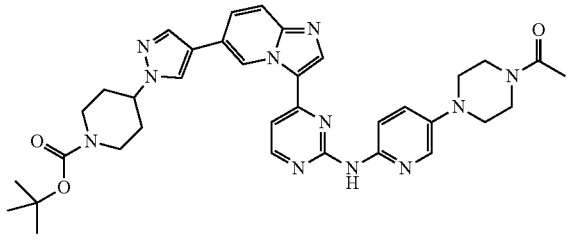 [SMILES: CC(=O)N1CCN(c2ccc(Nc3nccc(-c4cnc5ccc(-c6cnn(C7CCN(C(=O)OC(C)(C)C)CC7)c6)cn45)n3)nc2)CC1] | tert-butyl 4-(4-(3-(2-((5-(4-acetylpiperazin-1-yl)pyridin-2-yl)amino)pyrimidin-4-yl)imidazo[1,2-α]pyridin-6-yl)-1H-pyrazol-1-yl)piperidine-1-carboxylate | 663.8 |
| 61 | 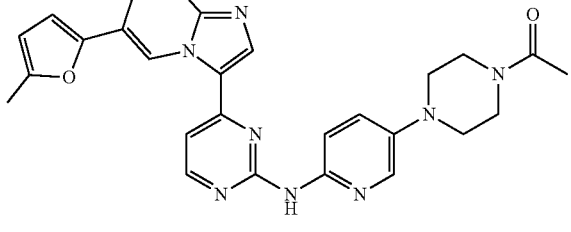 | 1-(4-(6-((4-(6-(5-methylfuran-2-yl)imidazo[1,2-α]pyridin-3-yl)pyrimidin-2-yl)amino)pyridin-3-yl)piperazin-1-yl)ethan-1-one | 494.6 |
| 62 | 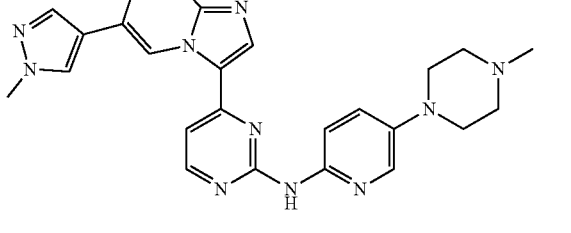 | 4-(6-(1-methyl-1H-pyrazol-4-yl)imidazo[1,2-α]pyridin-3-yl)-N-(5-(4-methylpiperazin-1-yl)pyridin-2-yl)pyrimidin-2-amine | 466.6 |
| 63 | 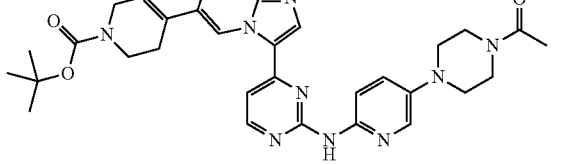 | tert-butyl 4-(3-(2-((5-(4-acetylpiperazin-1-yl)pyridin-2-yl)amino)pyrimidin-4-yl)imidazo[1,2-α]pyridin-6-yl)-3,6-dihydropyridine-1(2H)-carboxylate | 595.7 |

TABLE 1-continued

Chemical structure of selected compounds of the present disclosure

| No. | Structure | Name | Mass |
|---|---|---|---|
| 64 | 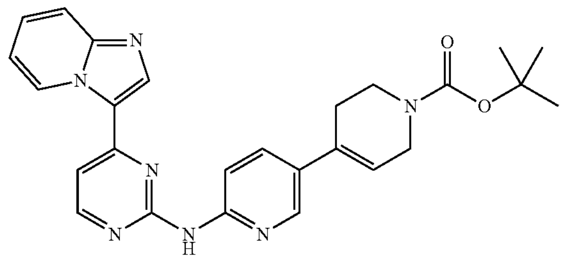 [SMILES: CC(C)(C)OC(=O)N1CC=C(c2ccc(Nc3nccc(-c4cnc5ccccn45)n3)nc2)CC1] | tert-butyl 6-((4-(imidazo[1,2-α]pyridin-3-yl)pyrimidin-2-yl)amino)-3',6'-dihydro-[3,4'-bipyridine]-1'(2'H)-carboxylate | 469.5 |
| 65 | 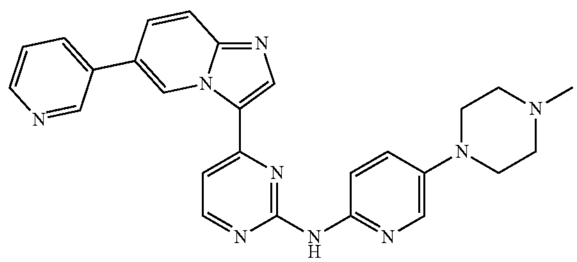 [SMILES: CN1CCN(c2ccc(Nc3nccc(-c4cnc5ccc(-c6cccnc6)cn45)n3)nc2)CC1] | N-(5-(4-methylpiperazin-1-yl)pyridin-2-yl)-4-(6-(pyridin-3-yl)imidazo[1,2-α]pyridin-3-yl)pyrimidin-2-amine | 463.5 |
| 66 | 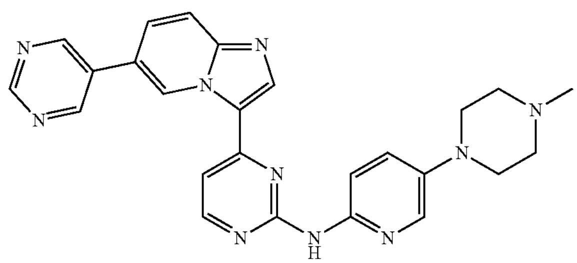 [SMILES: CN1CCN(c2ccc(Nc3nccc(-c4cnc5ccc(-c6cncnc6)cn45)n3)nc2)CC1] | N-(5-(4-methylpiperazin-1-yl)pyridin-2-yl)-4-(6-(pyrimidin-5-yl)limidazo[1,2-α]pyridin-3-yl)pyrimidin-2-amine | 464.5 |
| 67 | 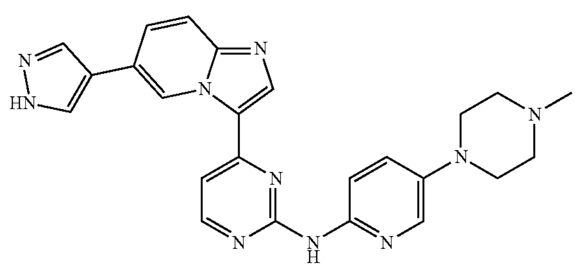 [SMILES: CN1CCN(c2ccc(Nc3nccc(-c4cnc5ccc(-c6cn[nH]c6)cn45)n3)nc2)CC1] | 4-(6-(1H-pyrazol-4-yl)imidazo[1,2-α]pyridin-3-yl)-N-(5-(4-methylpiperazin-1-yl)pyridin-2-yl)pyrimidin-2-amine | 452.5 |
| 68 | 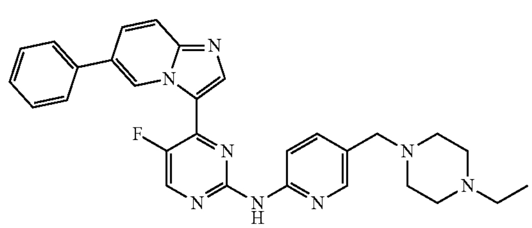 [SMILES: CCN1CCN(Cc2ccc(Nc3ncc(F)c(-c4cnc5ccc(-c6ccccc6)cn45)n3)nc2)CC1] | N-(5-((4-ethylpiperazin-1-yl)methyl)pyridin-2-yl)-5-fluoro-4-(6-phenylimidazo[1,2-α]pyridin-3-yl)pyrimidin-2-amine | 508.6 |
| 69 | 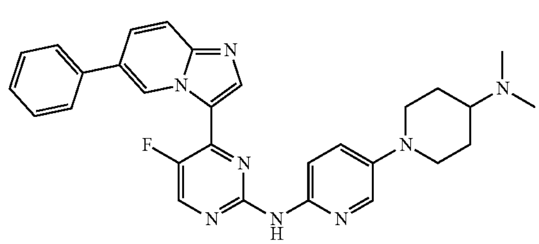 [SMILES: CN(C)C1CCN(c2ccc(Nc3ncc(F)c(-c4cnc5ccc(-c6ccccc6)cn45)n3)nc2)CC1] | N-(5-(4-(dimethylamino)piperidin-1-yl)pyridin-2-yl)-5-fluoro-4-(6-phenylimidazo[1,2-α]pyridin-3-yl)pyrimidin-2-amine | 508.6 |

The compounds (and pharmaceutically acceptable salts, solvates and prodrugs thereof) may be administered in combination with one or more additional agent(s) for the treatment of cancer or another proliferative disease or condition. For example, the compounds may be used in combination with other anti-cancer agents in order to inhibit more than one cancer signalling pathway simultaneously so as to make cancer cells more susceptible to anti-cancer therapies (eg treatments with other anti-cancer agents, chemotherapy, radiotherapy or a combination thereof). As such, the compounds of formula I may be used in combination with one or more of the following categories of anti-cancer agents:

- other anti-proliferative/antineoplastic drugs and combinations thereof, as used in medical oncology, such as alkylating agents (eg cis-platin, oxaliplatin, carboplatin, cyclophosphamide, nitrogen mustard, melphalan, chlorambucil, busulphan, temozolamide and nitrosoureas); antimetabolites (eg gemcitabine and antifolates such as fluoropyrimidines like 5-fluorouracil and tegafur, raltitrexed, methotrexate, cytosine arabinoside, fludarabine and hydroxyurea); antitumour antibiotics (eg anthracyclines such as adriamycin, bleomycin, doxorubicin, daunomycin, epirubicin, idarubicin, mitomycin-C, dactinomycin and mithramycin); antimitotic agents (eg *vinca* alkaloids such as vincristine, vinblastine, vindesine and vinorelbine and taxoids including taxol and taxotere and polokinase inhibitors); and topoisomerase inhibitors (eg epipodophyllotoxins such as etoposide and teniposide, amsacrine, topotecan and camptothecin);
- cytostatic agents such as antiestrogens (eg tamoxifen, fulvestrant, toremifene, raloxifene, droloxifene and iodoxyfene), antiandrogens (eg bicalutamide, flutamide, nilutamide and cyproterone acetate), LHRH antagonists or LHRH agonists (eg goserelin, leuprorelin and buserelin), progestogens (eg megestrol acetate), aromatase inhibitors (eg as anastrozole, letrozole, vorazole and exemestane) and inhibitors of 5α-reductase such as finasteride;
- anti-invasion agents (eg c-Src kinase family inhibitors such as 4-(6-chloro-2,3-methylenedioxyanilino)-7-[2-(4-methylpiperazin-1-yl)ethoxy]-5-tetrahydropyran-4-yloxyquinazoline (AZD0530; International Patent Publication No WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib) and bosutinib (SKI-606)), and metalloproteinase inhibitors including marimastat, inhibitors of urokinase plasminogen activator receptor function or antibodies to heparanase;
- inhibitors of growth factor function (eg growth factor antibodies and growth factor receptor antibodies such as the anti-erbB2 antibody trastuzumab (Herceptin™), the anti-EGFR antibody panitumumab, the anti-erbB1 antibody cetuximab (Erbitux, C225) and any growth factor or growth factor receptor antibodies disclosed by Stern et al. Critical reviews in oncology/haematology, 2005, Vol. 54, pp 11-29). Such inhibitors also include tyrosine kinase inhibitors such as inhibitors of the epidermal growth factor family (eg EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (eg Ras/Raf signalling inhibitors such as farnesyl transferase inhibitors including sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (eg AZD1152, PH739358, VX-680, MLN8054, R763, MP235, MP529, VX-528 and AX39459) and cyclin dependent kinase inhibitors such as CDK2 and/or CDK9 inhibitors;
- antiangiogenic agents such as those which inhibit the effects of vascular endothelial growth factor (eg the anti-vascular endothelial cell growth factor antibody bevacizumab (Avastin™) and VEGF receptor tyrosine kinase inhibitors such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy)quinazoline (AZD2171; Example 240 within International Patent Publication No WO 00/47212), compounds such as those disclosed in International Patent Publication Nos WO97/22596, WO 97/30035, WO 97/32856 and WO 98/13354, and compounds that work by other mechanisms (eg linomide, inhibitors of integrin αvβ3 function and angiostatin);
- vascular damaging agents such as Combretastatin A4 and compounds disclosed in International Patent Publication Nos WO 99/02166, WO 00/40529, WO 00/41669, WO 01/92224, WO 02/04434 and WO 02/08213;
- endothelin receptor antagonists such as zibotentan (ZD4054) or atrasentan;
- antisense therapies such as those which are directed to the targets listed above, such as ISIS 2503, an anti-ras antisense;
- gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and
- immunotherapy approaches, including for example ex vivo and in vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Where used in combination with other anti-cancer agents, a compound of the present disclosure and the other anti-cancer agent can be administered in the same pharmaceutical composition or in separate pharmaceutical compositions. If administered in separate pharmaceutical compositions, the compound and the other anti-cancer agent may be administered simultaneously or sequentially in any order (eg within seconds or minutes or even hours (eg 2 to 48 hours)).

The compound of the present disclosure is typically applied to the treatment of cancer or another proliferative cell disease or condition in a human subject. However, the subject may also be selected from, for example, livestock animals (eg cows, horses, pigs, sheep and goats), companion animals (eg dogs and cats) and exotic animals (eg non-human primates, tigers, elephants etc).

Cancers and other proliferative cell diseases and conditions that may be treated in accordance with the present disclosure include biliary tract cancer, brain cancer and other cancers of the central nervous system (CNS) (including glioblastomas and medulloblastomas), neuroblastomas, breast cancer, cervical cancer, ovarian cancer (including those arising from epithelial cells, stromal cells, germ cells, and mesenchymal cells), choriocarcinoma, colorectal cancer, endometrial cancer, liver cancer, lung cancer, oesophageal cancer, gastric cancer, haematological neoplasms (including acute lymphocytic leukemia (ALL)), chronic lymphocytic leukemia (CLL) and chronic myelogenous leukemia (CML), and acute myeloid leukaemia (AML), multiple myeloma, AIDS-associated leukemias and adult T-cell leukemia lymphoma, lymphomas (including Non-Hodgkin's lymphoma, Hodgkin's disease and lymphocytic lymphomas)), intraepithelial neoplasms (including Bowen's disease and Paget's disease), oral cancer (including squamous cell carcinoma), pancreatic cancer, prostate cancer, sarcomas (including leiomyosarcoma, rhabdomyosarcoma, liposarcoma, fibrosarcoma, and osteosarcoma), skin cancer (including melanoma, Kaposi's sarcoma, basocellulare cancer, and squamous cell cancer), testicular cancer (including germinal tumours such as seminoma, non-seminoma teratomas, and choriocarcinomas), stromal tumours, germ cell tumours, thyroid cancer (including thyroid adenocarcinoma and medullar carcinoma), and renal cancer (including adenocarcinoma and Wilms' tumour).

In some embodiments, the compounds of the present disclosure are used to treat cancers characterised by expression or over-expression of FLT3 or FLT3-ITD (a mutated form including an internal tandem duplication associated with very poor prognosis in some patients with acute myeloid leukaemia (AML)) including, for example, several haematologic malignancies (Stirewalt D L and J P Radich, *Nat Rev Cancer* 3:650-665 (2003) such as AML and other FLT3-activated cancers. FLT3 over-expression may be determined by, for example, assessing the amount of mRNA encoding FLT3 in a suitable sample using any of the techniques well known to those skilled in the art (eg quantitative amplification techniques such as qPCR).

The compounds of the present disclosure may be formulated into a pharmaceutical composition with a pharmaceutically acceptable carrier, diluent and/or excipient. Examples of suitable carriers and diluents are well known to those skilled in the art, and are described in, for example, Remington's Pharmaceutical Sciences, Mack Publishing Co., Easton, PA 1995. Examples of suitable excipients for the various different forms of pharmaceutical compositions described herein may be found in the Handbook of Pharmaceutical Excipients, $2^{nd}$ Edition, (1994), Edited by A Wade and P J Weller. Examples of suitable carriers include lactose, starch, glucose, methyl cellulose, magnesium stearate, mannitol, sorbitol and the like. Examples of suitable diluents include ethanol, glycerol and water. The choice of carrier, diluent and/or excipient may be made with regard to the intended route of administration and standard pharmaceutical practice.

A pharmaceutical composition comprising a compound of the present disclosure may further comprise any suitable binders, lubricants, suspending agents, coating agents and solubilising agents. Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like. Preservatives, stabilising agents, dyes and even flavouring agents may be provided in the pharmaceutical composition. Examples of preservatives include sodium benzoate, sorbic acid and esters of p-hydroxybenzoic acid. Anti-oxidants and suspending agents may be also used.

A pharmaceutical composition comprising a compound of the present disclosure may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration. For oral administration, particular use may be made of compressed tablets, pills, tablets, gellules, drops, and capsules. For other forms of administration, a pharmaceutical composition may comprise solutions or emulsions which may be injected intravenously, intraarterially, intrathecally, subcutaneously, intradermally, intraperitoneally or intramuscularly, and which are prepared from sterile or sterilisable solutions. A pharmaceutical composition comprising a compound of the present disclosure may also be in form of suppositories, pessaries, suspensions, emulsions, lotions, ointments, creams, gels, sprays, solutions or dusting powders. A pharmaceutical composition may be formulated in unit dosage form (ie in the form of discrete portions containing a unit dose, or a multiple or sub-unit of a unit dose).

The compounds of the present disclosure may be provided as a pharmaceutically acceptable salt including, for example, suitable acid addition or base salts thereof. A review of suitable pharmaceutical salts may be found in Berge et al., *J Pharm Sci* 66:1-19 (1977). Salts are formed, for example with strong inorganic acids such as mineral acids (eg sulfuric acid, phosphoric acid or hydrohalic acids), with strong organic carboxylic acids, such as alkanecarboxylic acids of 1 to 4 carbon atoms which are unsubstituted or substituted (eg by halogen), such as acetic acid, with saturated or unsaturated dicarboxylic acids (eg oxalic, malonic, succinic, maleic, fumaric, phthalic or terephthalic acid), with hydroxycarboxylic acids (eg ascorbic, glycolic, lactic, malic, tartaric or citric acid), with amino acids (eg aspartic or glutamic acid), with benzoic acid, or with organic sulfonic acids (eg ($C_1$-$C_4$)-alkyl- or aryl-sulfonic acids which are unsubstituted or substituted by, for example, halogen) such as methane- or p-toluene sulfonic acid).

The compounds of the present disclosure may be provided in their various crystalline forms, polymorphic forms and (an)hydrous forms. In this regard, it is well known to those skilled in the art that chemical compounds may be isolated in any of such forms by slightly varying the method of purification and or isolation from the solvents used in the synthetic preparation of such compounds.

The present disclosure further provides a method of synthesising a compound according to formula I, or a pharmaceutically acceptable salt, solvate or prodrug thereof.

With regard to the description of the synthetic methods described below and in the referenced synthetic methods that are used to prepare starting materials, it will be understood by those skilled in the art that all proposed reaction conditions, including choice of solvent, reaction atmosphere, reaction temperature, duration of the experiment and workup procedures, can be readily selected. Moreover, it will be understood by those skilled in the art that the functionality present on various portions of the molecule must be compatible with the reagents and reaction conditions utilised.

Necessary starting materials may be obtained by standard procedures of organic chemistry. The preparation of such starting materials is described in conjunction with the following representative process variants and within the examples hereinafter. Alternatively, necessary starting materials may be obtainable by analogous procedures to those illustrated which are within the ordinary skill of those skilled in the art. Further, it will be appreciated that during the synthesis of the compounds, in the processes described below, or during the synthesis of certain starting materials, it may be desirable to protect certain substituent groups to prevent their undesired reaction. Those skilled in the art will readily recognise when such protection is required, and how such protecting groups may be put in place, and later removed. Examples of protecting groups are described in, for example, Protective Groups in Organic Synthesis by Theodora Green (publisher: John Wiley & Sons). Protecting groups may be removed by any convenient method well known to those skilled in the art as appropriate for the removal of the protecting group in question, such methods being chosen so as to effect removal of the protecting group with the minimum disturbance of groups elsewhere in the molecule. Thus, if reactants include, for example, groups such as amino, carboxyl or hydroxyl, it may be desirable to protect the group in some of the reactions mentioned herein.

The compounds of the present disclosure may be prepared by, for example, the general synthetic methodologies described in International Patent Publication No WO 2013/156780, which is herein incorporated by reference.

In a further aspect of the present disclosure, a method of synthesising a compound of the present disclosure (or a pharmaceutically acceptable salt, solvate or prodrug thereof) is provided wherein the method comprises:

a) for a compound of Formula I, reacting a compound of formula A:

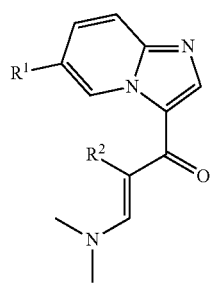

A wherein
R$^1$ and R$^2$ are as defined above in respect of Formula I, with a suitable 2-aminopyridine derivative; or, if necessary, reacting a compound of formula B

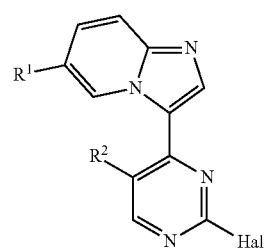

B wherein Hal is F, Cl, Br or I; and R$^1$ and R$^2$ are as defined above in respect of Formula I, with a suitable pyridinylguanidine derivative; and if necessary b) removing any protecting groups present, and/or forming a pharmaceutically acceptable salt, solvate or prodrug thereof.

The coupling reaction between the compound of formula A or formula B and the 2-aminopyridine/pyridinylguanidine derivative may take place in the presence of a suitable solvent or solvent mixture. Those skilled in the art will be able to readily select a suitable solvent or solvent mixture for use in this reaction. Examples of suitable solvents include alcohols, acetonitrile, halogenated solvents, etc.

In addition, those skilled in the art will be able to select appropriate reaction conditions to use in the coupling reaction of the compound of formula A or formula B. However, typically, the reaction will be carried out in anhydrous conditions and in the presence of an inert atmosphere, such as argon or nitrogen. The reaction may also be carried out an elevated temperature, such as, for example, within the range of 80 to 180° C. for a suitable time period of, for example, 20 minutes to 48 hours. Suitably, the reaction is carried out under microwave heating, for example, at 80 to 180° C. for 20 minutes to 1.5 hour.

The resultant compound can be isolated and purified using techniques well known to those skilled in the art.

The method of synthesising a compound of the present disclosure (or a pharmaceutically acceptable salt, solvate or prodrug thereof) may further comprise:

c) subjecting the compound of formula I to a salt exchange (particularly in situations where the compound is formed as a mixture of different salt forms).

The salt exchange may comprise mobilising the compound on a suitable solid support or resin, and eluting the compound with an appropriate acid to yield salt of the compound of formula I.

An example of a particularly suitable method for synthesising a compound of the present disclosure is shown as Scheme 1 below.

Scheme 1

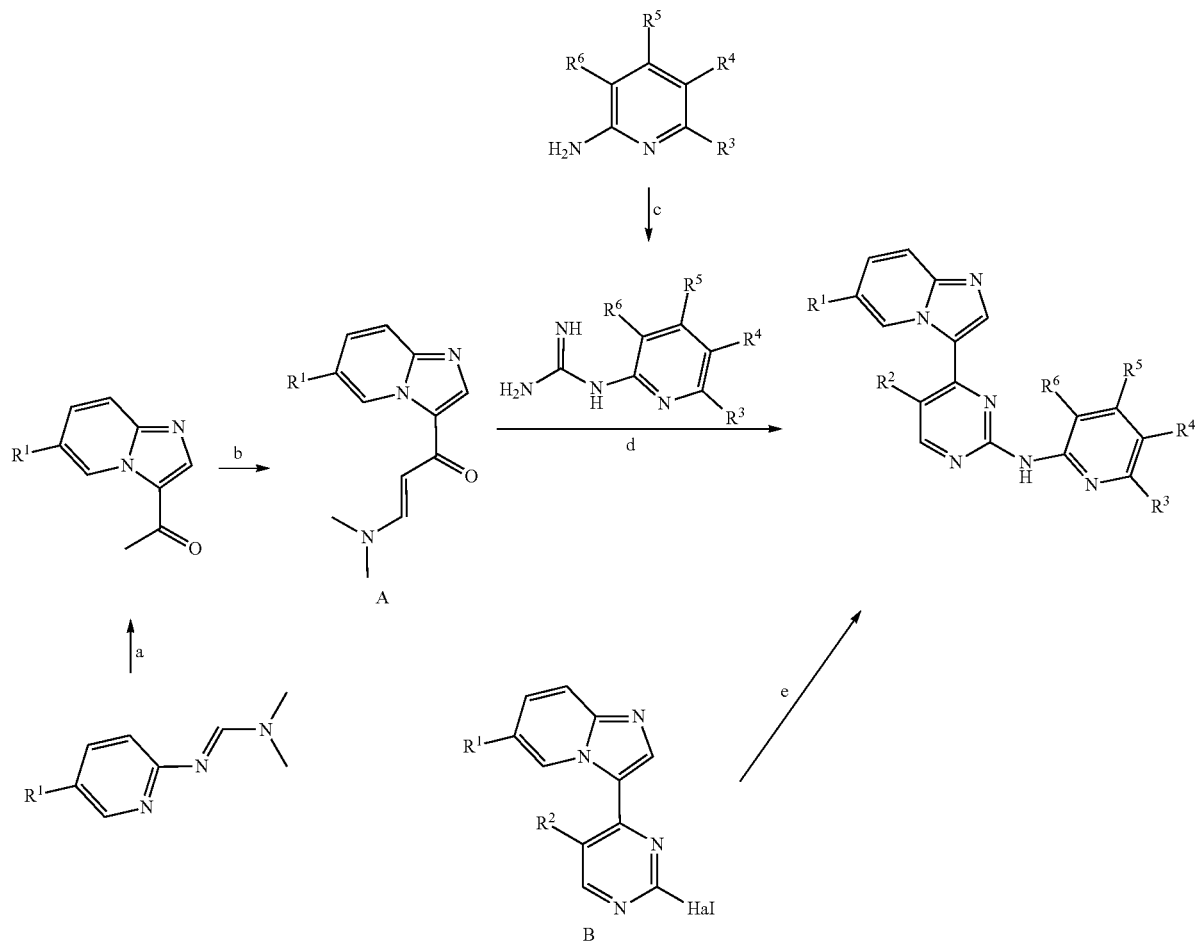

wherein the general reaction conditions are: (a) chloroacetone, EtOH, reflux, o/n; (b) DMF-DMA, reflux, o/n; (c) i. N,N'-bis-Boc-S-methylisothiourea, HgCl$_2$, Et$_3$N, DCM, 0° C. to rt, o/n; ii. TFA/DCM/H$_2$O (18:9:1), 50° C., o/n; (d) NaOH, 2-methoxyethanol, microwave, 160-200° C., 1 h; (e) pyridine-2-amine, Cs$_2$CO$_3$, Pd$_2$(dba)$_3$ or Pd(OAc)$_2$, xantphos or BINAP, 1,4-dioxane, microwave, 160-200° C., 1 h.

The disclosure is hereinafter described with reference to the following, non-limiting examples and accompanying FIGURES.

EXAMPLES

Example 1 Synthesis

General $^1$H spectra were recorded at 298 K on a Bruker AVANCE III HD 500 spectrometer, and were analysed using Bruker Topspin 3.2 software. $^1$H NMR signals are reported with chemical shift values δ (ppm), multiplicity (s=singlet, d=doublet, t=triplet, q=quartet, dd=doublet of doublets, dt=doublet of triplets, td=triplet of doublets, ddd=doublet of doublet of doublets, m=multiplet and br=broad), relative integral, coupling constants J(Hz) and assignments. High resolution mass spectra were recorded on an AB SCIEX TripleTOF 5600 mass spectrometer (Concord, ON, Canada), and ionisation of all samples was carried out using ESI.

General synthetic procedure A. To DMF-DMA (1.6 equiv.) was added an aminopyridine (1.0 equiv.). The reaction mixture was heated at reflux overnight, cooled down to room temperature and concentrated under reduced pressure. The residue was dissolved in EtOH (litre per mole of aminopyridine used), and 1-chloroacetone (1.5 equiv.) added. The reaction mixture was heated at reflux overnight, cooled down to room temperature and concentrated under reduced pressure, and the residue purified by flash column chromatography (silica gel, petroleum benzine ramping to EtOAc unless otherwise stated) to give the desired ethanone.

General synthetic procedure B. To DMF-DMA (5.0-10.0 equiv.) was added an ethanone (1.0 equiv.). The reaction mixture was heated at reflux overnight, cooled down to room temperature and filtered to give the desired enaminone after washing with Et$_2$O.

General synthetic procedure C. To a suspension of a 2,4-dichloropyrimidine (1.00 equiv.) in PEG 400 (1.67 M in 2,4-dichloropyrimidine) were added 1-(vinyloxy)butane (3.00 equiv.), TEA (1.00 equiv.) and Pd(OAc)$_2$ (0.07 equiv.). The reaction mixture was degassed with N$_2$ for ten times, heated at 80° C. for 2 days, cooled down to room temperature, diluted with Et$_2$O and filtered through a pad of Celite®. The solids were washed with Et$_2$O, and the organic washing was collected, combined with the filtrate and washed with brine. The aqueous wash was extracted with Et$_2$O (3×), and the organic extracts were combined with the mixture of the organic washing and the filtrate, washed with brine and concentrated under reduced pressure. The residue was purified by flash column chromatography (silica gel, petroleum benzine ramping to petroleum benzine:DCM=2:8) to give the desired 4-(2-butoxyvinyl)pyrimidine.

General synthetic procedure D. To a solution of a 4-(2-butoxyvinyl)pyrimidine (1.00 equiv.) in a mixture of 1,4-dioxane and $H_2O$ (3:1, 150 nM in 4-(2-butoxyvinyl)pyrimidine) was added NBS (1.00 equiv.). The reaction mixture was stirred at room temperature for 1 h, and an aminopyridine (1.00 equiv.) added. The reaction mixture was heated at 85° C. for 4 h under $N_2$, cooled down to room temperature and concentrated under reduced pressure. The residue was suspended in EtOH, left at 4° C. overnight and filtered while cold. The solids were washed with ice-cold EtOH, dried and further washed with $H_2O$ to give a portion of the desired imidazo[1,2-a]pyridine. The organic and aqueous washings were combined and extracted with DCM (3×), and the organic extracts combined and concentrated under reduced pressure. The residue was purified by flash column chromatography (silica gel, petroleum benzine ramping to petroleum benzine:EtOAc=1:4 or DCM ramping to DCM:$CH_3OH$=100:3) to give a second portion of the desired imidazo[1,2-a]pyridine.

General synthetic procedure E. To a solution of 5-bromo-2-nitropyridine (1.0 equiv.) in DMSO (2.5 M in 5-bromo-2-nitropyridine) were added an azacycle (1.0-3.0 equiv.) and TEA (3.0 equiv.). The reaction mixture was heated at 120° C. overnight (unless otherwise stated), cooled down to room temperature and subjected to a workup as specified below to give the desired tertiary amine.

General synthetic procedure F. To a suspension of a nitro compound (1.00 equiv.) in $CH_3OH$ (50 mM in the nitro compound) was added 10% Pd/C (0.01 equiv.). The reaction mixture was bubbled with $H_2$ at room temperature for 30 min, stirred under $H_2$ overnight, and filtered through a pad of Celite®. The solids were washed with $CH_3OH$. The filtrate and washing were combined and concentrated under reduced pressure to give the desired primary amine; a further purification by flash column chromatography was not typically required unless otherwise stated.

General synthetic procedure G. To a solution of an amine (1.0 equiv.), N,N'-bis-Boc-S-methylisothiourea (1.1-1.5 equiv.) and TEA (3.5 equiv.) in DCM (100 mM in amine) on an ice bath was added $HgCl_2$ (1.1-2.0 equiv.). The reaction mixture was stirred on the ice bath for 30 min and at room temperature overnight, and filtered through a pad of Celite®. The solids were washed with DCM, and the washing was combined with the filtrate and concentrated under reduced pressure. The residue was purified by flash column chromatography (silica gel, DCM ramping to DCM:$CH_3OH$=94:6 unless otherwise stated) to give the desired Boc-protected guanidine.

General synthetic procedure H. Boc-protected guanidine (1.0 equiv.) was dissolved in a mixture of TFA (10 equiv.)/DCM/$H_2O$ (18:9:1). The reaction mixture was heated at 50° C. overnight and concentrated under reduced pressure to give the desired guanidine trifluoroacetate.

General synthetic procedure I. To a suspension of an enaminone (1.0 equiv.) in 2-methoxyethanol (0.25 M in enaminone) was added a guanidine (1.0-1.5 equiv.). In the event of a guanidine salt being used, NaOH (1.0-2.4 equiv.) was added. The reaction mixture was heated at 160-200° C. under microwave irradiation for 1 h, cooled down to room temperature and concentrated under reduced pressure. The residue was purified by FlashMaster Personal$^+$ chromatography or flash column chromatography (silica gel, DCM ramping to DCM:$CH_3OH$:32% $NH_3$ in $H_2O$=455:45:1), and washed with ice-cold $CH_3OH$ (unless otherwise stated) to afford the desired pyrimidine.

General synthetic procedure J. To a suspension of a halide (1.00 equiv.) in $CH_3CN$ (167 mM in halide) were added a boronic acid or boronate ester (0.90-2.00 equiv.), Pd(dppf)$Cl_2CH_2Cl_2$ or Ph(PPh$_3$)$_4$ (0.05 equiv.) and 0.5 M $Na_2CO_3$ (1.40 equiv.). The reaction mixture was heated at 120-140° C. under microwave irradiation for 1 h (unless otherwise stated). The reaction mixture was cooled down to room temperature, concentrated and partitioned between 10% $CH_3OH$ in DCM and distilled $H_2O$. The organic layer was separated and the aqueous layer extracted with 10% $CH_3OH$ in DCM (2×) The organic layer and extracts were combined and concentrated, and the residue was purified by flash column chromatography (silica gel, DCM ramping to DCM:$CH_3OH$=91:9 unless otherwise stated) to afford the desired adduct.

General Synthetic Procedure K. A suspension of a halide (1.00 equiv.), an amine (1.05-1.50 equiv.), $Cs_2CO_3$ (2.00 equiv.), Pd$_2$(dba)$_3$ or Pd(OAc)$_2$ (0.05 equiv.) and xantphos (0.05 equiv.) in 1,4-dioxane (100 mM in halide) was heated at 160-200° C. under microwave irradiation for 30-60 min. The reaction mixture was cooled down to room temperature, concentrated and partitioned between 10% $CH_3OH$ in DCM and distilled $H_2O$. The organic layer was separated and the aqueous layer extracted with 10% $CH_3OH$ in DCM (2×). The organic layer and extracts were combined and concentrated, and the residue was purified by flash column chromatography (silica gel, DCM ramping to DCM:$CH_3OH$ 93:7 unless otherwise stated) to afford the desired adduct.

General Synthetic Procedure L. To a suspension of an N-phenylsulfonylated (aza)indole (1.0 equiv.) in a mixture of THF and $CH_3OH$ (1:1, 25 mM in N-phenylsulfonylated (aza)indole) was added LiOH (5.0 equiv.). The reaction mixture was heated at 50° C. for 2 h, cooled down to room temperature and diluted with $H_2O$. The mixture was extracted with DCM (3×). The extracts were combined and concentrated under reduced pressure, and the residue was purified by flash column chromatography (silica gel, DCM ramping to DCM:$CH_3OH$:32% $NH_3$ in $H_2O$ 455:45:1) to afford the desired N-unsubstituted (aza)indole.

1-(Imidazo[1,2-a]pyridin-3-yl)ethan-1-one. 2-Aminopyridine (9.41 g, 100 mmol), DMF-DMA (21.2 mL, 160 mmol) and 1-chloroacetone (12.0 mL, 151 mmol) were subjected to general synthetic procedure A. A brown solid (7.16 g, 45%). $^1$H NMR (DMSO-d$_6$) δ 2.56 (s, 3H), 7.26 (td, 1H, J 7.0 & 1.0), 7.63 (ddd, 1H, J 9.0 & 7.0 & 1.5), 7.82 (d, 1H, J 9.0), 8.59 (s, 1H), 9.51 (dt, 1H, J 7.0 & 1.0).

1-(6-Bromoimidazo[1,2-a]pyridin-3-yl)ethan-1-one. 2-Amino-5-bromopyridine (17.3 g, 100 mmol), DMF-DMA (21.2 mL, 160 mmol) and 1-chloroacetone (12.0 mL, 151 mmol) were subjected to general synthetic procedure A. An orange solid with a purity of approximately 80% (8.80 g, 29%), which was used in the next step without further purification. $^1$H NMR (CDCl$_3$) δ 2.61 (s, 3H), 7.57 (dd, 1H, J 9.5 & 2.0), 7.66 (d, 1H, J 9.5), 8.31 (s, 1H), 9.83 (d, 1H, J 1.5).

1-(6-Fluoroimidazo[1,2-a]pyridin-3-yl)ethan-1-one. 2-Amino-5-fluoropyridine (11.3 g, 101 mmol), DMF-DMA (21.2 mL, 160 mmol) and 1-chloroacetone (12.0 mL, 151 mmol) were subjected to general synthetic procedure A. A brown solid with a purity of approximately 75% (5.94 g, 25%), which was used in the next step without further purification. ¹H NMR (CDCl₃) δ 2.61 (s, 3H), 7.42 (ddd, 1H, J 10.0 & 7.5 & 2.5), 7.74 (d, 1H, J 10.0 & 5.0), 8.35 (s, 1H), 9.65 (dd, 1H, J 9.5 & 2.5).

1-(6-(Trifluoromethyl)imidazo[1,2-a]pyridin-3-yl)ethan-1-one. 2-Amino-5-(trifluoromethyl)pyridine (16.3 g, 100 mmol), DMF-DMA (21.2 mL, 160 mmol) and 1-chloroacetone (12.0 mL, 151 mmol) were subjected to general synthetic procedure A. A brown solid with a purity of approximately 50% (8.00 g, 17%), which was used in the next step without further purification. ¹H NMR (CDCl₃) δ 2.65 (s, 3H), 7.65 (dd, 1H, J 9.5 & 1.5), 7.87 (d, 1H, J 9.5), 8.42 (s, 1H), 10.02-10.05 (m, 1H).

1-(6-Methylimidazo[1,2-a]pyridin-3-yl)ethan-1-one. 2-Amino-5-methylpyridine (10.9 g, 101 mmol), DMF-DMA (21.2 mL, 160 mmol) and 1-chloroacetone (12.0 mL, 151 mmol) were subjected to general synthetic procedure A. A light brown solid (5.36 g, 30%). ¹H NMR (DMSO-d₆) δ 2.39 (s, 3H), 2.55 (s, 3H), 7.50 (dd, 1H, J 9.0 & 2.0), 7.75 (d, 1H, J 9.0), 8.56 (s, 1H), 9.35-9.37 (m, 1H).

1-(6-Chloroimidazo[1,2-a]pyridin-3-yl)ethan-1-one. 2-Amino-5-chloropyridine (12.9 g, 100 mmol), DMF-DMA (21.2 mL, 160 mmol) and 1-chloroacetone (12.0 mL, 151 mmol) were subjected to general synthetic procedure A. A brown solid with a purity of approximately 82% (7.38 g, 31%), which was used in the next step without further purification. ¹H NMR (CDCl₃) δ 2.61 (s, 3H), 7.46 (dd, 1H, J 9.5 & 2.0), 7.70 (dd, 1H, J 9.5 & 0.5), 8.32 (s, 1H), 9.73 (dd, 1H, J 2.0 & 0.5).

1-(8-Fluoroimidazo[1,2-a]pyridin-3-yl)ethan-1-one. 2-Amino-3-fluoropyridine (11.3 g, 101 mmol), DMF-DMA (21.2 mL, 160 mmol) and 1-chloroacetone (12.0 mL, 151 mmol) were subjected to general synthetic procedure A. A brown solid with a purity of approximately 65% (9.18 g, 33%), which was used in the next step without further purification. ¹H NMR (CDCl₃) δ 2.63 (s, 3H), 7.01 (dt, 1H, J 7.5 & 4.5), 7.21 (ddd, 1H, J 9.0 & 8.0 & 1.0), 8.34 (s, 1H), 9.45 (dd, 1H, J 7.0 & 0.5).

1-(8-Bromoimidazo[1,2-a]pyridin-3-yl)ethan-1-one. 2-Amino-3-bromopyridine (17.3 g, 100 mmol), DMF-DMA (21.2 mL, 160 mmol) and 1-chloroacetone (12.0 mL, 151 mmol) were subjected to general synthetic procedure A. A brown solid with a purity of approximately 40% (10.1 g, 17%), which was used in the next step without further purification. ¹H NMR (CDCl₃) δ 2.62 (s, 3H), 6.96 (t, 1H, J 7.0), 7.75 (dd, 1H, J 7.5 & 1.0), 8.37 (s, 1H), 9.63 (dd, 1H, J 7.0 & 1.0).

1-(7-(Trifluoromethyl)imidazo[1,2-a]pyridin-3-yl)ethan-1-one. 2-Amino-4-(trifluoromethyl)pyridine (8.11 g, 50.0 mmol), DMF-DMA (10.7 mL, 80.5 mmol) and 1-chloroacetone (6.00 mL, 75.3 mmol) were subjected to general synthetic procedure A. A yellow solid with a purity of approximately 64% (3.98 g, 22%), which was used in the next step without further purification. ¹H NMR (CDCl₃) δ 2.65 (s, 3H), 7.25 (dd, 1H, J 7.0 & 1.5), 8.06 (s, 1H), 8.44 (s, 1H), 9.76 (d, 1H, J 7.0).

1-(2-Methylimidazo[1,2-a]pyridin-3-yl)ethan-1-one. To a solution of 2-aminopyridine (9.42 g, 100 mmol) in 1,2-dimethoxyethane (45 mL) were added sodium bicarbonate (8.40 g, 100 mmol) and 3-chloro-2,4-pentanedione (16.9 mL, 150 mmol). The reaction mixture was heated at reflux for 3 days, cooled down to room temperature and concentrated under reduced pressure, and the residue partitioned between distilled H₂O (300 mL) and DCM (150 mL). The organic layer was separated, and the aqueous layer was taken to pH 12 with 2 M NaOH and extracted with DCM (3×150 mL). The organic layer and DCM extracts were combined and concentrated under reduced pressure, and the residue was purified by flash column chromatography (silica gel, petroleum benzine ramping to EtOAc) to give 1-(2-methylimidazo[1,2-a]pyridin-3-yl)ethan-1-one as a light brown solid (15.2 g, 87%). ¹H NMR (CDCl₃) δ 2.62 (s, 3H), 2.80 (s, 3H), 7.01 (td, 1H, J 6.5 & 1.0), 7.45 (ddd, 1H, J 8.5 & 7.0 & 1.0), 7.64 (d, 1H, J 9.0), 9.74 (d, 1H, J 7.0).

1-(6-Iodoimidazo[1,2-a]pyridin-3-yl)ethan-1-one. 2-Amino-5-iodopyridine (22.0 g, 100 mmol), DMF-DMA (21.2 mL, 160 mmol) and 1-chloroacetone (12.0 mL, 151 mmol) were subjected to general synthetic procedure A. The residue was purified by flash column chromatography (silica gel, DCM ramping to 2% CH₃OH in DCM). A brown solid with a purity of approximately 80% (13.1 g, 37%), which was used in the next step without further purification. ¹H NMR (CDCl₃) δ 2.61 (s, 3H), 7.55 (d, 1H, J 9.5), 7.68 (dd, 1H, J 9.5 & 2.0), 8.26 (s, 1H), 9.93 (dd, 1H, J 1.0 & 0.5).

(E7)-3-(Dimethylamino)-1-(imidazo[1,2-a]pyridin-3-yl)prop-2-en-1-one. 1-(Imidazo[1,2-a]pyridin-3-yl)ethan-1-one (4.45 g, 27.8 mmol) and DMF-DMA (18.5 mL, 139 mmol) were reacted using general synthetic procedure B. A beige solid (5.42 g, 910%). ¹H NMR (CDCl₃) δ 2.99 (br s, 3H), 3.10 (br s, 3H), 5.67 (d, 1H, J 12.5), 7.16 (td, 1H, J 7.0 & 1.0), 7.36 (ddd, 1H, J 9.0 & 7.0 & 1.5), 7.68 (dt, 1H, J 9.0 & 1.0), 7.77 (d, 1H, J 12.5), 8.21 (s, 1H), 9.80 (dt, 1H, J 7.0 & 1.0).

(E)-1-(6-Bromoimidazo[1,2-a]pyridin-3-yl)-3-(dimethylamino)prop-2-en-1-one. 1-(6-Bromoimidazo[1,2-a]pyridin-3-yl)ethan-1-one (5.25 g, ~80% purity, 17.6 mmol) and DMF-DMA (16.7 mL, 126 mmol) were reacted using general synthetic procedure B. A light brown solid (4.98 g, 96%). ¹H NMR (CDCl₃) δ 2.95 (br s, 3H), 3.16 (br s, 3H), 5.64 (d, 1H, J 12.5), 7.42 (dd, 1H, J 9.5 & 1.5), 7.57 (d, 1H, J 9.5), 7.78 (d, 1H, J 12.5), 8.17 (s, 1H), 10.01 (d, 1H, J 1.5).

(E)-3-(Dimethylamino)-1-(6-fluoroimidazo[1,2-a]pyridin-3-yl)prop-2-en-1-one. 1-(6-Fluoroimidazo[1,2-a]pyridin-3-yl)ethan-1-one (5.94 g, ~75% purity, 25.0 mmol) and DMF-DMA (22.1 mL, 166 mmol) were reacted using general synthetic procedure B. A black solid (4.88 g, 84%). ¹H NMR (CDCl₃) δ 2.94 (br s, 3H), 3.14 (br s, 3H), 5.63 (d, 1H, J 12.5), 7.26 (ddd, 1H, J 10.0 & 7.5 & 2.5), 7.63 (dd, 1H, J 10.0 & 5.0), 7.76 (d, 1H, J 12.5), 8.20 (s, 1H), 9.80 (dd, 1H, J 5.0 & 2.5).

(E)-3-(Dimethylamino)-1-(6-(trifluoromethyl)imidazo[1,2-a]pyridin-3-yl)prop-2-en-1-one. 1-(6-(Trifluoromethyl)imidazo[1,2-a]pyridin-3-yl)ethan-1-one (8.00 g, ~50% purity, 17.5 mmol) and DMF-DMA (23.4 mL, 176 mmol) were reacted using general synthetic procedure B. A brown solid (4.90 g, 98%). ¹H NMR (CDCl₃) δ 2.97 (br s, 3H), 3.18 (br s, 3H), 5.66 (d, 1H, J 12.0), 7.59 (dd, 1H, J 9.0 & 1.5), 7.70 (d, 1H, J 9.0), 7.81 (d, 1H, J 12.5), 8.26 (s, 1H), 10.23-10.26 (m, 1H).

(E)-3-(Dimethylamino)-1-(6-methylimidazo[1,2-a]pyridin-3-yl)prop-2-en-1-one. 1-(6-Methylimidazo[1,2-a]pyridin-3-yl)ethan-1-one (4.69 g, 26.9 mmol) and DMF-DMA (17.9 mL, 135 mmol) were reacted using general synthetic procedure B. A brown solid (5.73 g, 93%). ¹H NMR (CDCl₃) δ 2.38 (d, 3H, J 0.5), 3.50 (app br s, 6H), 5.66 (d, 1H, J 12.5), 7.21 (dd, 1H, J 9.0 & 1.5), 7.58 (d, 1H, J 9.0), 7.75 (d, 1H, J 12.0), 8.16 (s, 1H), 9.63-9.65 (m, 1H).

(E)-1-(6-Chloroimidazo[1,2-a]pyridin-3-yl)-3-(dimethylamino)prop-2-en-1-one. 1-(6-Chloroimidazo[1,2-a]pyridin-3-yl)ethan-1-one (7.38 g, ~82% purity, 31.1 mmol) and DMF-DMA (25.2 mL, 190 mmol) were reacted using general synthetic procedure B. A brown solid (6.28 g, 81%). ¹H NMR (CDCl₃) δ 2.96 (br s, 3H), 3.16 (br s, 3H), 5.64 (d, 1H, J 12.5), 7.32 (dd, 1H, J 9.5 & 2.0), 7.62 (dd, 1H, J 9.5 & 1.0), 7.78 (d, 1H, J 12.5), 8.19 (s, 1H), 9.91 (dd, 1H, J 2.0 & 1.0).

(E)-3-(Dimethylamino)-1-(8-fluoroimidazo[1,2-a]pyridin-3-yl)prop-2-en-1-one. 1-(8-Fluoroimidazo[1,2-a]pyridin-3-yl)ethan-1-one (9.18 g, ~65% purity, 33.5 mmol) and DMF-DMA (22.3 mL, 168 mmol) were reacted using general synthetic procedure B. A brown solid (7.01 g, 90%). $^1$H NMR (CDCl$_3$) δ 2.94 (br s, 3H), 3.15 (br s, 3H), 5.65 (d, 1H, J 13.0), 6.87 (dd, 1H, J 7.5 & 5.0), 7.05 (ddd, 1H, J 10.0 & 7.5 & 1.0), 7.77 (d, 1H, J 12.5), 8.18 (s, 1H), 9.59 (dd, 1H, J 7.0 & 1.0).

(E)-1-(8-Bromoimidazo[1,2-a]pyridin-3-yl)-3-(dimethylamino)prop-2-en-1-one. 1-(8-Bromoimidazo[1,2-a]pyridin-3-yl)ethan-1-one (10.1 g, ~40% purity, 16.9 mmol) and DMF-DMA (11.2 mL, 84.3 mmol) were reacted using general synthetic procedure B. A brown solid (3.82 g, 77%). $^1$H NMR (CDCl$_3$) δ 2.96 (br s, 3H), 3.15 (br s, 3H), 5.64 (d, 1H, J 12.5), 6.84 (t, 1H, J 7.0), 7.60 (d, 1H, J 7.5), 7.77 (d, 1H, J 12.5), 8.21 (s, 1H), 9.79 (d, 1H, J 7.0).

(E)-3-(Dimethylamino)-1-(7-(trifluoromethyl)imidazo[1,2-a]pyridin-3-yl)prop-2-en-1-one. 1-(7-(Trifluoromethyl)imidazo[1,2-a]pyridin-3-yl)ethan-1-one (3.98 g, ~64% purity, 11.2 mmol) and DMF-DMA (7.50 mL, 56.4 mmol) were reacted using general synthetic procedure B. A gold solid (3.14 g, 99%). $^1$H NMR (CDCl$_3$) δ 2.97 (br s, 3H), 3.18 (br s, 3H), 5.67 (d, 1H, J 12.5), 7.13 (dd, 1H, J 7.5 & 1.5), 7.81 (d, 1H, J 12.0), 7.98 (app s, 1H), 8.29 (s, 1H), 9.92 (d, 1H, J 7.5).

(E)-3-(Dimethylamino)-1-(2-methylimidazo[1,2-a]pyridin-3-yl)prop-2-en-1-one. 1-(2-Methylimidazo[1,2-a]pyridin-3-yl)ethan-1-one (8.71 g, 50.0 mmol) and DMF-DMA (33.2 mL, 250 mmol) were reacted using general synthetic procedure B. A brown solid (9.95 g, 87%). $^1$H NMR (CDCl$_3$) δ 2.76 (s, 3H), 2.97 (br s, 3H), 3.11 (br s, 3H), 5.56 (d, 1H, J 12.5), 6.88 (t, 1H, J 6.5), 7.29 (dd, 1H, J 8.5 & 2.0), 7.55 (d, 1H, J 9.0), 7.78 (d, 1H, J 12.0), 9.65 (d, 1H, J 6.5).

(E)-3-(Dimethylamino)-1-(6-iodoimidazo[1,2-a]pyridin-3-yl)prop-2-en-1-one. 1-(6-Iodoimidazo[1,2-a]pyridin-3-yl)ethan-1-one (10.8 g, 80% purity, 30.2 mmol) and DMF-DMA (20.1 mL, 151 mmol) were reacted using general synthetic procedure B. A dark brown solid (9.41 g, 91%). $^1$H NMR (CDCl$_3$) δ 2.95 (br s, 3H), 3.15 (br s, 3H), 5.63 (d, 1H, J 12.0), 7.45 (dd, 1H, J 9.5 & 0.5), 7.52 (dd, 1H, J 9.5 & 1.5), 7.77 (d, 1H, J 12.0), 8.11 (s, 1H), 10.10 (dd, 1H, J 1.5 & 0.5).

(E)-4-(2-Butoxyvinyl)-2-chloro-5-fluoropyrimidine. 2,4-Dichloro-5-fluoropyrimidine (16.7 g, 100 mmol) and 1-(vinyloxy)butane (38.8 mL, 300 mmol) were coupled using general synthetic procedure C. A pale yellow oil (14.8 g, 64%). $^1$H NMR (CDCl$_3$) δ 0.96 (t, 3H, J 7.5), 1.41-1.49 (m, 2H), 1.69-1.77 (m, 2H), 4.00 (t, 2H, J 6.5), 5.90 (dd, 1H, J 12.5 & 0.5), 8.00 (d, 1H, J 12.5), 8.21 (d, 1H, J 2.0).

(E)-4-(2-Butoxyvinyl)-2-chloro-5-methylpyrimidine. 2,4-Dichloro-5-methylpyrimidine (16.3 g, 100 mmol) and 1-(vinyloxy)butane (38.8 mL, 300 mmol) were coupled using general synthetic procedure C. A brown sticky solid (6.81 g, 30%). $^1$H NMR (CDCl$_3$) δ 0.95 (t, 3H, J 7.5), 1.39-1.48 (m, 2H), 1.67-1.75 (m, 2H), 2.16 (s, 3H), 3.99 (t, 2H, J 6.5), 5.79 (dd, 1H, J 12.0 & 1.5), 7.96 (d, 1H, J 12.0), 8.14 (s, 1H).

3-(2-Chloro-5-fluoropyrimidin-4-yl)imidazo[1,2-a]pyridine. (E)-4-(2-Butoxyvinyl)-2-chloro-5-fluoropyrimidine (8.07 g, 35.0 mmol), NBS (6.23 g, 35.0 mmol) and 2-aminopyridine (3.29 g, 35.0 mmol) were subjected to general synthetic procedure D. A beige solid (3.49 g, 40%). $^1$H NMR (DMSO-d$_6$) δ 7.36 (t, 1H, J 7.0), 7.66 (ddd, 1H, J 8.5 & 7.0 & 1.0), 7.88 (d, 1H, J 8.5), 8.53 (d, 1H, J 4.0), 8.84 (d, 1H, J 3.5), 9.76 (d, 1H, J 7.0).

3-(2-Chloro-5-fluoropyrimidin-4-yl)-6-fluoroimidazo[1,2-a]pyridine. (E)-4-(2-Butoxyvinyl)-2-chloro-5-fluoropyrimidine (2.21 g, 9.58 mmol), NBS (1.71 g, 9.61 mmol) and 2-amino-5-fluoropyridine (1.08 g, 9.63 mmol) were subjected to general synthetic procedure D. A grey solid (2.00 g, 78%). $^1$H NMR (DMSO-d$_6$) δ 7.76 (ddd, 1H, J 10.0 & 7.5 & 2.5), 7.96 (dd, 1H, J 10.0 & 5.5), 8.54 (d, 1H, J 4.0), 8.88 (d, 1H, J 3.5), 9.75 (dd, 1H, J 5.5 & 2.5).

3-(2-Chloro-5-fluoropyrimidin-4-yl)-6-bromoimidazo[1,2-a]pyridine. (E)-4-(2-Butoxyvinyl)-2-chloro-5-fluoropyrimidine (5.55 g, 24.1 mmol), NBS (4.29 g, 24.1 mmol) and 2-amino-5-bromopyridine (4.17 g, 24.1 mmol) were subjected to general synthetic procedure D. A beige solid (2.05 g, 26%). $^1$H NMR (CDCl$_3$) δ 7.63 (d, 1H, J 9.5), 7.78 (d, 1H, J 9.5), 8.51 (d, 1H, J 3.0), 8.58 (d, 1H, J 3.5), 10.18 (s, 1H).

3-(2-Chloro-5-fluoropyrimidin-4-yl)-6-phenylimidazo[1,2-a]pyridine. Prepared by reaction of 3-(2-Chloro-5-fluoropyrimidin-4-yl)-6-bromoimidazo[1,2-a]pyridine (988 mg, 3.02 mmol) with phenylboronic acid (331 mg, 2.71 mmol) using general synthetic procedure J. A white solid (480 mg, 54%). $^1$H NMR (DMSO-d$_6$) δ 7.55-7.62 (m, 3H), 7.76 (d, 2H, J 7.5), 7.99 (app s, 1), 8.00 (d, 1H, J 2.0), 8.57 (d, 11, J 4.0), 8.89 (d, 1H, J 3.5), 10.11 (s, 1H).

3-(2-Chloro-5-fluoropyrimidin-4-yl)-6-methylimidazo[1,2-a]pyridine. (E)-4-(2-Butoxyvinyl)-2-chloro-5-fluoropyrimidine (2.21 g, 9.58 mmol), NBS (1.71 g, 9.61 mmol) and 2-amino-5-methylpyridine (1.04 g, 9.61 mmol) were subjected to general synthetic procedure D. A grey solid (1.81 g, 72%). $^1$H NMR (DMSO-d$_6$) δ 2.46 (s, 3H), 7.74 (dd, 1H, J 9.0 & 1.5), 7.89 (d, 1H, J 9.0), 8.68 (d, 1H, J 3.5), 8.93 (d, 1H, J 3.0), 9.59 (s, 1H).

3-(2-Chloro-5-fluoropyrimidin-4-yl)-6-(trifluoromethyl)imidazo[1,2-a]pyridine. (E)-4-(2-Butoxyvinyl)-2-chloro-5-fluoropyrimidine (2.21 g, 9.58 mmol), NBS (1.71 g, 9.61 mmol) and 2-amino-5-(trifluoromethyl)pyridine (1.55 g, 9.56 mmol) were subjected to general synthetic procedure D. A beige solid (1.79 g, 59%). $^1$H NMR (DMSO-d$_6$) δ 7.90 (dd, 1H, J 9.5 & 1.5), 8.08 (d, 1H, J 9.5), 8.64 (d, 1H, J 3.5), 8.94 (d, 1H, J 3.5), 10.21 (s, 1H).

3-(2-Chloro-5-methylpyrimidin-4-yl)imidazo[1,2-a]pyridine. (E)-4-(2-Butoxyvinyl)-2-chloro-5-methylpyrimidine (4.53 g, 20.0 mmol), NBS (3.56 g, 20.0 mmol) and 2-aminopyridine (1.88 g, 20.0 mmol) were subjected to general synthetic procedure D. A beige solid (2.54 g, 50%). $^1$H NMR (DMSO-d$_6$) δ 2.52 (s, 3H), 7.24 (t, 1H, J 7.0), 7.57 (t, 1H, J 8.0), 7.82 (d, 1H, J 9.0), 8.44 (s, 1H), 8.67 (s, 1H), 9.59 (d, 1H, J 7.0).

Tert-butyl 4-(6-nitropyridin-3-yl)piperazine-1-carboxylate. 5-Bromo-2-nitropyridine (4.06 g, 20.0 mmol) and tert-butyl piperazine-1-carboxylate (4.47 g, 24.0 mmol) were subjected to general synthetic procedure E. The reaction mixture was heated at 70° C. for 3 days, diluted with a mixture of H$_2$O (20 mL) and EtOAc (20 mL), cooled down to room temperature and left at 4° C. overnight. The precipitates thus formed were filtered and washed with H$_2$O (20 mL) to give tert-butyl 4-(6-nitropyridin-3-yl)piperazine-1-carboxylate as a yellow solid (5.70 g, 92%). $^1$H NMR (CDCl$_3$) δ 1.46 (s, 9H), 3.44 (t, 4H, J 5.0), 3.62 (t, 4H, J 5.0), 7.19 (dd, 1H, J 9.5 & 3.0), 8.10 (d, 1H, J 3.0), 8.14 (d, 1H, J 9.0).

1-Methyl-4-(6-nitropyridin-3-yl)piperazine. 5-Bromo-2-nitropyridine (10.2 g, 50.2 mmol) and 1-methylpiperazine (6.66 mL, 60.0 mmol) were subjected to general synthetic procedure E. The reaction mixture was concentrated under reduced pressure, and the residue triturated with EtOAc (60 mL) and filtered (filtrate A). The solids were washed with EtOAc (100 mL), dried and dissolved in H$_2$O (100 mL). The solution was taken to pH 11-12 with saturated aqueous Na$_2$CO$_3$ solution, and the precipitates thus formed were filtered (filtrate B) to give a portion of 1-methyl-4-(6-nitropyridin-3-yl)piperazine as a dark brown solid (4.44 g). Filtrates A and B were combined and extracted with DCM (3×100 mL). The organic extracts were combined, dried over $Na_2SO_4$ and concentrated under reduced pressure. The residue was crystallised with EtOAc to give a second portion of 1-methyl-4-(6-nitropyridin-3-yl)piperazine as dark brown crystals (3.66 g). A total yield: 8.10 g, 72%. $^1$H NMR ($CDCl_3$) δ 2.35 (s, 3H), 2.56 (t, 4H, J 5.0), 3.45 (t, 4H, J 5.0), 7.18 (dd, 1H, J 9.0 & 3.0), 8.11 (d, 1H, J 3.0), 8.14 (d, 1H, J 9.5).

1-Ethyl-4-(6-nitropyridin-3-yl)piperazine. 5-Bromo-2-nitropyridine (7.76 g, 38.2 mmol) and 1-ethylpiperazine (4.58 g, 40.1 mmol) were subjected to general synthetic procedure E. The reaction mixture was heated at 90° C. overnight, cooled down to room temperature, concentrated under reduced pressure, and the residue triturated with EtOAc (60 mL) and filtered. The solids were washed with EtOAc (100 mL), dried and purified by flash column chromatography (silica gel, DCM ramping to $DCM:CH_3OH$=9:1) to give 1-ethyl-4-(6-nitropyridin-3-yl)piperazine as an orange solid (6.79 g, 75%). $^1$H NMR ($CDCl_3$) δ 1.14 (t, 3H, J 7.0), 2.49 (q, 2H, J 7.0), 2.62 (t, 4H, J 5.0), 3.48 (t, 4H, J 5.0), 7.19 (dd, 1H, J 9.0 & 3.0), 8.13 (d, 1H, J 3.0), 8.16 (d, 1H, J 9.0).

1-(4-(6-Nitropyridin-3-yl)piperazin-1-yl)ethan-1-one. 5-Bromo-2-nitropyridine (5.00 g, 24.6 mmol) and 1-(piperazin-1-yl)ethan-1-one (5.00 g, 39.0 mmol) were subjected to general synthetic procedure E. The reaction mixture was diluted with EtOAc (50 mL), and the precipitates thus formed were filtered and washed with EtOAc (10 mL) and $H_2O$ (30 mL) to give a portion of 1-(4-(6-nitropyridin-3-yl)piperazin-1-yl)ethan-1-one as a yellow solid (2.77 g). The filtrate and washings were combined and extracted with DCM (3×100 mL). The organic extracts were combined, dried over $Na_2SO_4$ and concentrated under reduced pressure. The residue was purified by FlashMaster Personal$^+$ chromatography (silica gel, DCM ramping to $DCM:CH_3OH$=94:6) to give a second portion of 1-(4-(6-nitropyridin-3-yl)piperazin-1-yl)ethan-1-one as a yellow solid (2.89 g). A total yield: 5.66 g, 92%. $^1$H NMR ($CDCl_3$) δ 2.16 (s, 3H), 3.47 (t, 2H, J 5.5), 3.52 (t, 2H, J 5.5), 3.71 (t, 2H, J 5.5), 3.83 (t, 2H, J 5.5), 7.22 (dd, 1H, J 9.0 & 3.0), 8.13 (d, 1H, J 3.0), 8.17 (d, 1H, J 9.0).

1-(Methylsulfonyl)-4-(6-nitropyridin-3-yl)piperazine. 5-Bromo-2-nitropyridine (2.03 g, 10.0 mmol) and 1-(methanesulfonyl)piperazine (1.97 g, 12.0 mmol) were subjected to general synthetic procedure E. The reaction mixture was left at 4° C. overnight and filtered, and the solids were washed with $H_2O$ (50 mL), dried and purified by flash column chromatography (silica gel, DCM ramping to $DCM:CH_3OH$ 95:5) to give 1-(methylsulfonyl)-4-(6-nitropyridin-3-yl)piperazine as a yellow solid (2.29 g, 80%). $^1$H NMR ($CDCl_3$) δ 2.93 (s, 3H), 3.26 (t, 4H, J 5.0), 3.64 (t, 4H, J 5.0), 7.54 (dd, 1H, J 9.5 & 2.5), 8.20 (d, 1H, J 9.5), 9.30 (d, 1H, J 2.5).

4-(6-Nitropyridin-3-yl)morpholine. 5-Bromo-2-nitropyridine (2.00 g, 9.85 mmol) and morpholine (1.30 mL, 14.9 mmol) were subjected to general synthetic procedure E. The reaction mixture was concentrated under reduced pressure, and the residue triturated with EtOAc (75 mL) and filtered to give 4-(6-nitropyridin-3-yl)morpholine as a yellow solid (2.06 g, 100%). $^1$H NMR ($CDCl_3$) δ 3.41 (t, 4H, J5.0), 3.89 (t, 4H, J 5.0), 7.22 (dd, 1H, J 9.0 & 3.0), 8.13 (d, 1H, J 3.0), 8.18 (d, 1H, J 9.0).

2-Nitro-5-(piperidin-1-yl)pyridine. 5-Bromo-2-nitropyridine (5.07 g, 25.0 mmol) and piperidine (7.40 mL, 74.9 mmol) were subjected to general synthetic procedure E. The reaction mixture was heated at 120° C. for 2 days, cooled down to room temperature and concentrated under reduced pressure, and the residue triturated with EtOAc (300 mL), filtered and washed with EtOAc (200 mL). The filtrate and washing were combined and concentrated under reduced pressure, and the residue was triturated with $H_2O$ (400 mL) and filtered. The solids were washed with $H_2O$ (100 ML), dried and purified by flash column chromatography (silica gel, DCM ramping to $DCM:CH_3OH$ 98:2) to give 2-nitro-5-(piperidin-1-yl)pyridine as a yellow solid (4.06 g, 78%). $^1$H NMR ($CDCl_3$) δ 1.69 (app s, 6H), 3.45 (t, 4H, J 5.0), 7.13 (dd, 1H, J 9.0 & 2.5), 8.07 (d, 1H, J 2.5), 8.10 (d, 1H, J 9.0).

N,N-Dimethyl-1-(6-nitropyridin-3-yl)piperidin-4-amine. 5-Bromo-2-nitropyridine (2.03 g, 10.0 mmol) and N,N-dimethylpiperidin-4-amine (1.58 g, 12.3 mmol) were subjected to general synthetic procedure E. The reaction mixture was concentrated under reduced pressure, and the residue triturated with EtOAc (100 mL) and filtered. The solids were washed with EtOAc (100 mL), dried and purified by flash column chromatography (silica gel, DCM ramping to $DCM:CH_3OH$=9:1) to give N,N-dimethyl-1-(6-nitropyridin-3-yl)piperidin-4-amine as a yellow solid (2.07 g, 83%). $^1$H NMR ($CDCl_3$) δ 1.64 (d, 2H, J 12.0), 2.00 (d, 2H, J 13.0), 2.33 (s, 6H), 2.40-2.48 (m, 1H), 3.05 (t, 2H, J 12.0), 3.97 (d, 2H, J 13.0), 7.19 (d, 1H, J 9.0), 8.12-8.17 (m, 2H).

1-(6-Nitropyridin-3-yl)-1,4-diazepane. 5-Bromo-2-nitropyridine (10.2 g, 50.2 mmol) and homopiperazine (5.03 g, 50.2 mmol) were subjected to general synthetic procedure E. The reaction mixture was concentrated under reduced pressure, and the residue dissolved in saturated aqueous $Na_2CO_3$ solution (100 mL). The resultant solution was taken to pH 14 with 2 M NaOH and extracted with DCM (6×100 mL). The organic extracts were combined and concentrated under reduced pressure to give 1-(6-nitropyridin-3-yl)-1,4-diazepane as an orange solid (5.67 g, 51%). $^1$H NMR ($CDCl_3$) δ 1.90-1.96 (m, 2H), 2.85 (t, 2H, J 6.0), 3.07 (t, 2H, J 5.5), 3.64 (t, 2H, J 5.5), 3.71 (t, 2H, J 6.0), 7.01 (dd, 1H, J 9.5 & 3.0), 7.98 (d, 1H, J 3.0), 8.14 (d, 1H, J 9.0) (one proton signal (NH) not observed).

1-(4-(6-Nitropyridin-3-yl)-1,4-diazepan-1-yl)ethan-1-one. To a solution of 1-(6-nitropyridin-3-yl)-1,4-diazepane (3.33 g, 15.0 mmol) and TEA (2.09 mL, 15.0 mmol) in $CHCl_3$ (50 mL) on an ice bath was added acetyl chloride (2.13 mL, 30.0 mmol) dropwise. The reaction mixture was stirred at room temperature for 72 h and concentrated under reduced pressure. The residue was purified by flash column chromatography (silica gel, DCM ramping to $DCM:CH_3OH$=95:5) to give 1-(4-(6-nitropyridin-3-yl)-1,4-diazepan-1-yl)ethan-1-one as a yellow solid (3.47 g, 88%). $^1$H NMR ($CDCl_3$) (Compound exists as two rotamers in approximately 4.5:5.5 ratio. Major rotamer is designated as $^\#$ and minor rotamer as *) δ 1.94-1.98 (m, 2H), 1.98* (s, 1.35H), 2.02$^\#$ (s, 1.65H), 3.42$^\#$ (t, 1.1H, J 6.5), 3.43* (t, 0.9H, J 6.5), 3.61-3.66$^{\#,*,*}$ (m, 2.9H), 3.69$^\#$ (t, 1.1H, J 6.0), 3.75$^\#$ (t, 1.1H, J 5.5), 3.76* (t, 0.9H, J 5.5), 7.02$^\#$ (dd, 0.55H, J 9.0 & 3.0), 7.03* (dd, 0.45H, J 8.5 & 3.0), 7.92$^\#$ (d, 0.55H, J 3.0), 7.93* (d, 0.45H, J 3.0), 8.06$^\#$ (d, 0.55H, J9.5), 8.08* (d, 0.45H, J 9.0).

Tert-butyl 4-(6-aminopyridin-3-yl)piperazine-1-carboxylate. Tert-butyl 4-(6-nitropyridin-3-yl)piperazine-1-carboxylate (4.78 g, 15.5 mmol) was reduced according to general synthetic procedure F. A brown solid (3.99 g, 92%). $^1$H NMR ($CDCl_3$) δ 1.46 (s, 9H), 2.93 (app s, 4H), 3.55 (t, 4H, J 5.0), 4.24 (br s, 2H), 6.47 (d, 1H, J 9.0), 7.15 (dd, 1H, J 9.0 & 2.5), 7.75 (d, 1H, J 2.5).

5-(4-Methylpiperazin-1-yl)pyridin-2-amine. 1-Methyl-4-(6-nitropyridin-3-yl)piperazine (4.44 g, 20.0 mmol) was reduced according to general synthetic procedure F. A grey solid (3.84 g, 100%). $^1$H NMR (CDCl$_3$) δ 2.33 (s, 3H), 2.56 (t, 4H, J 5.0), 3.05 (t, 4H, J 5.0), 4.17 (br s, 2H), 6.47 (d, 1H, J 19.0), 7.16 (dd, 1H, J 8.5 & 3.0), 7.77 (d, 1H, J 2.5).

5-(4-Ethylpiperazin-1-yl)pyridin-2-amine. 1-Ethyl-4-(6-nitropyridin-3-yl)piperazine (6.79 g, 28.7 mmol) was reduced according to general synthetic procedure F, and the residue was purified by flash column chromatography (silica gel, DCM ramping to DCM:CH$_3$OH:32% NH$_3$ in H$_2$O 450:50:1). A purple solid (4.87 g, 82%). $^1$H NMR (CDCl$_3$) δ 1.11 (t, 3H, J 7.5), 2.47 (q, 2H, J 7.5), 2.60 (t, 4H, J 4.5), 3.06 (t, 4H, J 4.5), 4.17 (br s, 2H), 6.47 (d, 1H, J 8.5), 7.17 (dd, 1H, J 8.5 & 2.0), 7.77 (d, 1H, J 2.0).

1-(4-(6-Aminopyridin-3-yl)piperazin-1-yl)ethan-1-one. 1-(4-(6-Nitropyridin-3-yl)piperazin-1-yl)ethan-1-one (700 mg, 2.80 mmol) was reduced according to general synthetic procedure F. A purple solid (616 mg, 100%). $^1$H NMR (CDCl$_3$) δ 2.13 (s, 3H), 2.97 (t, 2H, J 5.0), 3.01 (t, 2H, J 5.0), 3.60 (t, 2H, J 5.0), 3.76 (t, 2H, J 5.0), 4.22 (br s, 2H), 6.49 (d, 1H, J 8.5), 7.17 (dd, 1H, J 8.5 & 3.0), 7.78 (d, 1H, J 3.0).

5-(4-(Methylsulfonyl)piperazin-1-yl)pyridin-2-amine. 1-(Methylsulfonyl)-4-(6-nitropyridin-3-yl)piperazine (1.31 g, 4.58 mmol) was reduced according to general synthetic procedure F. A yellow solid (1.17 g, 100%). $^1$H NMR (CDCl$_3$) δ 2.83 (s, 3H), 3.11 (t, 4H, J 5.0), 3.38 (t, 4H, J 5.0), 4.24 (s, 2H), 6.49 (d, 1H, J 8.5), 7.17 (dd, 1H, J 8.5 & 2.5), 7.79 (d, 1H, J 2.5).

5-Morpholinopyridin-2-amine. 4-(6-Nitropyridin-3-yl)morpholine (4.60 g, 22.0 mmol) was reduced according to general synthetic procedure F. A white solid (3.94 g, 100%). $^1$H NMR (CDCl$_3$) δ 2.99 (t, 4H, J 4.5), 3.83 (t, 4H, J 4.5), 4.23 (br s, 2H), 6.47 (d, 1H, J 9.0), 7.13 (dd, 1H, J 9.0 & 3.0), 7.75 (d, 1H, J 2.5).

5-(Piperidin-1-yl)pyridin-2-amine. 2-Nitro-5-(piperidin-1-yl)pyridine (3.70 g, 17.8 mmol) was reduced according to general synthetic procedure F. A white solid (3.10 g, 98%). $^1$H NMR (CDCl$_3$) δ 1.52-1.54 (m, 2H), 1.69-1.73 (m, 4H), 2.97 (t, 4H, J 5.5), 4.15 (s, 2H), 6.47 (d, 1H, J 9.0), 7.18 (dd, 1H, J 9.0 & 3.0), 7.77 (d, 1H, J 3.0).

5-(4-(Dimethylamino)piperidin-1-yl)pyridin-2-amine. N,N-Dimethyl-1-(6-nitropyridin-3-yl)piperidin-4-amine (2.00 g, 7.99 mmol) was reduced according to general synthetic procedure F. A white solid (1.66 g, 94%), which was used in the next step without further purification and characterisation.

1-(4-(6-Aminopyridin-3-yl)-1,4-diazepan-1-yl)ethan-1-one. 1-(4-(6-Nitropyridin-3-yl)-1,4-diazepan-1-yl)ethan-1-one (3.47 g, 13.1 mmol) was reduced according to general synthetic procedure F. A brownish solid (3.08 g, 100%). $^1$H NMR (CDCl$_3$) (Compound exists as two rotamers in approximately 4.5:5.5 ratio. Major rotamer is designated as $^\#$ and minor rotamer as *) δ 1.90-1.96 (m, 2H), 1.98* (s, 1.35H), 2.06$^\#$ (s, 1.65H), 3.35$^\#$ (t, 1.1H, J 6.0), 3.40* (t, 0.9H, J 6.0), 3.41-3.45$^{\#,*}$ (m, 2H), 3.46$^\#$ (t, 1.1H, J 6.0), 3.50-3.53* (m, 0.9H), 3.55-3.59* (m, 0.9H), 3.68-3.71$^\#$ (m, 1.1H), 6.45$^{\#,*}$ (d, 0.45H, J 9.0; d, 0.55H J 9.0), 6.94$^\#$ (app t, 0.55H, J 8.5), 6.95* (app t, 0.45H, J 8.5), 7.59* (d, 0.45H, J 2.0), 7.60$^\#$ (d, 0.55H, J 2.5) (two proton signals (NH$_2$) not observed).

2-(2,3-Bis(tert-butoxycarbonyl)guanidino)pyridine. In the presence of HgCl$_2$ (10.4 g, 38.3 mmol), pyridin-2-anine (2.78 g, 29.5 mmol) and N,N'-bis-Boc-S-methylisothiourea (11.2 g, 38.6 mmol) were reacted using general synthetic procedure G, and the residue was purified by flash column chromatography (silica gel, petroleum benzine ramping to petroleum benzine:EtOAc=9:1) and further crystallised with DCM and hexane. A white solid (4.18 g, 42%). $^1$H NMR (CDCl$_3$) δ 1.52 (s, 18H), 7.01 (dd, 1H, J 7.0 & 5.0), 7.70 (t, 1H, J 7.0), 8.29 (d, 1H, J 4.0), 8.37 (app br s, 1H), 10.89 (br s, 1H), 11.53 (br s, 1H).

2-(2,3-Bis(tert-butoxycarbonyl)guanidino)pyrazine. In the presence of HgCl$_2$ (1.63 g, 6.00 mmol), pyrazin-2-amine (476 mg, 5.00 mmol) and N,N'-bis-Boc-S-methylisothiourea (1.75 g, 6.03 mmol) were reacted using general synthetic procedure G, and the residue was purified by flash column chromatography (silica gel, petroleum benzine ramping to petroleum benzine:EtOAc=6:4). A beige solid (1.25 g, 74%). $^1$H NMR (CDCl$_3$) δ 1.50 (s, 9H), 1.52 (s, 9H), 8.26 (s, 1H), 8.32 (s, 1H), 9.74 (s, 1H), 10.85 (br s, 1H), 11.49 (br s, 1H).

2-(2,3-Bis(tert-butoxycarbonyl)guanidino)-5-fluoropyridine. In the presence of HgCl$_2$ (5.97 g, 22.0 mmol), 5-fluoropyridin-2-amine (2.24 g, 20.0 mmol) and N,N'-bis-Boc-S-methylisothiourea (6.38 g, 22.0 mmol) were reacted using general synthetic procedure G, and the residue was purified by flash column chromatography (silica gel, petroleum benzine ramping to petroleum benzine:DCM 1:9). A white solid (4.83 g, 68%). $^1$H NMR (CDCl$_3$) δ 1.52 (s, 9H), 1.54 (s, 9H), 7.44 (td, 1H, J 8.0 & 2.0), 8.15 (d, 1H, J 2.0), 8.42 (d, 1H, J 5.5), 10.90 (br s, 1H), 11.51 (s, 1H).

2-(2,3-Bis(tert-butoxycarbonyl)guanidino)-5-chloropyridine. In the presence of HgCl$_2$ (5.97 g, 22.0 mmol), 5-chloropyridin-2-amine (2.57 g, 20.0 mmol) and N,N'-bis-Boc-S-methylisothiourea (6.39 g, 22.0 mmol) were reacted using general synthetic procedure G, and the residue was purified by flash column chromatography (silica gel, petroleum benzine ramping to petroleum benzine:DCM=1:9). A white solid (3.25 g, 44%). $^1$H NMR (CDCl$_3$) δ 1.53 (s, 9H), 1.54 (s, 9H), 7.67 (d, 1H, J 9.0), 8.24 (s, 1H), 8.39 (d, 1H, J 8.5), 10.92 (br s, 1H), 11.51 (s, 1H).

2-(2,3-Bis(tert-butoxycarbonyl)guanidino)-5-bromopyridine. In the presence of HgCl$_2$ (17.7 g, 65.2 mmol), 5-bromopyridin-2-amine (8.65 g, 50.0 mmol) and N,N'-bis-Boc-S-methylisothiourea (18.9 g, 65.1 mmol) were reacted using general synthetic procedure G, and the residue was purified by flash column chromatography (silica gel, petroleum benzine ramping to petroleum benzine:DCM=1:9). A white solid (8.32 g, 40%). $^1$H NMR (CDCl$_3$) δ 1.53 (s, 9H), 1.54 (s, 9H), 7.80 (dd, 1H, J 9.0 & 2.0), 8.34 (d, 1H, J 2.0), 8.35 (d, 1H, J 9.0), 10.91 (br s, 1H), 11.50 (s, 1H).

2-(2,3-Bis(tert-butoxycarbonyl)guanidino)-5-iodopyridine. In the presence of HgCl$_2$ (5.97 g, 22.0 mmol), 5-iodopyridin-2-amine (4.40 g, 20.0 mmol) and N,N'-bis-Boc-S-methylisothiourea (6.39 g, 22.0 mmol) were reacted using general synthetic procedure G, and the residue was purified by flash column chromatography (silica gel, petroleum benzine ramping to petroleum benzine:DCM 1:9). A white solid (3.37 g, 36%). $^1$H NMR (CDCl$_3$) δ 1.52 (s, 9H), 1.53 (s, 9H), 7.96 (d, 1H, J 9.0), 8.25 (d, 1H, J8.0), 8.48 (s, 1H), 10.88 (br s, 1H), 11.50 (s, 1H).

2-(2,3-Bis(tert-butoxycarbonyl)guanidino)-5-methylpyridine. In the presence of HgCl$_2$ (5.97 g, 22.0 mmol), 5-methylpyridin-2-amine (2.16 g, 20.0 mmol) and N,N'-bis-Boc-S-methylisothiourea (6.39 g, 22.0 mmol) were reacted using general synthetic procedure G, and the residue was purified by flash column chromatography (silica gel, petroleum benzine ramping through DCM to DCM:CH$_3$OH=97:3). A white solid (3.03 g, 43%). $^1$H NMR (CDCl$_3$) δ 1.52 (s, 9H), 1.53 (s, 9H), 2.28 (s, 3H), 7.51 (d, 1H, J 8.5), 8.11 (s, 1H), 8.24 (br s, 1H), 10.81 (br s, 1H), 11.53 (s, 1H).

Tert-butyl 4-(6-(2,3-bis(tert-butoxycarbonyl)guanidino)pyridin-3-yl)piperazine-1-carboxylate. In the presence of HgCl₂ (4.79 g, 17.6 mmol), tert-butyl 4-(6-aminopyridin-3-yl)piperazine-1-carboxylate (3.78 g, 13.6 mmol) and N,N'-bis-Boc-S-methylisothiourea (5.13 g, 17.7 mmol) were reacted using general synthetic procedure G. A white solid (4.25 g, 60%). ¹H NMR (CDCl₃) δ 1.48 (s, 9H), 1.52 (s, 18H), 3.09 (t, 4H, J 4.5), 3.58 (t, 4H, J 5.0), 7.28 (dd, 1H, J 9.0 & 30.0), 7.96 (d, 1H, J 3.0), 8.22 (app br s, 1H), 10.75 (br s, 1H), 11.51 (br s, 1H).

1-Methyl-4-(6-(2,3-bis(tert-butoxycarbonyl)guanidino)pyridin-3-yl)piperazine. In the presence of HgCl₂ (11.6 g, 42.7 mmol), 5-(4-methylpiperazin-1-yl)pyridin-2-amine (5.49 g, 28.6 mmol) and N,N'-bis-Boc-S-methylisothiourea (12.4 g, 42.7 mmol) were reacted using general synthetic procedure G. A beige solid (8.06 g, 65%). ¹H NMR (CDCl₃) δ 1.51 (s, 18H), 2.34 (s, 3H), 2.57 (t, 4H, J 5.0), 3.17 (t, 4H, J 5.0), 7.26 (dd, 1H, J 8.5 & 3.0), 7.96 (d, 1H, J 2.5), 8.20 (br d, 1H, J 8.0), 10.70 (br s, 1H), 11.51 (br s, 1H).

1-Ethyl-4-(6-(2,3-bis(tert-butoxycarbonyl)guanidino)pyridin-3-yl)piperazine. In the presence of HgCl₂ (5.13 g, 18.9 mmol), 5-(4-ethylpiperazin-1-yl)pyridin-2-amine (3.00 g, 14.5 mmol) and N,N'-bis-Boc-S-methylisothiourea (5.49 g, 18.9 mmol) were reacted using general synthetic procedure G. A greenish foam (6.27 g, 96%). ¹H NMR (CDCl₃) δ 1.14 (t, 3H, J 7.0), 1.52 (s, 9H), 1.53 (s, 9H), 2.51 (q, 2H, J 7.0), 2.64 (t, 4H, J 4.5), 3.21 (t, 4H, J 4.5), 7.28 (dd, 1H, J 9.0 & 2.5), 7.98 (s, 1H), 8.18 (d, 1H, J 6.5), 10.72 (s, 11H), 11.52 (s, 1H).

1-Acetyl-4-(6-(2,3-bis(tert-butoxycarbonyl)guanidino)pyridin-3-yl)piperazine. In the presence of HgCl₂ (5.45 g, 20.1 mmol), 1-(4-(6-aminopyridin-3-yl)piperazin-1-yl)ethan-1-one (2.21 g, 10.0 mmol) and N,N'-bis-Boc-S-methylisothiourea (3.50 g, 12.0 mmol) were reacted using general synthetic procedure G. A white solid (3.82 g, 82%). ¹H NMR (CDCl₃) δ 1.55 (s, 9H), 1.56 (s, 9H), 2.15 (s, 3H), 3.19 (t, 2H, J 5.0), 3.25 (t, 2H, J 5.0), 3.64 (t, 2H, J 5.0), 3.78 (t, 2H, J 5.0), 7.08 (d, 1H, J 8.5), 7.32 (dd, 1H, J 9.0 & 3.0), 8.03 (d, 1H, J 3.0), 11.27 (br s, 1H), 11.74 (br s, 1H).

1-(Methylsulfonyl)-4-(6-(2,3-bis(tert-butoxycarbonyl)guanidino)pyridin-3-yl)piperazine. In the presence of HgCl₂ (1.53 g, 5.64 mmol), 5-(4-(methylsulfonyl)piperazin-1-yl)pyridin-2-amine (1.11 g, 4.33 mmol) and N,N'-bis-Boc-S-methylisothiourea (1.64 g, 5.65 mmol) were reacted using general synthetic procedure G, and the residue was purified by flash column chromatography (silica gel, petroleum benzine ramping to petroleum benzine:EtOAc=3:7). A yellow solid (1.83 g, 85%). ¹H NMR (CDCl₃) δ 1.50 (s, 9H), 1.51 (s, 9H), 2.81 (s, 3H), 3.24 (t, 4H, J 4.0), 3.37 (t, 4H, J 4.0), 7.27 (dd, 1H, J 9.0 & 2.5), 7.96 (s, 1H), 8.24 (br d, 1H, J 6.5), 10.7 (br s, 1H), 11.50 (br s, 1H).

4-(6-(2,3-Bis(tert-butoxycarbonyl)guanidino)pyridin-3-yl)morpholine. In the presence of HgCl₂ (7.58 g, 27.9 mmol), 5-morpholinopyridin-2-amine (3.85 g, 21.5 mmol) and N,N'-bis-Boc-S-methylisothiourea (8.11 g, 27.9 mmol) were reacted using general synthetic procedure G, and the residue was purified by flash column chromatography (silica gel, petroleum benzine ramping to petroleum benzine:E-tOAc=7:3). A yellowish solid (5.53 g, 61%). ¹H NMR (CDCl₃) δ 1.45 (s, 9H), 1.47 (s, 9H), 3.06 (t, 4H, J 4.5), 3.79 (t, 4H, J 4.5), 7.20 (dd, 1H, J 9.0 & 3.0), 7.90 (d, 1H, J 2.5), 8.18 (br d, 1H, J 8.0), 10.66 (br s, 1H), 11.48 (br s, 1H).

1-(6-(2,3-Bis(tert-butoxycarbonyl)guanidino)pyridin-3-yl)piperidine. In the presence of HgCl₂ (9.50 g, 35.0 mmol), 5-(piperidin-1-yl)pyridin-2-amine (3.10 g, 17.5 mmol) and N,N'-bis-Boc-S-methylisothiourea (7.60 g, 26.2 mmol) were reacted using general synthetic procedure G, and the residue was purified (silica gel, petroleum benzine ramping to petroleum benzine:EtOAc 8:2). A yellow solid (4.00 g, 54%). ¹H NMR (CDCl₃) δ 1.50 (s, 9H), 1.52 (s, 9H), 1.56-1.58 (m, 2H), 1.70 (t, 4H, J 5.5), 3.11 (t, 4H, J 5.5), 7.26 (dd, 1H, J 9.0 & 3.0), 7.96 (d, 1H, J 3.0), 8.17 (d, 1H, J 8.0), 10.68 (br s, 1H), 11.51 (br s, 1H).

1-Acetyl-4-(6-(2,3-bis(tert-butoxycarbonyl)guanidino)pyridin-3-yl)-1,4-diazepane. In the presence of HgCl₂ (7.14 g, 26.3 mmol), 1-(4-(6-aminopyridin-3-yl)-1,4-diazepan-1-yl)ethan-1-one (3.08 g, 13.1 mmol) and N,N'-bis-Boc-S-methylisothiourea (5.72 g, 19.7 mmol) were reacted using general synthetic procedure G. A yellow foam (4.51 g, 72%). ¹H NMR (CDCl₃) (Compound exists as two rotamers in approximately 4.5:5.5 ratio. Major rotamer is designated as # and minor rotamer as *) δ 1.50 (s), 1.51 (s), 1.52 (s) (total 18H), 1.96-2.02 (m, 2H), 2.03* (s, 1.35H), 2.10# (s, 1.65H), 3.34# (t, 1.1H, J 6.0), 3.42* (t, 0.9H, J 6.0), 3.51-3.63#,#,*,*,* (m, 4.9H), 3.74# (t, 1.1H, J 5.0), 7.06# (d, 0.55H, J 9.5), 7.07* (dd, 0.45H, J 9.5 & 1.0), 7.80 (s, 1H), 8.16# (d, 0.55H, J 9.0), 8.19* (d, 0.45H, J 9.5), 10.644 (br s, 0.55H), 10.66* (br s, 0.45H), 11.51 (br s, 1H).

1-(Pyridin-2-yl)guanidine 2,2,2-trifluoroacetate. 2-(2,3-Bis(tert-butoxycarbonyl)guanidino)pyridine (3.60 g, 10.7 mmol) was de-protected using general synthetic procedure H. A white solid (2.65 g, 99%). ¹H NMR (CD₃OD) δ 7.04 (dt, 1H, J 7.5 & 0.5), 7.18 (ddd, 1H, J 7.5 & 5.0 & 1.0), 7.85 (ddd, 1H, J 9.5 & 7.5 & 2.0), 8.34 (ddd, 1H, J 5.0 & 2.0 & 1.0).

1-(Pyrazin-2-yl)guanidine 2,2,2-trifluoroacetate. 2-(2,3-Bis(tert-butoxycarbonyl)guanidino)pyrazine (1.18 g, 3.50 mmol) was de-protected using general synthetic procedure H to give a mixture of 1-(pyrazin-2-yl)guanidine 2,2,2-trifluoroacetate and its tert-butylated byproduct in a ratio of approximately 1:4.2 as a yellowish solid (1.19 g, 26%), which was directly used in the next step without further purification. ¹H NMR (CD₃OD) δ 8.35 (s, 1H), 8.38 (d, 1H, J 1.5), 8.43 (s, 1H).

1-(5-Fluoropyridin-2-yl)guanidine 2,2,2-trifluoroacetate. 2-(2,3-Bis(tert-butoxycarbonyl)guanidino)-5-fluoropyridine (4.34 g, 12.2 mmol) was de-protected using general synthetic procedure H. A yellow solid (3.28 g, 100%). ¹H NMR (CD₃OD) δ 7.11 (dd, 1H, J 9.0 & 3.5), 7.72 (td, 1H, J 9.0 & 3.0), 8.25 (d, 1H, J 3.0).

1-(5-Chloropyridin-2-yl)guanidine 2,2,2-trifluoroacetate. 2-(2,3-Bis(tert-butoxycarbonyl) guanidino)-5-chloropyridine (3.15 g, 8.49 mmol) was de-protected using general synthetic procedure H. A white solid (2.42 g, 100%). ¹H NMR (CD₃OD) δ 7.07 (d, 1H, J 9.0), 7.89 (d, 1H, J 8.5), 8.34 (s, 1H).

1-(5-Bromopyridin-2-yl)guanidine 2,2,2-trifluoroacetate. 2-(2,3-Bis(tert-butoxycarbonyl) guanidino)-5-bromopyridine (3.70 g, 8.91 mmol) was de-protected using general synthetic procedure H. A white solid (2.93 g, 99%). ¹H NMR (CD₃OD) δ 7.02 (d, 1H, J 8.5), 8.01 (d, 1H, J 9.0), 8.43 (s, 1H).

1-(5-Iodopyridin-2-yl)guanidine 2,2,2-trifluoroacetate. 2-(2,3-Bis(tert-butoxycarbonyl) guanidino)-5-iodopyridine (3.24 g, 7.01 mmol) was de-protected using general synthetic procedure H. A white solid (2.64 g, 100%). ¹H NMR (CD₃OD) δ 6.91 (d, 1H, J 8.5), 8.14 (d, 1H, J 8.5), 8.56 (s, 1H).

1-(5-Methylpyridin-2-yl)guanidine 2,2,2-trifluoroacetate. 2-(2,3-Bis(tert-butoxycarbonyl)guanidino)-5-methylpyridine (2.81 g, 8.02 mmol) was de-protected using general synthetic procedure H. A grey solid (2.12 g, 100%). ¹H NMR (CD₃OD) a 2.32 (s, 3H), 6.94 (d, 1H, J 8.0), 7.69 (d, 1H, J 8.5), 8.17 (s, 1H).

1-(5-(Piperazin-1-yl)pyridin-2-yl)guanidine di(2,2,2-trifluoroacetate). Tert-butyl 4-(6-(2,3-bis(tert-butoxycarbonyl)

guanidino)pyridin-3-yl)piperazine-1-carboxylate (781 mg, 1.50 mmol) was de-protected using general synthetic procedure H. A yellow solid (672 mg, 100%). $^1$H NMR (CD$_3$OD) δ 3.38-3.45 (m, 8H), 7.02 (d, 1H, J 9.0), 7.60 (dd, 1H, J 9.0 & 3.0), 8.06 (d, 1H, J 3.0).

1-(5-(4-Methylpiperazin-1-yl)pyridin-2-yl)guanidine. 1-Methyl-4-(6-(2,3-bis(tert-butoxycarbonyl)guanidino)pyridin-3-yl)piperazine (1.55 g, 3.57 mmol) was de-protected using general synthetic procedure H. The residue was dissolved CH$_3$OH (50 mL), and a suspension of excess Ambersep® 900 resin (hydroxide form, pre-swelled with H$_2$O for 30 min and CH$_3$OH for 30 min) in CH$_3$OH (50 mL) added. The resultant suspension was stirred at room temperature overnight and filtered, and the solids were washed with CH$_3$OH (50 mL). The organic washing was combined with the filtrate and concentrated under reduced pressure to give 1-(5-(4-methylpiperazin-1-yl)pyridin-2-yl)guanidine as a yellow solid (836 mg, 100%). $^1$H NMR (CD$_3$OD) δ 2.34 (s, 3H), 2.61 (t, 4H, J 5.0), 3.11 (t, 4H, J 5.0), 6.74 (d, 1H, J 9.0), 7.32 (dd, 1H, J 9.0 & 3.0), 7.85 (d, 1H, J 3.0).

1-(5-(4-ethylpiperazin-1-yl)pyridin-2-yl)guanidine 2,2,2-trifluoroacetate. 1-Ethyl-4-(6-(2,3-bis(tert-butoxycarbonyl)guanidino)pyridin-3-yl)piperazine (6.27 g, 14.0 mmol) was de-protected using general synthetic procedure H. A yellow foam (6.66 g, 100%). $^1$H NMR (CD$_3$OD) δ 1.31 (t, 3H, J 7.5), 3.14 (t, 2H, J 12.5), 3.21 (q, 2H, J 7.5), 3.23 (t, 2H, J 12.5), 3.69 (d, 2H, J 11.5), 3.85 (d, 2H, J 12.5), 7.02 (d, 1H, J 9.0), 7.60 (d, 1H, J 9.0 & 2.5), 8.06 (d, 1H, J 2.0).

1-(5-(4-Acetylpiperazin-1-yl)pyridin-2-yl)guanidine 2,2,2-trifluoroacetate. 1-Acetyl-4-(6-(2,3-bis(tert-butoxycarbonyl)guanidino)pyridin-3-yl)piperazine (693 mg, 1.50 mmol) was de-protected using general synthetic procedure H. A yellow solid (564 mg, 100%). $^1$H NMR (CD$_3$OD) δ2.15 (s, 3H), 3.18 (t, 2H, J 5.0), 3.24 (t, 2H, J 5.0), 3.71 (t, 2H, J 5.0), 3.75 (t, 2H, J 5.0), 6.96 (d, 1H, J 9.0), 7.57 (dd, 1H, J 9.0 & 3.0), 8.03 (d, 1H, J 2.5).

1-(5-(4-(Methylsulfonyl)piperazin-1-yl)pyridin-2-yl)guanidine 2,2,2-trifluoroacetate. 1-(Methylsulfonyl)-4-(6-(2,3-bis(tert-butoxycarbonyl)guanidino)pyridin-3-yl)piperazine (618 mg, 1.24 mmol) was de-protected using general synthetic procedure H. A yellow solid (511 mg, 100%). $^1$H NMR (CD$_3$OD) δ 2.90 (s, 3H), 3.30 (t, 4H, J 4.5), 3.39 (t, 4H, J 4.5), 6.97 (d, 1H, J 9.0), 7.58 (dd, 1H, J 9.0 & 2.0), 8.04 (d, 1H, J 2.0).

1-(5-Morpholinopyridin-2-yl)guanidine. 4-(6-(2,3-Bis(tert-butoxycarbonyl)guanidino)pyridin-3-yl)morpholine (1.43 g, 3.39 mmol) was de-protected using general synthetic procedure H. The residue was dissolved CH$_3$OH (50 mL), and a suspension of excess Ambersep® 900 resin (hydroxide form, pre-swelled with H$_2$O for 30 min and CH$_3$OH for 30 min) in CH$_3$OH (25 mL) was added. The resultant suspension was stirred at room temperature overnight and filtered, and the solids were washed with CH$_3$OH (100 mL). The organic washing was combined with the filtrate and concentrated under reduced pressure to give 1-(5-morpholinopyridin-2-yl)guanidine as a yellowish solid (751 mg, 100%). $^1$H NMR (CD$_3$OD) δ 3.16 (t, 4H, J 5.0), 3.84 (t, 4H, J 5.0), 6.96 (d, 1H, J 9.0), 7.52 (dd, 1H, J 9.0 & 3.0), 7.99 (d, 1H, J 2.5).

1-(5-(Piperidin-1-yl)pyridin-2-yl)guanidine 2,2,2-trifluoroacetate. 1-(6-(2,3-Bis(tert-butoxycarbonyl)guanidino)pyridin-3-yl)piperidine (4.00 g, 9.54 mmol) was de-protected using general synthetic procedure H. A white solid (3.18 g, 100%). $^1$H NMR (CD$_3$OD) δ 1.69-1.78 (m, 2H), 1.90-2.20 (m, 4H), 3.52 (t, 4H, J 5.5), 7.18 (d, 1H, J 9.5), 8.00 (dd, 1H, J 9.5 & 2.5), 8.46 (d, 1H, J 2.5).

1-(5-(4-Acetyl-1,4-diazepan-1-yl)pyridin-2-yl)guanidine 2,2,2-trifluoroacetate. 1-Acetyl-4-(6-(2,3-bis(tert-butoxycarbonyl)guanidino)pyridin-3-yl)-1,4-diazepane (572 mg, 1.20 mmol) was de-protected using general synthetic procedure H. A yellow glue (468 mg, 100%). $^1$H NMR (DMSO-d$_6$) δ 1.71-1.79 (m, 1H), 1.79-1.89 (m, 1H), 1.83 (s, 1.5H), 1.95 (s, 1.5H), 3.30 (t, 1H, J 6.0), 3.36 (t, 1H, J 6.0), 3.40-3.63 (m, 5H), 3.67 (t, 1H, J 5.5), 6.90 (d, 0.5H, J 9.0), 6.92 (d, 0.5H, J 9.0), 7.34 (dd, 0.5H, J 9.0 & 3.0), 7.37 (dd, 0.5H, J 9.0 & 3.0), 7.79 (d, 0.5H, J 3.0), 7.81 (d, 0.5H, J 3.0), 8.15 (br s, 4H), 10.72 (s, 0.5H), 10.74 (s, 0.5H).

Examples 4-(Imidazo[1,2-a]pyridin-3-yl)-N-(5-(piperazin-1-yl)pyridin-2-yl)pyrimidin-2-amine (1). Prepared by reaction of 1-(5-(piperazin-1-yl)pyridin-2-yl)guanidine di(2,2,2-trifluoroacetate) (495 mg, 1.10 mmol) with (E)-3-(dimethylamino)-1-(imidazo[1,2-a]pyridin-3-yl)prop-2-en-1-one (216 mg, 1.00 mmol) using general synthetic procedure I. A yellow solid (120 mg, 32%). $^1$H NMR (DMSO-d$_6$) δ 2.89 (t, 4H, J 5.0), 3.07 (t, 4H, J 5.0), 7.11 (td, 1H, J 7.0 & 1.0), 7.41 (d, 1H, J 5.5), 7.43 (dd, 1H, J 9.0 & 3.0), 7.50 (ddd, 1H, J 9.0 & 7.0 & 1.0), 7.75 (d, 1H, J 8.5), 8.00 (d, 1H, J 9.0), 8.03 (d, 1H, J 3.0), 8.43 (d, 1H, J5.5), 8.62 (s, 1H), 9.99 (s, 1H), 10.38 (d, 1H, J 7.0). HRMS m/z 373.1886 [M+H]$^+$.

4-(Imidazo[1,2-a]pyridin-3-yl)-N-(5-(4-methylpiperazin-1-yl)pyridin-2-yl)pyrimidin-2-amine (2). Prepared by reaction of 1-(5-(4-methylpiperazin-1-yl)pyridin-2-yl)guanidine (282 mg, 1.20 mmol) with (E)-3-(dimethylamino)-1-(imidazo[1,2-a]pyridin-3-yl)prop-2-en-1-one (216 mg, 1.00 mmol) using general synthetic procedure I. A yellow solid (170 mg, 44%). $^1$H NMR (DMSO-d$_6$) δ 2.22 (s, 3H), 2.47 (t, 4H, J 5.0), 3.13 (t, 4H, J 5.0), 7.11 (td, 1H, J 6.5 & 1.0), 7.41 (d, 1H, J 5.0), 7.44 (dd, 1H, J 9.5 & 3.0), 7.50 (ddd, 1H, J 9.0 & 7.0 & 1.5), 7.75 (d, 1H, J 9.0), 8.00 (d, 1H, J 9.0), 8.04 (d, 1H, J 3.0), 8.43 (d, 1H, J 5.0), 8.61 (s, 1H), 10.00 (s, 1H), 10.38 (d, 1H, J 7.0). HRMS m/z 387.2047 [M+H]$^+$.

1-(4-(6-((4-(Imidazo[1,2-a]pyridin-3-yl)pyrimidin-2-yl)amino)pyridin-3-yl)piperazin-1-yl)ethan-1-one (3). Prepared by reaction of 1-(5-(4-acetylpiperazin-1-yl)pyridin-2-yl)guanidine 2,2,2-trifluoroacetate (564 mg, 1.50 mmol) with (E)-3-(dimethylamino)-1-(imidazo[1,2-a]pyridin-3-yl)prop-2-en-1-one (216 mg, 1.00 mmol) using general synthetic procedure I. A yellow solid (240 mg, 58%). $^1$H NMR (DMSO-d$_6$) δ 2.05 (s, 3H), 3.08 (t, 2H, J 5.0), 3.15 (t, 2H, J 5.0), 3.60 (t, 2H, J 5.5), 3.61 (t, 2H, J 5.5), 7.12 (td, 1H, J 7.0 & 1.0), 7.42 (d, 1H, J 5.5), 7.48 (dd, 1H, J 9.0 & 3.0), 7.50 (ddd, 1H, J 9.0 & 7.0 & 1.0), 7.75 (d, 1H, J 9.0), 8.03 (d, 1H, J 9.0), 8.08 (d, 1H, J 13.0), 8.44 (d, 1H, J 5.5), 8.62 (s, 1H), 10.04 (s, 1H), 10.39 (d, 1H, J 7.0). HRMS m/z 415.1989 [M+H]$^+$.

4-(Imidazo[1,2-a]pyridin-3-yl)-N-(5-morpholinopyridin-2-yl)pyrimidin-2-amine (4). Prepared by reaction of 1-(5-morpholinopyridin-2-yl)guanidine (221 mg, 957 μmol) with (E)-3-(dimethylamino)-1-(imidazo[1,2-a]pyridin-3-yl)prop-2-en-1-one (172 mg, 799 μmol) using general synthetic procedure I. A straw solid (140 mg, 47%). $^1$H NMR (DMSO-d$_6$) δ 3.10 (t, 4H, J 5.0), 3.75 (t, 4H, J 5.0), 7.12 (td, 1H, J 7.0 & 1.0), 7.39 (d, 1H, J 5.5), 7.44 (dd, 1H, J 9.5 & 3.0), 7.51 (ddd, 1H, J 9.0 & 6.5 & 1.0), 7.74 (d, 1H, J 9.0), 7.97 (d, 1H, J 9.0), 8.04 (d, 1H, J 3.0), 8.42 (d, 1H, J 5.5), 8.58 (s, 1H), 9.91 (s, 1H), 10.32 (d, 1H, J 7.0). HRMS m/z 374.1728 [M+H]$^+$.

4-(Imidazo[1,2-a]pyridin-3-yl)-N-(5-(piperidin-1-yl)pyridin-2-yl)pyrimidin-2-amine (5). Prepared by reaction of 1-(5-(piperidin-1-yl)pyridin-2-yl)guanidine 2,2,2-trifluoroacetate (320 mg, 960 µmol) with (E)-3-(dimethylamino)-1-(imidazo[1,2-a]pyridin-3-yl)prop-2-en-1-one (172 mg, 799 µmol) using general synthetic procedure I. A yellow solid (50 mg, 17%). $^1$H NMR (DMSO-d$_6$) δ 1.48-1.54 (m, 2H), 1.59-1.65 (m, 4H), 3.09 (t, 4H, 15.5), 7.11 (td, 1H, J 7.0 & 1.0), 7.37 (d, 1H, J 5.5), 7.42 (dd, 1H, J 9.0 & 3.0), 7.51 (ddd, 1H, J 8.0 & 6.5 & 1.0), 7.72 (d, 1H, J 9.0), 7.88 (d, 1H, J 9.0), 8.01 (d, 1H, J 3.0), 8.40 (d, 1H, J 5.5), 8.54 (s, 1H), 9.78 (s, 1H), 10.26 (d, 1H, J 7.0). HRMS m/z 372.1934 [M+H]$^+$.

1-(4-(6-((4-(Imidazo[1,2-a]pyridin-3-yl)pyrimidin-2-yl)amino)pyridin-3-yl)-1,4-diazepan-1-yl)ethan-1-one (6). Prepared by reaction of 1-(5-(4-acetyl-1,4-diazepan-1-yl)pyridin-2-yl)guanidine 2,2,2-trifluoroacetate (468 mg, 1.20 mmol) with (E)-3-(dimethylamino)-1-(imidazo[1,2-a]pyridin-3-yl)prop-2-en-1-one (216 mg, 1.00 mmol) using general synthetic procedure I. A yellow solid (195 mg, 45%). $^1$H NMR (DMSO-d$_6$) δ 1.78-1.83 (m, 1H), 1.84 (s, 1.5H), 1.85-1.90 (m, 1H), 1.97 (s, 1.5H), 3.34 (t, 1H, J 6.0), 3.38 (t, 1H, J 6.0), 3.46-3.74 (m, 6H), 7.10 (td, 1H, J 7.0 & 1.0), 7.22-7.28 (m, 1H), 7.35 (d, 1H, J 5.5), 7.49 (ddd, 1H, J 8.0 & 7.0 & 1.0), 7.73 (d, 1H, J 9.0), 7.85 (d, 0.5H, 110.0), 7.87 (d, 0.5H, J 10.5), 7.89 (d, 0.5H, J 4.5), 7.90 (d, 0.5H, J 3.5), 8.39 (d, 1H, J 5.5), 8.56 (s, 0.5H), 8.57 (s, 0.5H), 9.73 (s, 0.5H), 9.74 (s, 0.5H), 10.29 (d, 1H, J 6.5). HRMS m/z 429.2148 [M+H]$^+$.

4-(Imidazo[1,2-a]pyridin-3-yl)-N-(pyridin-2-yl)pyrimidin-2-amine (7). Prepared by reaction of 1-(pyridin-2-yl)guanidine 2,2,2-trifluoroacetate (240 mg, 959 µmol) with (E)-3-(dimethylamino)-1-(imidazo[1,2-a]pyridin-3-yl)prop-2-en-1-one (172 mg, 799 µmol) using general synthetic procedure I. A beige solid (115 mg, 50%). $^1$H NMR (DMSO-d$_6$) δ 7.02 (ddd, 1H, J 7.5 & 5.0 &1.0), 7.14 (dt, 1H, J 7.0 & 1.5), 7.45 (d, 1H, J 5.5), 7.52 (ddd, 1H, 19.0 & 7.0 & 1.5), 7.73 (td, 1H, J 9.0 & 1.0), 7.76 (ddd, 1H, J 9.0 & 7.5 & 2.0), 8.08 (d, 1H, J 8.5), 8.32 (ddd, 1H, J 5.0 & 2.0 & 0.5), 8.46 (d, 1H, J 5.5), 8.56 (s, 1H), 10.06 (s, 1H), 10.32 (td, 1H, J 7.0 & 1.0). HRMS m/z 289.1201 [M+H]$^+$.

1-(4-(6-((4-(6-Fluoroimidazo[1,2-a]pyridin-3-yl)pyrimidin-2-yl)amino)pyridin-3-yl)piperazin-1-yl)ethan-1-one (8). Prepared by reaction of 1-(5-(4-acetylpiperazin-1-yl)pyridin-2-yl)guanidine 2,2,2-trifluoroacetate (452 mg, 1.20 mmol) with (E)-3-(dimethylamino)-1-(6-fluoroimidazo[1,2-a]pyridin-3-yl)prop-2-en-1-one (234 mg, 1.00 mmol) using general synthetic procedure I. A beige solid (220 mg, 51%). $^1$H NMR (DMSO-d$_6$) δ2.05 (s, 3H), 3.08 (t, 2H, J 5.0), 3.15 (t, 2H, J 5.0), 3.60 (t, 2H, J 4.0), 3.61 (t, 2H, 14.0), 7.43 (d, 1H, J 5.5), 7.48 (dd, 1H, J 9.0 & 3.0), 7.58 (ddd, 1H, J 10.0 & 8.0 & 2.5), 7.82 (dd, 1H, J 10.0 & 5.5), 7.91 (br d, 1H, J 6.5), 8.09 (d, 1H, J 3.0), 8.46 (d, 1H, J 5.0), 8.67 (s, 1H), 10.25 (br s, 1H), 10.59 (dd, 1H, J 5.5 & 2.0). HRMS m/z 433.1895 [M+H]$^+$.

1-(4-(6-((4-(6-Chloroimidazo[1,2-a]pyridin-3-yl)pyrimidin-2-yl)amino)pyridin-3-yl)piperazin-1-yl)ethan-1-one (9). Prepared by reaction of 1-(5-(4-acetylpiperazin-1-yl)pyridin-2-yl)guanidine 2,2,2-trifluoroacetate (452 mg, 1.20 mmol) with (E)-3-(dimethylamino)-1-(6-chloroimidazo-[1,2-a]pyridin-3-yl)prop-2-en-1-one (250 mg, 1.00 mmol) using general synthetic procedure I. A yellow solid (291 mg, 65%). $^1$H NMR (DMSO-d$_6$) δ 2.05 (s, 3H), 3.08 (t, 2H, J 5.0), 3.15 (t, 2H, J 5.0), 3.59 (t, 2H, J 4.0), 3.60 (t, 2H, J 4.0), 7.43 (d, 1H, J 5.5), 7.48 (dd, 1H, J 9.0 & 3.0), 7.53 (dd, 1H, J 9.5 & 2.0), 7.79 (dd, 1H, J 9.5 & 0.5), 7.88 (br d, 1H, J 8.0), 8.12 (d, 1H, J 3.0), 8.46 (d, 1H, J 5.5), 8.66 (s, 1H), 10.20 (br s, 1H), 10.34 (d, 1H, J 2.0). HRMS m/z 449.1604 [M($^{35}$Cl)+H]$^+$, 451.1571 [M($^{37}$Cl)+H]$^+$.

1-(4-(6-((4-(6-Bromoimidazo[1,2-a]pyridin-3-yl)pyrimidin-2-yl)amino)pyridin-3-yl)piperazin-1-yl)ethan-1-one (10). Prepared by reaction of 1-(5-(4-acetylpiperazin-1-yl)pyridin-2-yl)guanidine 2,2,2-trifluoroacetate (452 mg, 1.20 mmol) with (E)-3-(dimethylamino)-1-(6-bromoimidazo[1,2-a]pyridin-3-yl)prop-2-en-1-one (295 mg, 1.00 mmol) using general synthetic procedure I. A yellow solid (351 mg, 71%). $^1$H NMR (DMSO-d$_6$) δ 2.04 (s, 3H), 3.07 (t, 2H, J 5.0), 3.13 (t, 2H, J 5.0), 3.55-3.60 (m, 4H), 7.39 (d, 1H, J 5.5), 7.47 (dd, 1H, J 9.0 & 3.0), 7.60 (dd, 1H, J 9.5 & 2.0), 7.70 (d, 1H, J 9.5), 7.76 (br d, 1H, J 8.0), 8.11 (d, 1H, J 3.0), 8.42 (d, 1H, J 5.5), 8.55 (s, 1H), 9.92 (s, 1H), 10.21 (s, 1H). HRMS m/z 493.1091 [M(79Br)+H]$^+$, 495.1075 [M($^1$Br)+H]$^+$.

1-(4-(6-((4-(6-(Trifluoromethyl)imidazo[1,2-a]pyridin-3-yl)pyrimidin-2-yl)amino)pyridin-3-yl)piperazin-1-yl)ethan-1-one (11). Prepared by reaction of 1-(5-(4-acetylpiperazin-1-yl)pyridin-2-yl)guanidine 2,2,2-trifluoroacetate (452 mg, 1.20 mmol) with (E)-3-(dimethylamino)-1-(6-(trifluoromethyl)imidazo[1,2-a]pyridin-3-yl)prop-2-en-1-one (284 mg, 1.00 mmol) using general synthetic procedure I. A yellow solid (306 mg, 63%). $^1$H NMR (DMSO-d$_6$) δ 2.05 (s, 3H), 3.08 (t, 2H, J 5.0), 3.14 (t, 2H, J 5.0), 3.55-3.65 (m, 4H), 7.42 (dd, 1H, J 9.0 & 3.0), 7.47 (d, 1H, J 5.5), 7.70 (dd, 1H, J 9.5 & 2.0), 7.89 (d, 1H, J 9.0), 7.96 (br d, 1H, J 9.5), 8.07 (d, 1H, J 3.0), 8.51 (d, 1H, J 5.0), 8.75 (s, 1H), 10.06 (s, 1H), 10.34 (s, 1H). HRMS m/z 483.1865 [M+H]$^+$.

1-(4-(6-((4-(6-(Furan-2-yl)imidazo[1,2-a]pyridin-3-yl)pyrimidin-2-yl)amino)pyridin-3-yl)piperazin-1-yl)ethan-1-one (12). Prepared by reaction of 10 (247 mg, 501 µmol) with furan-2-ylboronic acid (67.3 mg, 601 µmol) using general synthetic procedure J. A yellow solid (195 mg, 810%). $^1$H NMR (DMSO-d$_6$) δ 2.05 (s, 3H), 3.03 (t, 2H, J 5.0), 3.09 (t, 2H, J 5.0), 3.57 (t, 2H, J 4.0), 3.58 (t, 2H, J4.0), 6.65 (dd, 1H, J 3.0 & 1.5), 7.05 (d, 1H, J 3.0), 7.32 (dd, 1H, J 9.0 & 3.0), 7.42 (d, 1H, J 5.5), 7.71 (d, 1H, J 1.5), 7.82 (s, 1H), 7.94 (d, 1H, J 9.0), 8.03 (d, 1H, J 3.0), 8.47 (d, 1H, J 5.5), 8.58 (s, 1H), 9.87 (s, 1H), 10.15 (s, 1H). HRMS m/z 481.2099 [M+H]$^+$.

1-(4-(6-((4-(6-Methylimidazo[1,2-a]pyridin-3-yl)pyrimidin-2-yl)amino)pyridin-3-yl)piperazin-1-yl)ethan-1-one (13). Prepared by reaction of 1-(5-(4-acetylpiperazin-1-yl)pyridin-2-yl)guanidine 2,2,2-trifluoroacetate (452 mg, 1.20 mmol) with (E)-3-(dimethylamino)-1-(6-methylimidazo[1,2-a]pyridin-3-yl)prop-2-en-1-one (230 mg, 1.00 mmol) using general synthetic procedure I. A yellow solid (149 mg, 35%). $^1$H NMR (DMSO-d$_6$) δ 2.05 (s, 3H), 2.42 (s, 3H), 3.08 (t, 2H, J5.0), 3.15 (t, 2H, J 5.0), 3.59 (t, 2H, J 5.5), 3.60 (t, 2H, J 5.5), 7.35 (dd, 1H, J 9.0 & 1.0), 7.40 (d, 1H, J 5.5), 7.48 (dd, 1H, J 9.5 & 3.0), 7.66 (d, 1H, J 9.0), 8.07 (d, 1H, J 9.0), 8.08 (d, 1H, J 3.0), 8.41 (d, 1H, J 5.5), 8.56 (s, 1H), 9.99 (s, 1H), 10.07 (s, 1H). HRMS m/z 429.2147 [M+H]$^+$.

1-(4-(6-((4-(6-Phenylimidazo[1,2-a]pyridin-3-yl)pyrimidin-2-yl)amino)pyridin-3-yl)piperazin-1-yl)ethan-1-one (14). Prepared by reaction of 10 (247 mg, 501 µmol) with phenylboronic acid (73.2 mg, 600 µmol) using general synthetic procedure J. A yellow solid (198 mg, 80%). $^1$H NMR (DMSO-d$_6$) δ 2.05 (s, 3H), 2.90 (t, 2H, J 5.0), 2.97 (t, 2H, J 4.5), 3.55 (t, 2H, J 5.0), 3.56 (t, 2H, J 5.0), 7.14 (d, 1H, J 7.0), 7.42 (d, 1H, J 5.5), 7.43 (t, 1H, J 6.5), 7.48 (t, 2H, J 6.0), 7.68 (d, 2H, J 6.0), 7.76 (dd, 1H, J 9.0 & 1.5), 7.80-7.88 (m, 3H), 8.47 (d, 1H, J 5.0), 8.59 (s, 1H), 9.96 (s, 1H), 10.19 (s, 1H). HRMS m/z 491.2308 [M+H]$^+$.

1-(4-(6-((4-(6-(Pyridin-3-yl)imidazo[1,2-a]pyridin-3-yl)pyrimidin-2-yl)amino)pyridin-3-yl)piperazin-1-yl)ethan-1-one (15). Prepared by reaction of 10 (247 mg, 501 µmol) with pyridin-3-ylboronic acid (73.8 mg, 600 µmol) using general synthetic procedure J. A yellow solid (198 mg, 80%). ¹H NMR (DMSO-d₆) δ 2.05 (s, 3H), 2.95 (t, 2H, J 5.0), 3.02 (t, 2H, J 4.5), 3.56 (t, 2H, J 5.0), 3.58 (t, 2H, J5.0), 7.23 (d, 1H, J 8.0), 7.44 (d, 1H, J 5.5), 7.52 (dd, 1H, J 8.0 & 5.5), 7.81 (dd, 1H, J 9.0 & 2.0), 7.88 (d, 1H, J 9.0), 7.89 (d, 1H, J 15.5), 7.93 (d, 1H, J 8.5), 8.10 (d, 1H, J 8.0), 8.47 (d, 1H, J 5.5), 8.63 (s, 1H), 8.64 (dd, 1H, J 5.0 & 1.0), 8.96 (dd, 1H, J 12.0), 10.10 (s, 1H), 10.30 (d, 1H, J 7.0). HRMS m/z 492.2257 [M+H]⁺.

1-(4-(6-((4-(6-(Pyrimidin-5-yl)imidazo[1,2-a]pyridin-3-yl)pyrimidin-2-yl)amino)pyridin-3-yl)piperazin-1-yl)ethan-1-one (16). Prepared by reaction of 10 (247 mg, 501 μmol) with 5-(4,4,5,5-tetramethyl-1,3,2-dioxaborolan-2-yl)pyrimidine (124 mg, 602 μmol) using general synthetic procedure J. A yellow solid (200 mg, 81%). ¹H NMR (DMSO-d₆) δ 2.05 (s, 3H), 2.99 (t, 2H, J 5.0), 3.06 (t, 2H, J 5.0), 3.58 (t, 2H, J 4.5), 3.59 (t, 2H, J 4.5), 7.31 (d, 1H, J 7.5), 7.45 (d, 1H, J 5.0), 7.87 (dd, 1H, J 9.5 & 1.5), 7.92 (d, 1H, J 9.5), 7.94 (s, 1H), 8.02 (d, 11H, J 7.5), 8.48 (d, 1H, J 5.5), 8.67 (s, 1H), 9.20 (s, 2H), 9.26 (s, 1H), 10.20 (br s, 1H), 10.40 (s, 1H). HRMS m/z 493.2208 [M+H]⁺.

1-(4-(6-((4-(6-(Thiophen-2-yl)imidazo[1,2-a]pyridin-3-yl)pyrimidin-2-yl)amino)pyridin-3-yl)piperazin-1-yl)ethan-1-one (17). Prepared by reaction of 10 (197 mg, 399 μmol) with thiophen-2-ylboronic acid (61.3 mg, 479 μmol) using general synthetic procedure J. A pale yellow solid (146 mg, 74%). ¹H NMR (DMSO-d₆) δ 2.05 (s, 3H), 2.97 (t, 2H, J 5.0), 3.04 (t, 2H, J 5.0), 3.56 (t, 2H, J 5.0), 3.57 (t, 2H, J 5.0), 7.17 (dd, 1H, J 5.0 & 3.5), 7.25 (dd, 1H, J 9.0 & 3.0), 7.42 (d, 1H, J 5.0), 7.51 (d, 1H, J 3.0), 7.61 (dd, 1H, J 5.0 & 1.0), 7.72 (dd, 1H, J 9.0 & 1.5), 7.81 (dd, 1H, J 9.0 & 0.5), 7.88 (d, 1H, J 9.0), 7.95 (d, 1H, J 2.5), 8.48 (d, 1H, J 5.0), 8.58 (s, 1H), 9.88 (s, 1H), 10.18 (d, 1H, J 0.5). HRMS m/z 497.1874 [M+H]⁺.

1-(4-(6-((4-(6-(2-Aminopyrimidin-5-yl)imidazo[1,2-a]pyridin-3-yl)pyrimidin-2-yl)amino)pyridin-3-yl)piperazin-1-yl)ethan-1-one (18). Prepared by reaction of 10 (197 mg, 399 μmol) with (2-aminopyrimidin-5-yl)boronic acid (66.6 mg, 479 μmol) using general synthetic procedure J. A straw solid (76 mg, 37%). ¹H NMR (DMSO-d₆) δ 2.05 (s, 3H), 2.99 (t, 2H, J 5.0), 3.05 (t, 2H, J 5.0), 3.58 (t, 2H, J 5.0), 3.59 (t, 2H, J 5.0), 6.88 (s, 2H), 7.29 (dd, 1H, J 7.5 & 2.0), 7.42 (d, 1H, J 5.5), 7.72 (dd, 1H, J 9.0 & 1.5), 7.82 (dd, 1H, J 9.5 & 0.5), 7.92 (d, 1H, J 2.5), 7.96 (d, 1H, J 9.0), 8.46 (d, 1H, J 5.5), 8.59 (s, 1H), 8.60 (s, 2H), 10.12 (br s, 1H), 10.19 (s, 1H). HRMS m/z 508.2317 [M+H]⁺.

1-(4-(6-((4-(6-(2-Methoxypyrimidin-5-yl)imidazo[1,2-a]pyridin-3-yl)pyrimidin-2-yl)amino)pyridin-3-yl)piperazin-1-yl)ethan-1-one (19). Prepared by reaction of 10 (197 mg, 399 μmol) with (2-methoxypyrimidin-5-yl)boronic acid (73.8 mg, 479 μmol) using general synthetic procedure J. A yellow solid (190 mg, 91%). ¹H NMR (DMSO-d₆) δ 2.05 (s, 3H), 2.97 (t, 2H, J 4.5), 3.05 (t, 2H, J 4.5), 3.57 (t, 2H, J 5.0), 3.58 (t, 2H, J 5.0), 4.00 (s, 3H), 7.31 (d, 1H, J 8.0), 7.44 (d, 1H, J 5.0), 7.81 (dd, 1H, J 9.0 & 1.5), 7.88 (d, 1H, J 9.0), 7.94 (d, 1H, J 2.5), 8.01 (br d, 1H, J 8.5), 8.47 (d, 1H, J 5.5), 8.65 (s, 1H), 8.97 (s, 2H), 10.17 (br s, 1H), 10.32 (s, 1H). HRMS m/z 523.2311 [M+H]⁺.

1-(4-(6-((4-(6-(2-(4-Methylpiperazin-1-yl)pyrimidin-5-yl)imidazo[1,2-a]pyridin-3-yl)pyrimidin-2-yl)amino)pyridin-3-yl)piperazin-1-yl)ethan-1-one (20). Prepared by reaction of 10 (197 mg, 399 μmol) with 2-(4-methylpiperazin-1-yl)-5-(4,4,5,5-tetramethyl-1,3,2-dioxaborolan-2-yl)pyrimidine (146 mg, 480 μmol) using general synthetic procedure J. A beige solid (198 mg, 84%). ¹H NMR (DMSO-d₆) δ 2.04 (s, 3H), 2.21 (s, 3H), 2.36 (t, 4H, J 5.0), 2.97 (t, 2H, J 4.5), 3.04 (t, 2H, J 4.5), 3.56 (t, 2H, J 5.5), 3.57 (t, 2H, J 5.5), 3.79 (t, 4H, J 5.0), 7.32 (d, 1H, J 7.5), 7.39 (d, 1H, J 5.5), 7.72 (dd, 1H, 19.0 & 1.5), 7.81 (d, 1H, 19.5), 7.94 (d, 1H, J 1.5), 7.99 (d, 1H, J 7.5), 8.44 (d, 1H, J 5.5), 8.58 (s, 1H), 8.71 (s, 2H), 10.14 (br s, 1H), 10.20 (s, 1H). HRMS m/z 591.3052 [M+H]F.

1-(4-(6-((4-(6-(Benzofuran-2-yl)imidazo[1,2-a]pyridin-3-yl)pyrimidin-2-yl)amino)pyridin-3-yl)piperazin-1-yl) ethan-1-one (21). Prepared by reaction of 10 (197 mg, 399 μmol) with 2-(benzofuran-2-yl)-4,4,5,5-tetramethyl-1,3,2-dioxaborolane (117 mg, 479 μmol) using general synthetic procedure J. A yellow solid (166 mg, 78%). ¹H NMR (DMSO-d₆) δ 1.99 (s, 3H), 2.72 (t, 2H, J 5.0), 2.76 (t, 2H, J 5.0), 3.34-3.38 (m, 4H), 7.17 (dd, 1H, J 9.0 & 2.5), 7.27 (td, 1H, J 8.0 & 1.5), 7.32 (td, 1H, J 8.0 & 1.5), 7.38 (d, 1H, J 8.5), 7.44 (d, 1H, J 5.5), 7.49 (s, 1H), 7.68 (d, 1H, J 7.5), 7.89 (dd, 1H, J 9.0 & 1.0), 7.20 (d, 1H, J 9.0), 7.97 (dd, 1H, J 6.5 & 1.5), 7.98 (s, 1H), 8.51 (d, 1H, J 5.5), 8.61 (s, 1H), 9.94 (s, 1H), 10.37 (s, 1H). HRMS m/z 531.2259 [M+H]⁺.

1-(4-(6-((4-(6-(Benzo[b]thiophen-2-yl)imidazo[1,2-a]pyridin-3-yl)pyrimidin-2-yl)amino)pyridin-3-yl)piperazin-1-yl)ethan-1-one (222). Prepared by reaction of 10 (197 mg, 399 μmol) with benzo[b]thiophen-2-ylboronic acid (85.4 mg, 480 μmol) using general synthetic procedure J. A yellow solid (160 mg, 73%). ¹H NMR (DMSO-d₆) δ 1.99 (s, 3H), 2.66 (t, 2H, J 5.0), 2.70 (t, 2H, J 5.0), 3.34-3.38 (m, 4H), 7.14 (dd, 1H, 19.0 & 3.0), 7.35-7.44 (m, 2H), 7.44 (d, 1H, J 5.0), 7.79 (s, 1H), 7.80 (d, 1H, J 8.5), 7.83 (dd, 1H, J 9.0 & 1.5), 7.84 (d, 1H, J 8.0), 7.88 (dd, 1H, J 10.0 & 0.5), 7.89 (d, 1H, J 3.0), 7.96 (d, 1H, J 8.0), 8.50 (d, 1H, J 5.0), 8.61 (s, 1H), 9.89 (s, 1H), 10.30 (s, 1H). HRMS m/z 547.2026 [M+H]⁺.

1-(4-(6-((4-(6-(1H-Pyrrol-3-yl)imidazo[1,2-a]pyridin-3-yl)pyrimidin-2-yl)amino)pyridin-3-yl)piperazin-1-yl)ethan-1-one (23). Prepared by reaction of 10 (197 mg, 399 μmol) with 3-(4,4,5,5-tetramethyl-1,3,2-dioxaborolan-2-yl)-1-(triisopropylsilyl)-1H-pyrrole (168 mg, 481 μmol) at 130° C. for 1 h followed by 160° C. for 1 h using general synthetic procedure J. A yellow solid (150 mg, 79%). ¹H NMR (DMSO-d₆) δ 2.04 (s, 3H), 2.99 (t, 2H, J 5.0), 3.05 (t, 2H, J 5.0), 3.57 (t, 2H, J 4.5), 3.58 (t, 2H, J 4.5), 6.41 (br s, 1H), 6.82 (dd, 1H, J 4.5 & 2.5), 7.28 (dd, 1H, J 9.0 & 3.0), 7.31 (br s, 1H), 7.38 (d, 1H, J 5.5), 7.69 (d, 1H, J 9.0), 7.30 (dd, 1H, J 9.0 & 1.5), 7.93 (d, 1H, J 9.0), 8.00 (d, 1H, J 3.0), 8.43 (d, 1H, J 5.5), 8.48 (s, 1H), 9.85 (s, 1H), 9.94 (s, 1H), 11.03 (br s, 1). HRMS m/z 480.2264 [M+H]⁺.

1-(4-(6-((4-(6-(1H-Pyrazol-4-yl)imidazo[1,2-a]pyridin-3-yl)pyrimidin-2-yl)amino)pyridin-3-yl)piperazin-1-yl) ethan-1-one (24). Prepared by reaction of 10 (197 mg, 399 μmol) with tert-butyl 4-(4,4,5,5-tetramethyl-1,3,2-dioxaborolan-2-yl)-1H-pyrazole-1-carboxylate (141 mg, 479 μmol) using general synthetic procedure J. A beige solid (100 mg, 52%). ¹H NMR (DMSO-d₆) δ 2.05 (s, 3H), 3.02 (t, 2H, J 5.0), 3.08 (t, 2H, J 5.0), 3.58 (t, 2H, 16.0), 3.61 (t, 2H, J 6.5), 7.33 (dd, 1H, J 9.0 & 3.0), 7.41 (d, 1H, J 5.5), 7.77 (s, 1H), 7.78 (s, 1H), 8.00 (d, 1H, J 9.5), 8.01 (d, 1H, J 2.5), 8.19 (br s, 2H), 8.44 (d, 1H, J5.5), 8.56 (s, 1H), 10.06 (s, 1H), 10.10 (s, 1H), 13.08 (br s, 1). HRMS m/z 481.2212 [M+H]⁺.

1-(4-(6-((4-(6-(Furan-3-yl)imidazo[1,2-a]pyridin-3-yl)pyrimidin-2-yl)amino)pyridin-3-yl)piperazin-1-yl)ethan-1-one (25). Prepared by reaction of 10 (148 mg, 300 μmol) with 2-(furan-3-yl)-4,4,5,5-tetramethyl-1,3,2-dioxaborolane (69.9 mg, 360 μmol) using general synthetic procedure J. A brownish solid (75 mg, 52%). ¹H NMR (DMSO-d₆) δ 2.05 (s, 3H), 3.02 (t, 2H, J 5.0), 3.09 (t, 2H, J 5.0), 3.58 (t, 2H, J 5.0), 3.59 (t, 2H, J 5.0), 6.99 (s, 1H), 7.35 (dd, 1H, J 9.0 & 3.0), 7.42 (d, 1H, J 5.5), 7.75 (dd, 1H, J 9.0 & 1.5), 7.79 (d, 1H, J 8.5), 7.80 (t, 1H, J 1.5), 7.96 (d, 1H, J 9.0), 8.02

(d, 1H, J 3.0), 8.29 (s, 1H), 8.45 (d, 1H, J 5.0), 8.57 (s, 1H), 10.00 (s, 1H), 10.06 (s, 1H). HRMS m/z 481.2099 [M+H]+.

1-(4-(6-((4-(6-(Thiophen-3-yl)imidazo[1,2-a]pyridin-3-yl)pyrimidin-2-yl)amino)pyridin-3-yl)piperazin-1-yl)ethan-1-one (26). Prepared by reaction of 10 (148 mg, 300 μmol) with 4,4,5,5-tetramethyl-2-(thiophen-3-yl)-1,3,2-dioxaborolane (75.7 mg, 360 μmol) using general synthetic procedure J. A yellow solid (115 mg, 77%). $^1$H NMR (DMSO-$d_6$) δ 2.05 (s, 3H), 3.00 (t, 2H, J 4.5), 3.06 (t, 2H, J 4.0), 3.50-3.65 (m, 4H), 7.28 (dd, 1H, J 8.5 & 2.0), 7.41 (d, 1H, J 5.0), 7.52 (d, 1H, J 4.0), 7.67 (dd, 1H, J 5.0 & 3.0), 7.80 (d, 1H, J 9.5), 7.85 (d, 1H, J 10.0), 7.92 (d, 1H, J 9.0), 7.95-8.02 (m, 2H), 8.46 (d, 1H, J 5.0), 8.57 (s, 1H), 9.97 (s, 1H), 10.17 (s, 1H). HRMS m/z 497.1864 [M+H]+.

1-(4-(6-((4-(6-(1-Methyl-1H-pyrazol-4-yl)imidazo[1,2-a]pyridin-3-yl)pyrimidin-2-yl)amino)pyridin-3-yl)piperazin-1-yl)ethan-1-one (27). Prepared by reaction of 10 (148 mg, 300 μmol) with 1-methyl-4-(4,4,5,5-tetramethyl-1,3,2-dioxaborolan-2-yl)-1H-pyrazole (74.9 mg, 360 μmol) using general synthetic procedure J. A yellow solid (85 mg, 57%). $^1$H NMR (DMSO-$d_6$) δ 2.05 (s, 3H), 3.01 (t, 2H, J 5.0), 3.08 (t, 2H, J 5.0), 3.58 (t, 2H, J 6.0), 3.61 (t, 2H, J 4.0), 3.88 (s, 3H), 7.33 (dd, 1H, J 9.0 & 2.5), 7.41 (d, 1H, J 5.5), 7.71 (dd, 1H, J 9.5 & 1.5), 7.77 (d, 1H, J 9.5), 7.91 (br s, 1H), 7.96 (d, 1H, J 9.0), 8.01 (d, 1H, J 3.0), 8.17 (br s, 1H), 8.44 (d, 1H, J 5.5), 8.55 (s, 1H), 10.00 (s, 1H), 10.06 (s, 1H). HRMS m/z 495.2361 [M+H]+.

1-(4-(6-((4-(6-(Phenylamino)imidazo[1,2-a]pyridin-3-yl)pyrimidin-2-yl)amino)pyridin-3-yl)piperazin-1-yl)ethan-1-one (28). Prepared by reaction of 10 (395 mg, 801 μmol) with aniline (87.6 μL, 961 μmol) using general synthetic procedure K. A pale yellow solid (128 mg, 32%). $^1$H NMR (DMSO-$d_6$) δ 2.04 (s, 3H), 2.91 (t, 2H, J 5.0), 2.97 (t, 2H, J 5.0), 3.48-3.55 (m, 4H), 6.82 (t, 1H, J 7.0), 7.00 (d, 2H, J 8.0), 7.24 (t, 2H, J 8.0), 7.29 (dd, 1H, J 9.0 & 3.0), 7.39 (d, 1H, J 5.5), 7.42 (dd, 1H, J 9.5 & 2.0), 7.70 (d, 1H, J 9.5), 7.90 (d, 1H, J 9.0), 8.01 (d, 1H, J 3.0), 8.03 (s, 1H), 8.44 (d, 1H, J 5.5), 8.51 (s, 1H), 9.41 (s, 1H), 10.06 (d, 1H, J 2.0). HRMS m/z 506.2418 [M+H]+.

1-(4-(6-((5-Fluoro-4-(imidazo[1,2-a]pyridin-3-yl)pyrimidin-2-yl)amino)pyridin-3-yl)piperazin-1-yl)ethan-1-one (29). Prepared by reaction of 3-(2-chloro-5-fluoropyrimidin-4-yl)imidazo[1,2-a]pyridine (249 mg, 1.00 mmol) with 1-(4-(6-aminopyridin-3-yl)piperazin-1-yl)ethan-1-one (232 mg, 1.05 mmol) using general synthetic procedure K. A pale yellow solid (155 mg, 36%). $^1$H NMR (DMSO-$d_6$) δ 2.05 (s, 3H), 3.09 (t, 2H, J 5.0), 3.15 (t, 2H, J 5.0), 3.60 (t, 2H, J 5.0), 3.61 (t, 2H, J 5.0), 7.18 (td, 1H, J 7.0 & 1.0), 7.48 (dd, 1H, J 9.0 & 3.0), 7.59 (dd, 1H, J 7.0 & 1.0), 7.82 (d, 1H, J 9.0), 7.90 (d, 1H, J 9.0), 8.08 (d, 1H, J 3.0), 8.43 (d, 1H, J 4.0), 8.56 (d, 1H, J 3.5), 10.15 (s, 1H), 10.46 (d, 1H, J7.0). HRMS m/z 433.1895 [M+H]+.

1-(4-(6-((5-Fluoro-4-(6-fluoroimidazo[1,2-a]pyridin-3-yl)pyrimidin-2-yl)amino)pyridin-3-yl)piperazin-1-yl)ethan-1-one (30). Prepared by reaction of 3-(2-chloro-5-fluoropyrimidin-4-yl)-6-fluoroimidazo[1,2-a]pyridine (267 mg, 1.00 mmol) with 1-(4-(6-aminopyridin-3-yl)piperazin-1-yl)ethan-1-one (232 mg, 1.05 mmol) using general synthetic procedure K. A yellow solid (84 mg, 19%). H NMR (DMSO-$d_6$) δ 2.05 (s, 3H), 3.08 (t, 2H, J 5.0), 3.15 (t, 2H, J 4.5), 3.61 (s, 4H), 7.48 (dd, 1H, J 9.0 & 2.5), 7.67 (td, 1H, J 9.5 & 2.0), 7.75 (d, 1H, J 8.5), 7.88 (dd, 1H, J 9.5 & 5.5), 8.10 (d, 1H, J 2.5), 8.46 (d, 1H, J4.0), 8.59 (d, 1H, J 3.5), 10.34 (s, 1H), 10.70 (d, 1H, J 3.5). HRMS m=451.1804 [M+H]+.

1-(4-(6-((5-Fluoro-4-(6-methylimidazo[1,2-a]pyridin-3-yl)pyrimidin-2-yl)amino)pyridin-3-yl)piperazin-1-yl)ethan-1-one (31). Prepared by reaction of 3-(2-chloro-5-fluoropyrimidin-4-yl)-6-methylimidazo[1,2-a]pyridine (263 mg, 1.00 mmol) with 1-(4-(6-aminopyridin-3-yl)piperazin-1-yl)ethan-1-one (232 mg, 1.05 mmol) using general synthetic procedure K. A yellow solid (140 mg, 31%). $^1$H NMR (DMSO-$d_6$) δ 2.05 (s, 3H), 2.43 (s, 3H), 3.08 (t, 2H, J 5.0), 3.15 (t, 2H, J 4.5), 3.59 (t, 2H, J 4.5), 3.60 (t, 2H, J 14.5), 7.44 (d, 1H, J 9.0), 7.48 (dd, 1H, J 9.0 & 2.0), 7.72 (d, 1H, J 9.0), 7.96 (d, 1H, J 9.0), 8.07 (d, 1H, J 2.0), 8.38 (d, 1H, J 4.0), 8.55 (d, 1H, J 3.5), 10.00 (s, 1H), 10.17 (s, 1H). HRMS m/z 447.2054 [M+H]+.

1-(4-(6-((5-Fluoro-4-(6-(trifluoromethyl)imidazo[1,2-a]pyridin-3-yl)pyrimidin-2-yl)amino)pyridin-3-yl)piperazin-1-yl)ethan-1-one (32). Prepared by reaction of 3-(2-chloro-5-fluoropyrimidin-4-yl)-6-(trifluoromethyl)imidazo[1,2-a]pyridine (317 mg, 1.00 mmol) with 1-(4-(6-aminopyridin-3-yl)piperazin-1-yl)ethan-1-one (232 mg, 1.05 mmol) using general synthetic procedure K. A yellow solid (256 mg, 51%). $^1$H NMR (DMSO-$d_6$) δ 2.05 (s, 3H), 3.06 (t, 2H, J 5.0), 3.12 (t, 2H, J 5.0), 3.52-3.64 (m, 4H), 7.40 (dd, 1H, J 9.0 & 3.0), 7.76 (d, 1H, J 9.0), 7.77 (dd, 1H, J 9.5 & 2.0), 8.00 (d, 1H, J 9.0), 8.04 (d, 1H, J 3.0), 8.51 (d, 1H, J 4.0), 8.64 (d, 1H, J 3.5), 10.11 (s, 1H), 10.30 (s, 1H). HRMS m/z 501.1769 [M+H]+.

1-(4-(6-((4-(6-(Benzofuran-3-yl)imidazo[1,2-a]pyridin-3-yl)pyrimidin-2-yl)amino)pyridin-3-yl)piperazin-1-yl)ethan-1-one (33). Prepared by reaction of 10 (198 mg, 401 μmol) with 2-(benzofuran-3-yl)-4,4,5,5-tetramethyl-1,3,2-dioxaborolane (117 mg, 479 μmol) using general synthetic procedure J. An orange solid (185 mg, 87%). $^1$H NMR (DMSO-$d_6$) δ 2.05 (s, 3H), 2.77 (t, 2H, J 5.0), 2.84 (t, 2H, J 5.0), 3.45-3.54 (m, 4H), 7.03 (dd, 1H, 19.0 & 2.5), 7.29 (t, 1H, J 7.5), 7.40 (t, 1H, J 8.0), 7.44 (d, 1H, J 5.0), 7.69 (d, 1H, J 8.5), 7.75 (d, 1H, J 3.0), 7.79 (d, 1H, J 8.5), 7.80 (dd, 1H, J 9.0 & 1.5), 7.81 (d, 1H, J 9.5), 7.89 (d, 1H, J 9.0), 8.43 (s, 1H), 8.48 (d, 1H, J 5.5), 8.62 (s, 1H), 9.75 (s, 1H), 10.34 (s, 1H). HRMS m/z 531.2249 [M+H]+.

1-(4-(6-((4-(6-(1-(Phenylsulfonyl)-1H-indol-3-yl)imidazo[1,2-a]pyridin-3-yl)pyrimidin-2-yl)amino)pyridin-3-yl)piperazin-1-yl)ethan-1-one (34). Prepared by reaction of 10 (494 mg, 1.00 mmol) with 1-(phenylsulfonyl)-3-(4,4,5,5-tetramethyl-1,3,2-dioxaborolan-2-yl)-1H-indole (460 mg, 1.20 mmol) using general synthetic procedure K. A tan solid (441 mg, 66%). $^1$H NMR (DMSO-$d_6$) δ 2.04 (s, 3H), 2.72 (t, 2H, J 5.0), 2.76 (t, 2H, J 5.0), 3.42-3.52 (m, 4H), 6.93 (dd, 1H, J 8.5 & 1.5), 7.29 (t, 1H, J 8.0), 7.42 (d, 1H, J 5.5), 7.43 (t, 1H, J 8.0), 7.56 (t, 2H, J 8.0), 7.67 (t, 1H, J 7.5), 7.69 (d, 1H, J 3.0), 7.76 (d, 1H, J 8.0), 7.78 (dd, 1H, J 9.0 & 1.5), 7.80 (d, 1H, J 9.0), 7.85 (d, 1H, J 9.0), 8.07 (d, 1H, J 8.5), 8.11 (d, 2H, J 7.5), 8.28 (s, 1H), 8.48 (d, 1H, J 5.0), 8.58 (s, 1H), 9.78 (s, 1H), 10.34 (s, 1H). HRMS m/z 670.2343 [M+H]+.

1-(4-(6-((4-(6-(Benzo[b]thiophen-3-yl)imidazo[1,2-a]pyridin-3-yl)pyrimidin-2-yl)amino)pyridin-3-yl)piperazin-1-yl)ethan-1-one (35). Prepared by reaction of 10 (198 mg, 401 μmol) with benzo[b]thiophen-3-ylboronic acid (85.4 mg, 480 μmol) using general synthetic procedure K. A pale yellow solid (185 mg, 84%). $^1$H NMR (DMSO-$d_6$) δ 2.05 (s, 3H), 2.70 (t, 2H, J 5.0), 2.77 (t, 2H, J 5.0), 3.43-3.53 (m, 4H), 6.84 (d, 1H, J 8.5), 7.43 (t, 1H, J 7.5), 7.44 (d, 1H, J 6.0), 7.46 (d, 1H, J 7.0), 7.60 (d, 1H, J 2.5), 7.68 (d, 1H, J 9.0), 7.69 (dd, 1H, J 9.5 & 1.5), 7.88 (d, 2H, J 9.0), 7.97 (s, 1H), 8.12 (d, 1H, J 8.0), 8.47 (d, 1H, J 15.5), 8.63 (s, 1H), 9.75 (s, 1H), 10.30 (s, 1H). HRMS m/z 547.2024 [M+H]+.

1-(4-(6-((4-(6-(1H-Indol-4-yl)imidazo[1,2-a]pyridin-3-yl)pyrimidin-2-yl)amino)pyridin-3-yl)piperazin-1-yl)ethan-1-one (36). Prepared by reaction of 10 (198 mg, 401 μmol)

with 4-(4,4,5,5-tetramethyl-1,3,2-dioxaborolan-2-yl)-1H-indole (117 mg, 481 µmol) using general synthetic procedure K. An off-white solid (120 mg, 57%). $^1$H NMR (DMSO-d$_6$) δ 2.06 (s, 3H), 2.68 (t, 2H, J 5.0), 2.71 (t, 2H, J 5.0), 3.49 (t, 2H, J 5.5), 3.51 (t, 2H, J 4.5), 6.58 (app s, 1H), 6.63 (d, 1H, J 7.0), 7.19 (dd, 1H, J 7.0 & 1.0), 7.22 (t, 1H, J 7.5), 7.41-7.44 (m, 1H), 7.42 (d, 1H, J 5.5), 7.51 (d, 1H, J 7.5), 7.55 (d, 1H, J 2.5), 7.62 (d, 1H, J 9.0), 7.76 (dd, 1H, J 9.5 & 2.0), 7.85 (d, 1H, 19.5), 8.46 (d, 1H, J 5.0), 8.58 (s, 1H), 9.54 (s, 1H), 10.27 (s, 1H), 11.38 (s, 1H). HRMS m/z 530.2426 [M+H]$^+$.

1-(4-(6-((4-(6-(1H-Indol-2-yl)imidazo[1,2-a]pyridin-3-yl)pyrimidin-2-yl)amino)pyridin-3-yl)piperazin-1-yl)ethan-1-one (37). Prepared by reaction of 10 (198 mg, 401 µmol) with 2-(4,4,5,5-tetramethyl-1,3,2-dioxaborolan-2-yl)-1H-indole (117 mg, 481 µmol) using general synthetic procedure K. A yellow solid (140 mg, 66%). $^1$H NMR (DMSO-d$_6$) δ 2.02 (s, 3H), 2.80 (app s, 2H), 2.84 (app s, 2H), 3.43-3.53 (m, 4H), 6.94 (br s, 1H), 7.04 (t, 1H, J 7.5), 7.16 (t, 1H, J 7.5), 7.19 (app br s, 1H), 7.43 (d, 1H, J 8.0), 7.44 (d, 1H, J 5.5), 7.58 (d, 1H, J 8.0), 7.85 (d, 1H, J 9.5), 7.90-7.98 (m, 1H), 7.96 (dd, 1H, J 9.5 & 1.5), 8.00 (d, 1H, J 9.0), 8.49 (d, 1H, J 5.0), 8.59 (s, 1H), 9.91 (s, 1), 10.32 (s, 1H), 11.73 (s, 1H). HRMS m/z 530.2431 [M+H]$^+$.

1-(4-(6-((4-(6-(1-(Phenylsulfonyl)-1H-pyrrolo[2,3-b]pyridin-3-yl)imidazo[1,2-a]pyridin-3-yl)pyrimidin-2-yl)amino)pyridin-3-yl)piperazin-1-yl)ethan-1-one (38). Prepared by reaction of 10 (494 mg, 1.00 mmol) with 1-(phenylsulfonyl)-3-(4,4,5,5-tetramethyl-1,3,2-dioxaborolan-2-yl)-1H-pyrrolo[2,3-b]pyridine (461 mg, 1.20 mmol) using general synthetic procedure K. A pale yellow solid (524 ng, 78%). $^1$H NMR (DMSO-d$_6$) δ 2.04 (s, 3H), 2.66 (t, 2H, 15.0), 2.67 (t, 2H, J 5.0), 3.43 (t, 2H, J 5.5), 3.45 (t, 2H, J 5.0), 6.88 (d, 1H, J 8.5), 7.24 (dd, 1H, J 8.0 & 5.0), 7.40 (d, 1H, J 5.5), 7.60 (t, 2H, J 8.0), 7.61 (d, 1H, J 8.0), 7.69 (d, 1H, J 7.5), 7.71 (dd, 1H, J 10.0 & 2.5), 7.84 (s, 2H), 8.10 (d, 1H, J 8.0), 8.18 (d, 2H, J 7.5), 8.35 (s, 1H), 8.40 (d, 1H, J 5.0), 8.46 (d, 1H, J 5.5), 8.55 (s, 1H), 9.78 (s, 1H), 10.35 (s, 1H4). HRMS m/z 671.2319 [M+H]$^+$.

1-(4-(6-((4-(6-(1-Methyl-1H-indol-2-yl)imidazo[1,2-a]pyridin-3-yl)pyrimidin-2-yl)amino)pyridin-3-yl)piperazin-1-yl)ethan-1-one (39). Prepared by reaction of 10 (198 mg, 401 µmol) with 1-methyl-2-(4,4,5,5-tetramethyl-1,3,2-dioxaborolan-2-yl)-1H-indole (124 mg, 482 µmol) using general synthetic procedure K. A yellow solid (125 mg, 57%). $^1$H NMR (DMSO-d$_6$) δ 2.03 (s, 3H), 2.55 (app s, 4H), 3.76 (s, 3H), 6.76 (s, 1H), 7.05 (d, 1H, J 8.5), 7.10 (t, 1H, J 7.5), 7.23 (t, 1H, J 7.5), 7.45 (d, 1H, J 5.5), 7.52 (d, 2H, J 8.0), 7.62 (d, 1H, J 8.0), 7.69 (d, 2H, J 9.0), 7.87 (d, 1H, J 9.0), 8.47 (d, 1H, J 5.5), 8.65 (d, 1H, J 5.5), 8.65 (s, 11H), 9.94 (s, 1H), 10.45 (s, 1H) (four proton signals (2×CH$_2$) not observed due to overlapping with DMSO residual peak). HRMS m/z 544.2593 [M+H]$^+$.

1-(4-(6-((4-(6-(1-Methyl-1H-indol-3-yl)imidazo[1,2-a]pyridin-3-yl)pyrimidin-2-yl)amino)pyridin-3-yl)piperazin-1-yl)ethan-1-one (40). Prepared by reaction of 10 (198 mg, 401 µmol) with 1-methyl-3-(4,4,5,5-tetramethyl-1,3,2-dioxaborolan-2-yl)-1H-indole (124 mg, 482 µmol) using general synthetic procedure K. A beige solid (166 mg, 76%). $^1$H NMR (DMSO-d$_6$) δ 2.04 (s, 3H), 2.68 (t, 2H, J 5.0), 2.76 (t, 214, J 5.0), 3.44-3.52 (m, 4H), 3.85 (s, 3H), 6.88 (dd, 1H, J 9.0 & 2.5), 7.10 (t, 1H, J 7.5), 7.24 (t, 1H, J 7.5), 7.41 (d, 1H, J 5.5), 7.53 (d, 1H, J 8.0), 7.70-7.73 (m, 1H), 7.72 (s, 1H), 7.75-7.80 (m, 3H), 7.82 (d, 1H, J 9.0), 8.47 (d, 1H, J 5.5), 8.54 (s, 1H), 9.58 (s, 1H), 10.22 (s, 1H). HRMS m/z 544.2587 [M+H]$^+$.

1-(4-(6-((4-(6-(1H-Indol-3-yl)imidazo[1,2-a]pyridin-3-yl)pyrimidin-2-yl)amino)pyridin-3-yl)piperazin-1-yl)ethan-1-one (41). Prepared by deprotection of 38 (335 mg, 500 µmol) according to general synthetic procedure L. A yellow solid (200 mg, 75%). $^1$H NMR (DMSO-d$_6$) δ 2.04 (s, 3H), 2.72 (t, 2H, J 5.0), 2.76 (t, 2H, J 5.0), 3.45 (t, 2H, J 5.0), 3.48 (t, 2H, J 5.0), 6.84 (dd, 1H, J 9.0 & 2.5), 7.08 (t, 1H, J 7.5), 7.18 (t, 1H, J 7.5), 7.41 (d, 1H, J 5.0), 7.49 (d, 1H, J 8.0), 7.70 (d, 1H, J 3.0), 7.78 (d, 1H, J 9.0), 7.78-7.84 (m, 4H), 8.47 (d, 1H, J 5.0), 8.54 (s, 1H), 8.55 (s, 1H), 10.23 (s, 1H), 11.50 (s, 1H). HRMS m/z 530.2410 [M+H]$^+$.

1-(4-(6-((4-(6-(1H-pyrrolo[2,3-b]pyridin-3-yl)imidazo[1,2-a]pyridin-3-yl)pyrimidin-2-yl)amino)pyridin-3-yl)piperazin-1-yl)ethan-1-one (42). Prepared by deprotection of 42 (336 mg, 501 µmol) according to general synthetic procedure L. A yellow solid (186 mg, 70%). $^1$H NMR (DMSO-d$_6$) δ 2.05 (s, 3H), 2.71 (t, 2H, J 5.0), 2.76 (t, 2H, J 5.0), 3.47 (t, 2H, J 5.0), 3.50 (t, 2H, J 5.0), 6.87 (dd, 1H, J 9.0 & 3.0), 7.03 (dd, 1H, J 17.5 & 5.5), 7.42 (d, 1H, J 5.5), 7.67 (d, 1H, J 3.0), 7.75 (d, 1H, J 9.0), 7.81-7.84 (m, 2H), 7.97 (s, 1H), 8.10 (dd, 1H, J 7.5 & 1.5), 8.26 (dd, 1H, J 5.5 & 1.5), 8.47 (d, 1H, J 5.0), 8.55 (s, 1H), 9.70 (s, 1H), 10.27 (s, 1H), 12.01 (br s, 1H). HRMS m/z 531.2367 [M+H]$^+$.

1-(4-(6-((4-(6-Iodoimidazo[1,2-a]pyridin-3-yl)pyrimidin-2-yl)amino)pyridin-3-yl)piperazin-1-yl)ethan-1-one (43). Prepared by reaction of (E)-3-(dimethylamino)-1-(6-iodoimidazo[1,2-a]pyridin-3-yl)prop-2-en-1-one (342 mg, 1.00 mmol) with 1-(5-(4-acetylpiperazin-1-yl)pyridin-2-yl)guanidine 2,2,2-trifluoroacetate (452 mg, 1.20 mmol) using general synthetic procedure I. A yellow solid (305 mg, 56%). $^1$H NMR (DMSO-d$_6$) δ 2.05 (s, 3H), 3.10 (t, 2H, J 5.0), 3.16 (t, 2H, J 5.0), 3.59 (t, 2H, J 5.5), 3.60 (t, 2H, J 5.5), 7.42 (d, 1H, J 5.0), 7.50 (dd, 1H, J 9.0 & 3.0), 7.59 (d, 1H, J 9.5), 7.69 (dd, 1H, J 9.0 & 1.5), 7.89 (d, 1H, J 9.0), 8.13 (d, 1H, J 3.0), 8.45 (d, 1H, J 5.0), 8.55 (s, 1H), 10.05 (s, 1H), 10.24 (s, 1H). HRMS m/z 541.0951 [M+H]$^+$.

1-(4-(6-((4-(Imidazo[1,2-a]pyridin-3-yl)-5-methylpyrimidin-2-yl)amino)pyridin-3-yl)piperazin-1-yl)ethan-1-one (44). Prepared by reaction of 3-(2-chloro-5-methylpyrimidin-4-yl)imidazo[1,2-a]pyridine (245 mg, 1.00 mmol) with 1-(4-(6-aminopyridin-3-yl)piperazin-1-yl)ethan-1-one (232 mg, 1.05 mmol) using general synthetic procedure K. A pale yellow solid (120 mg, 28%). $^1$H NMR (DMSO-d$_6$) δ 2.05 (s, 3H), 2.43 (s, 3H), 3.07 (t, 2H, J 4.5), 3.14 (t, 2H, 14.5), 3.59 (t, 2H, J 4.5), 3.60 (t, 2H, J 4.5), 7.09 (t, 1H, J 7.0), 7.45 (d, 1H, J 9.0 & 2.0), 7.50 (t, 1H, J 8.0), 7.76 (d, 1H, J 9.0), 7.92 (d, 1H, J 9.0), 8.07 (d, 1H, J 2.0), 8.34 (s, 1H), 8.42 (s, 1H), 9.80 (s, 1H), 10.22 (d, 1H, J 7.0). HRMS m/z 429.2149 [M+H]$^+$.

4-(6-Bromoimidazo[1,2-a]pyridin-3-yl)-N-(5-(4-methylpiperazin-1-yl)pyridin-2-yl)pyrimidin-2-amine (45). Prepared by reaction of (E)-1-(6-bromoimidazo[1,2-a]pyridin-3-yl)-3-(dimethylamino)prop-2-en-1-one (295 mg, 1.00 mmol) with 1-(5-(4-methylpiperazin-1-yl)pyridin-2-yl)guanidine (555 mg, 1.20 mmol) using general synthetic procedure I. A yellow solid (294 mg, 63%). $^1$H NMR (DMSO-d$_6$) δ 2.22 (s, 3H), 2.48 (t, 4H, J 4.0), 3.14 (t, 4H, J 4.0), 7.42 (d, 1H, J 5.5), 7.44 (dd, 1H, J 9.0 & 2.5), 7.60 (d, 1H, J 9.5), 7.73 (d, 1H, J 9.5), 7.84 (d, 1H, J 8.5), 8.10 (app s, 1H), 8.45 (d, 1H, J 5.0), 8.63 (s, 1H), 10.10 (s, 1H), 10.29 (s, 1H). HRMS m/z 465.1145 [M($^{79}$Br)+H]$^+$, 467.1125 [M($^{81}$Br)+H]$^+$.

N-(5-(4-Methylpiperazin-1-yl)pyridin-2-yl)-4-(6-phenylimidazo[1,2-a]pyridin-3-yl)pyrimidin-2-amine (46). Prepared by reaction of 45 (186 mg, 400 µmol) with phenylboronic acid (58.5 mg, 480 µmol) using general synthetic procedure J. A yellow solid (126 mg, 68%). $^1$H NMR (DMSO-$d_6$) δ 2.22 (s, 3H), 2.43 (t, 4H, J 4.5), 2.96 (t, 4H, J 5.0), 7.11 (d, 1H, J 8.0), 7.41 (d, 1H, J 5.5), 7.44 (d, 1H, J 7.0), 7.48 (t, 2H, J 7.5), 7.68 (d, 2H, J 7.5), 7.76 (d, 1H, J 9.0), 7.78-7.84 (m, 2H), 7.84 (d, 1H, J 9.5), 8.46 (d, 1H, J 5.5), 8.58 (s, 1H), 9.88 (s, 1H), 10.18 (s, 1H). HRMS m/z 463.2354 [M+H]$^+$.

N-(5-Bromopyridin-2-yl)-4-(imidazo[1,2-a]pyridin-3-yl)pyrimidin-2-amine (47). Prepared by reaction of (A)-3-(dimethylamino)-1-(imidazo[1,2-a]pyridin-3-yl)prop-2-en-1-one (216 mg, 1.00 mmol) with 1-(5-bromopyridin-2-yl)guanidine 2,2,2-trifluoroacetate (395 mg, 1.20 mmol) using general synthetic procedure I. A white solid (225 mg, 61%). $^1$H NMR (DMSO-$d_6$) δ 7.15 (t, 1H, J 7.0), 7.51 (t, 1H, J 8.5), 7.53 (d, 1H, J 5.5), 7.76 (d, 1H, J 9.0), 7.98 (d, 1H, J 9.0), 8.24 (d, 1H, J 9.0), 8.44 (s, 1H), 8.50 (d, 1H, J 5.5), 8.65 (s, 1H), 10.40 (d, 1H, J 7.0), 10.51 (s, 1H). HRMS m/z 367.0308 [M($^{79}$Br)+H]$^+$, 369.0288 [M($^{81}$Br)+H]$^+$.

4-(Imidazo[1,2-a]pyridin-3-yl)-N-(5-(4-(methylsulfonyl)piperazin-1-yl)pyridin-2-yl)pyrimidin-2-amine (48). Prepared by reaction of (E)-3-(dimethylamino)-1-(imidazo[1,2-a]pyridin-3-yl)prop-2-en-1-one (173 mg, 804 µmol) with 1-(5-(4-(methylsulfonyl)piperazin-1-yl)pyridin-2-yl)guanidine 2,2,2-trifluoroacetate (398 mg, 965 µmol) using general synthetic procedure I. A yellow solid (246 mg, 68%). $^1$H NMR (DMSO-$d_6$) δ 2.94 (s, 3H), 3.26 (t, 4H, J 5.0), 3.27 (t, 4H, J 5.0), 7.12 (t, 2H, J 7.0), 7.43 (d, 1H, J 5.5), 7.47-7.53 (m, 1H), 7.76 (d, 1H, J 9.0), 8.05 (d, 1H, J 9.0), 8.10 (s, 11H), 8.44 (d, 1H, J 5.5), 8.63 (s, 1H), 10.06 (s, 1H), 10.40 (d, 1H, J 7.0). HRMS m/z 451.1660 [M+H]$^+$.

1-Ethyl-4-(6-((4-(imidazo[1,2-a]pyridin-3-yl)pyrimidin-2-yl)ammonio)pyridin-3-yl)piperazin-1-ium formate (49). Prepared by reaction of (E)-3-(dimethylamino)-1-(imidazo[1,2-a]pyridin-3-yl)prop-2-en-1-one (173 mg, 804 µmol) with 1-(5-(4-ethylpiperazin-1-yl)pyridin-2-yl)guanidine 2,2,2-trifluoroacetate (459 mg, 964 µmol) using general synthetic procedure I, and purified by flash column chromatography (silica gel, DCM ramping to DCM:CH$_3$OH:32% NH$_3$ in H$_2$O=455:45:1), followed by preparative RP-HPLC (gradient 0% to 25% CH$_3$OH in H$_2$O with 0.1% formic acid over 20 min). A yellow solid (60 mg, 17%). $^1$H NMR (CD$_3$OD) δ 1.32 (t, 3H, J 7.5), 3.01 (q, 2H, J 7.5), 3.18 (t, 4H, J 5.0), 3.39 (t, 4H, J 5.0), 7.11 (t, 1H, J 7.0), 7.35 (d, 1H, J 5.5), 7.52 (ddd, 1H, J 8.5 & 7.0 & 1.0), 7.54 (dd, 1H, J 9.0 & 3.0), 7.70 (d, 1H, J 9.0), 7.97 (d, 1H, J 9.0), 8.06 (d, 1H, J 3.0), 8.41 (d, 1H, J 5.5), 8.42 (s, 1H), 8.44 (s, 1H), 10.12 (d, 1H, J 7.0). HRMS m/z 401.2198 [M−HCOO$^-$]$^+$.

4-(6-Bromoimidazo[1,2-a]pyridin-3-yl)-N-(5-(4-(methylsulfonyl)piperazin-1-yl)pyridin-2-yl)pyrimidin-2-amine (50). Prepared by reaction of (E)-1-(6-bromoimidazo[1,2-a]pyridin-3-yl)-3-(dimethylamino)prop-2-en-1-one (177 mg, 602 µmol) with 1-(5-(4-(methylsulfonyl)piperazin-1-yl)pyridin-2-yl)guanidine 2,2,2-trifluoroacetate (298 mg, 723 µmol) using general synthetic procedure I. A yellow solid (225 mg, 71%). $^1$H NMR (DMSO-$d_6$) δ 2.93 (s, 3H), 3.25 (t, 4H, J 5.0), 3.27 (t, 4H, J 5.0), 7.43 (d, 1H, J 5.5), 7.50 (dd, 1H, J 9.0 & 2.5), 7.61 (d, 1H, J 9.5), 7.73 (d, 1H, J 9.5), 7.89 (br d, 1H, J 9.0), 8.14 (d, 1H, J 2.5), 8.46 (d, 1H, J 5.0), 8.63 (s, 1H), 10.17 (s, 1H), 10.30 (s, 1H). HRMS m/z 529.0764 [M($^{79}$Br)+H]$^+$, 531.0743 [M($^{81}$Br)+H]$^+$.

N-(5-Fluoropyridin-2-yl)-4-(imidazo[1,2-a]pyridin-3-yl)pyrimidin-2-amine (51). Prepared by reaction of (E)-3-(dimethylamino)-1-(imidazo[1,2-a]pyridin-3-yl)prop-2-en-1-one (129 mg, 599 µmol) with 1-(5-fluoropyridin-2-yl)guanidine 2,2,2-trifluoroacetate (193 mg, 720 µmol) using general synthetic procedure I A beige solid (82 mg, 44%). $^1$H NMR (DMSO-$d_6$) δ 7.15 (t, 1H, J 7.0), 7.50 (d, 1H, J 5.5), 7.52 (t, 1H, J 7.5), 7.73 (dd, 1H, J 9.0 & 3.0), 7.76 (d, 1H, J 9.0), 8.24 (dd, 1H, J 9.0 & 4.0), 8.34 (d, 1H, J 3.0), 8.48 (d, 1H, J 5.5), 8.64 (s, 1H), 10.38 (s, 1H), 10.39 (d, 1H, J 7.5). HRMS m/z 307.1104 [M+H]$^+$.

N-(5-Chloropyridin-2-yl)-4-(imidazo[1,2-a]pyridin-3-yl)pyrimidin-2-amine (52). Prepared by reaction of (E)-3-(dimethylamino)-1-(imidazo[1,2-a]pyridin-3-yl)prop-2-en-1-one (130 mg, 604 µmol) with 1-(5-chloropyridin-2-yl)guanidine 2,2,2-trifluoroacetate (205 mg, 720 µmol) using general synthetic procedure I. A white solid (68 mg, 35%). $^1$H NMR (DMSO-$d_6$) δ 7.15 (t, 1H, J 7.0), 7.52 (t, 1H, J 9.0), 7.53 (d, 1H, J 5.5), 7.76 (d, 1H, J 9.0), 7.88 (d, 1H, J 9.0), 8.28 (d, 1H, J 9.0), 8.37 (s, 1H), 8.50 (d, 1H, J 5.5), 8.65 (s, 1H), 10.41 (d, 1H, J 7.0), 10.52 (s, 1H). HRMS m/z 323.0806 [M($^{35}$Cl)+H]$^+$, 325.0778 [M($^{37}$Cl)+H]$^+$.

4-(Imidazo[1,2-a]pyridin-3-yl)-N-(5-iodopyridin-2-yl)pyrimidin-2-amine (53). Prepared by reaction of (E)-3-(dimethylamino)-1-(imidazo[1,2-a]pyridin-3-yl)prop-2-en-1-one (130 mg, 604 µmol) with 1-(5-iodopyridin-2-yl)guanidine 2,2,2-trifluoroacetate (271 mg, 721 µmol) using general synthetic procedure I. A white solid (41 mg, 16%). $^1$H NMR (DMSO-$d_6$) δ 7.14 (t, 1H, J 7.0), 7.52 (t, 1H, J 9.5), 7.53 (d, 1H, J 6.0), 7.76 (d, 1H, J 9.0), 8.08 (d, 1H, J 8.5), 8.16 (d, 1H, J 9.0), 8.50 (d, 1H, J 5.0), 8.54 (s, 1H), 8.66 (s, 1H), 10.42 (d, 1H, J 7.0), 10.49 (s, 1H). HRMS m/z 415.0165 [M+H]$^+$.

N-(5-(4-(Methylsulfonyl)piperazin-1-yl)pyridin-2-yl)-4-(6-phenylimidazo[1,2-a]pyridin-3-yl)pyrimidin-2-amine (54). Prepared by reaction of 54 (159 mg, 300 µmol) with phenylboronic acid (43.9 mg, 360 µmol) using general synthetic procedure J. A yellow solid (140 mg, 89%). $^1$H NMR (DMSO-$d_6$) δ 2.94 (s, 3H), 3.07 (t, 4H, J 4.5), 3.22 (t, 4H, J 4.5), 7.16 (d, 1H, J 8.0), 7.42 (d, 1H, J 5.5), 7.46 (t, 1H, J 7.0), 7.49 (t, 2H, J 7.0), 7.68 (d, 2H, J 7.0), 7.77 (d, 1H, J 9.5), 7.82-7.88 (m, 3H), 8.47 (d, 1H, J 5.0), 8.59 (s, 1H), 9.96 (s, 1H), 10.19 (s, 1H). HRMS m/z 527.1970 [M+H]$^+$.

4-(Imidazo[1,2-a]pyridin-3-yl)-N-(5-methylpyridin-2-yl)pyrimidin-2-amine (55). Prepared by reaction of (E)-3-(dimethylamino)-1-(imidazo[1,2-a]pyridin-3-yl)prop-2-en-1-one (130 mg, 604 µmol) with 1-(5-methylpyridin-2-yl)guanidine 2,2,2-trifluoroacetate (191 mg, 723 µmol) using general synthetic procedure I. A beige solid (70 mg, 38%). $^1$H NMR (DMSO-$d_6$) δ 2.26 (s, 3H), 7.13 (t, 1H, J 7.0), 7.46 (d, 1H, J 5.0), 7.51 (t, 1H, J 8.5), 7.60 (d, 1H, J 8.5), 7.75 (d, 1H, J 9.0), 8.08 (d, 1H, J 8.5), 8.18 (s, 1H), 8.46 (d, 1H, J 5.0), 8.62 (s, 1H), 10.14 (s, 1H), 10.42 (d, 1H, J 6.5). HRMS m/z 303.1361 [M+H]$^+$.

1-(4-(6-((4-(Imidazo[1,2-a]pyridin-3-yl)pyrimidin-2-yl)amino)pyridin-3-yl)piperazin-1-yl)propan-1-one (56). To a suspension of 1 (92 mg, 0.25 mmol) in CHCl$_3$ (10 mL) was added TEA (36 µL, 0.26 mmol). The reaction mixture was cooled on an ice bath, and propionyl chloride (0.22 mL, 2.5 mmol) was added dropwise. The reaction mixture was warmed up and heated at 50° C. overnight, cooled down to room temperature, and concentrated under reduced pressure. The residue was mixed with 32% NH$_3$ in H$_2$O (5 mL), concentrated under reduced pressure, and purified by flash column chromatography (silica gel, DCM ramping to DCM:CH$_3$OH=94:6) to give 61 as a pale yellow solid (60 mg, 57%). $^1$H NMR (DMSO-$d_6$) δ 1.01 (t, 3H, J 7.5), 2.37 (q, 2H, J 7.5), 3.09 (t, 2H, J 5.0), 3.14 (t, 2H, J 5.0), 3.58-3.66 (m, 4H), 7.12 (t, 1H, J 7.0), 7.42 (d, 1H, J 5.5), 7.48 (dd, 1H, J 8.5 & 2.0), 7.51 (t, 1H, J 8.0), 7.75 (d, 1H, J 9.0), 8.03 (d, 1H4, J 9.0), 8.08 (s, 1H4), 8.44 (d, 1H, J 5.5), 8.62 (s, 1H), 10.02 (s, 1H), 10.39 (d, 1H, J 7.0). HRMS m/z 429.2145 [M+H]$^+$.

1-(4-(6-((4-(6-(1H-Pyrazol-3-yl)imidazo[1,2-a]pyridin-3-yl)pyrimidin-2-yl)amino)pyridin-3-yl)piperazin-1-yl)ethan-1-one (57). Prepared by reaction of 10 (198 mg, 401 µmol) with 3-(4,4,5,5-tetramethyl-1,3,2-dioxaborolan-2-yl)-1H-pyrazole (93.1 mg, 480 µmol) using general synthetic procedure J. A pale brown solid (60 mg, 31%). $^1$H NMR (DMSO-d$_6$) δ 2.05 (s, 3H), 3.02 (t, 2H, J 5.0), 3.08 (t, 2H, J 5.0), 3.58 (t, 2H, J 5.0), 3.59 (t, 2H, J 5.0), 6.77 (s, 1H), 7.33 (br s, 1H), 7.43 (d, 1H, J 5.0), 7.81 (app d, 2H, J 9.0), 7.96 (br s, 1H), 8.02 (app s, 2H), 8.47 (d, 1H, J 5.0), 8.58 (s, 1H), 9.88 (br s, 1H), 10.23 (br s, 1H), 13.06 (br s, 1H). HRMS m/z 481.2199 [M+H]$^+$.

1-(4-(6-((4-(6-(1-Methyl-1H-pyrazol-3-yl)imidazo[1,2-a]pyridin-3-yl)pyrimidin-2-yl)amino)pyridin-3-yl)piperazin-1-yl)ethan-1-one (58). Prepared by reaction of 10 (198 mg, 401 µmol) with 1-methyl-3-(4,4,5,5-tetramethyl-1,3,2-dioxaborolan-2-yl)-1H-pyrazole (100 mg, 481 µmol) using general synthetic procedure J. A yellow solid (44 mg, 22%). $^1$H NMR (DMSO-d$_6$) δ 2.06 (s, 3H), 2.99 (t, 2H, J 5.0), 3.06 (t, 2H, J 5.0), 3.59 (app s, 4H), 3.86 (s, 3H), 6.57 (s, 1H), 7.26 (dd, 1H, J 8.0 & 1.0), 7.45 (d, 1H, J 5.5), 7.56 (s, 1H), 7.58 (d, 1H, J 9.5), 7.78 (s, 1H), 7.84 (d, 1H, J 9.0), 7.85 (d, 1H, J 9.0), 8.47 (d, 1H, J 5.5), 8.67 (s, 1H), 10.10 (s, 1H), 10.37 (s, 1H). HRMS m/z 495.2368 [M+H]$^+$.

1-(4-(6-((4-(6-(1-(Difluoromethyl)-1H-pyrazol-4-yl)imidazo[1,2-a]pyridin-3-yl)pyrimidin-2-ylamino)pyridin-3-yl)piperazin-1-yl)ethan-1-one (59). Prepared by reaction of 10 (198 mg, 401 µmol) with 1-(difluoromethyl)-4-(4,4,5,5-tetramethyl-1,3,2-dioxaborolan-2-yl)-1H-pyrazole (117 mg, 479 µmol) using general synthetic procedure J. A yellow solid (156 mg, 73%). $^1$H NMR (DMSO-d$_6$) δ 2.04 (s, 3H), 3.01 (t, 2H, J 5.0), 3.08 (t, 2H, J 5.0), 3.57 (t, 2H, J 5.0), 3.58 (t, 2H, J 5.0), 7.34 (d, 1H, J 9.0), 7.42 (d, 1H, J 5.5), 7.85 (app s, 2H), 7.87 (t, 1H, J 59.0), 7.88-8.02 (m, 2H), 8.32 (s, 1H), 8.45 (d, 1H, J 5.5), 8.58 (s, 1H), 8.85 (s, 1H), 10.08 (s, 1H), 10.19 (s, 1H). HRMS m/z 531.2175 [M+H]$^+$.

Tert-butyl 4-(4-(3-(2-((5-(4-acetylpiperazin-1-yl)pyridin-2-yl)amino)pyrimidin-4-yl)imidazo[1,2-a]pyridin-6-yl)-1H-pyrazol-1-yl)piperidine-1-carboxylate (60). Prepared by reaction of 10 (198 mg, 401 µmol) with tert-butyl 4-(4-(4,4,5,5-tetramethyl-1,3,2-dioxaborolan-2-yl)-1H-pyrazol-1-yl)piperidine-1-carboxylate (181 mg, 480 µmol) using general synthetic procedure J. A yellow solid (116 mg, 44%). $^1$H NMR (DMSO-d$_6$) δ 1.42 (s, 9H), 1.74-1.86 (m, 2H), 2.01-2.06 (m, 2H), 2.05 (s, 3H), 2.94 (app br s, 2H), 3.01 (t, 2H, J 5.0), 3.09 (t, 2H, J 5.0), 3.55-3.60 (m, 4H), 4.06 (d, 2H, J 11.0), 4.32-4.42 (m, 1H), 7.32 (dd, 1H, J 8.5 & 2.0), 7.40 (d, 1H, J 5.5), 7.73 (d, 1H, J 9.5), 7.77 (d, 1H, J 9.5), 7.88 (br s, 1H), 7.96 (d, 1H, J 9.0), 8.01 (d, 1H, J 2.0), 8.34 (s, 1H), 8.44 (d, 1H, J 5.5), 8.54 (s, 1H), 9.98 (s, 1H), 10.06 (s, 1H). HRMS m/z 664.3456 [M+H]$^+$.

1-(4-(6-((4-(6-(5-Methylfuran-2-yl)imidazo[1,2-a]pyridin-3-yl)pyrimidin-2-yl)amino)pyridin-3-yl)piperazin-1-yl)ethan-1-one (61). Prepared by reaction of 10 (198 mg, 401 µmol) with 4,4,5,5-tetramethyl-2-(5-methylfuran-2-yl)-1,3,2-dioxaborolane (100 mg, 481 µmol) using general synthetic procedure J. A yellow solid (140 mg, 71%). $^1$H NMR (DMSO-d$_6$) δ 2.04 (s, 3H), 2.24 (s, 3H), 3.00 (t, 2H, J 5.0), 3.06 (t, 2H, J 4.0), 3.57 (t, 2H, J 5.0), 3.58 (t, 2H, J 5.0), 6.24 (d, 1H, J 2.5), 6.90 (d, 1H, J 2.5), 7.26 (dd, 1H, J 9.0 & 2.5), 7.41 (d, 1H, J 5.0), 7.75 (d, 1H, J 9.5), 7.80 (d, 1H, J 9.5), 7.94 (d, 1H, J 9.0), 8.01 (d, 1H, J 2.5), 8.48 (d, 1H, J 5.0), 8.55 (s, 1H), 9.86 (s, 1H), 10.10 (s, 1H). HRMS m/z 495.2244 [M+H]$^+$.

4-(6-(1-Methyl-1H-pyrazol-4-yl)imidazo[1,2-a]pyridin-3-yl)-N-(5-(4-methylpiperazin-1-yl)pyridin-2-yl)pyrimidin-2-amine (62). Prepared by reaction of 49 (233 mg, 501 µmol) with 1-methyl-4-(4,4,5,5-tetramethyl-1,3,2-dioxaborolan-2-yl)-1H-pyrazole (125 mg, 601 µmol) using general synthetic procedure J. A yellow solid (78 mg, 33%). $^1$H NMR (DMSO-d$_6$) δ 2.24 (s, 3H), 2.48 (t, 4H, J 5.0), 3.06 (t, 4H, J 5.0), 3.89 (s, 3H), 7.29 (d, 1H, J 9.0), 7.40 (d, 1H, J 5.0), 7.70 (d, 1H, J 9.5), 7.77 (d, 1H4, J 9.0), 7.94 (d, 1H, J 9.0), 7.96 (s, 1H), 7.98 (s, 1H), 8.15 (s, 1H), 8.43 (d, 1H, J 5.0), 8.55 (s, 1H), 9.96 (s, 1H), 10.06 (s, 1H). HRMS m/z 467.2416 [M+H]$^+$.

Tert-butyl 4-(3-(2-((5-(4-acetylpiperazin-1-yl)pyridin-2-yl)amino)pyrimidin-4-yl)imidazo[1,2-a]pyridin-6-yl)-3,6-dihydropyridine-1(2H)-carboxylate (63). Prepared by reaction of 10 (198 mg, 401 µmol) with tert-butyl 4-(4,4,5,5-tetramethyl-1,3,2-dioxaborolan-2-yl)-3,6-dihydro pyridine-1(2H)-carboxylate (149 mg, 482 µmol) using general synthetic procedure J. A beige solid (198 mg, 83%). $^1$H NMR (DMSO-d$_6$) δ 1.42 (s, 9H), 2.04 (s, 3H), 2.45 (app s, 2H), 3.06 (t, 2H, J 5.0), 3.13 (t, 2H, J 5.0), 3.52 (t, 2H, J 5.0), 3.58 (t, 2H, J 5.0), 3.59 (t, 2H, J 5.0), 3.99 (app s, 2H), 6.19 (s, 1H), 7.39 (d, 1H, J 5.5), 7.43 (dd, 1H, J 9.0 & 3.0), 7.65 (d, 1H, J 9.5), 7.72 (d, 1H, J 9.5), 7.93 (d, 1H, J 9.0), 8.04 (d, 1H, J 2.5), 8.45 (d, 1H, J 5.0), 8.54 (s, 1H), 9.83 (s, 1H), 9.86 (s, 1H). HRMS m z 596.3094 [M+H]$^+$.

Tert-butyl 6-((4-(imidazo[1,2-a]pyridin-3-yl)pyrimidin-2-vi)amino)-3',6'-dihydro-[3,4'-bipyridine]-1'(2'H)-carboxylate (64). Prepared by reaction of 51 (147 mg, 400 µmol) with tert-butyl 4-(4,4,5,5-tetramethyl-1,3,2-dioxaborolan-2-yl)-3,6-dihydropyridine-1(2H)-carboxylate (149 mg, 482 µmol) using general synthetic procedure J. A pale orange solid (100 mg, 53%). $^1$H NMR (DMSO-d$_6$) δ 1.43 (s, 9H), 3.56 (t, 2H, J 5.0), 4.02 (app s, 2H), 6.20 (s, 1H), 7.14 (t, 1H, J 7.0), 7.51 (d, 1H, J 5.5), 7.52 (td, 1H, J 7.0 & 1.0), 7.77 (d, 1H, J 9.0), 7.87 (dd, 1H, J 8.5 & 2.0), 8.20 (d, 1H, J 9.0), 8.43 (d, 1H, J 2.0), 8.50 (d, 1H, J 5.5), 8.66 (s, 1H), 10.38 (s, 1H), 10.45 (d, 1H, J 7.0) (two proton signals (CH$_2$) not observed due to overlapping with DMSO residual peak). HRMS m/z 470.2298 [M+H]$^+$.

N-(5-(4-Methylpiperazin-1-yl)pyridin-2-yl)-4-(6-(pyridin-3-yl)imidazo[1,2-a]pyridin-3-yl)pyrimidin-2-amine (65). Prepared by reaction of 49 (233 mg, 501 µmol) with pyridin-3-ylboronic acid (73.8 mg, 600 kmol) using general synthetic procedure J. A yellow solid (111 mg, 48%). $^1$H NMR (DMSO-d$_6$) δ 2.23 (s, 3H), 2.45 (t, 4H, J 5.0), 3.00 (t, 4H, J 4.5), 7.20 (d, 1H, J 7.5), 7.42 (d, 1H, J 5.0), 7.52 (dd, 1H, J 7.5 & 5.0), 7.81 (d, 1H, J 9.5), 7.85 (s, 1H), 7.88 (d, 1H, J 9.0), 7.91 (d, 1H, J 9.0), 8.10 (d, 1H, J 7.5), 8.46 (d, 1H, J 5.5), 8.63 (s, 1H), 8.64 (d, 1H, J 7.0), 8.98 (s, 1H), 10.08 (s, 1H), 10.30 (s, 11H). HRMS m/z 464.2306 [M+H].

N-(5-(4-Methylpiperazin-1-yl)pyridin-2-yl)-4-(6-(pyrimidin-5-yl)imidazo[1,2-a]pyridin-3-yl)pyrimidin-2-amine (66). Prepared by reaction of 49 (233 mg, 501 µmol) with 5-(4,4,5,5-tetramethyl-1,3,2-dioxaborolan-2-yl)pyrimidine (124 mg, 602 µmol) using general synthetic procedure J. A yellow solid (175 mg, 75%). $^1$H NMR (DMSO-d$_6$) δ 2.23 (s, 3H), 2.46 (app s, 4H), 3.05 (app s, 4H), 7.29 (d, 1H, J 6.5), 7.45 (d, 1H, J 4.0), 7.88 (d, 1H, J 9.5), 7.90 (s, 1H), 7.93 (d, 1H, J 9.0), 8.01 (d, 1H, J 6.0), 8.48 (d, 1H, J 3.5), 8.68 (s, 1H), 9.21 (s, 2H), 9.27 (s, 1H), 10.18 (br s, 1H), 10.42 (s, 1H). HRMS m/z 465.2263 [M+H]$^+$.

4-(6-(1H-Pyrazol-4-yl)imidazo[1,2-a]pyridin-3-yl)-N-(5-(4-methylpiperazin-1-yl)pyridin-2-yl)pyrimidin-2-amine (67). Prepared by reaction of 49 (233 mg, 501 µmol) with tert-butyl 4-(4,4,5,5-tetramethyl-1,3,2-dioxaborolan-2-yl)-1H-pyrazole-1-carboxylate (177 mg, 601 µmol) using general synthetic procedure J. A yellow solid (80 mg, 35%). $^1$H NMR (DMSO-d$_6$) δ 2.23 (s, 3H), 2.46 (t, 4H, J 5.0), 3.08 (t, 4H, J 5.0), 7.31 (dd, 1H, J 9.0 & 1.5), 7.40 (d, 1H, J 5.5), 7.77 (s, 2H), 7.99 (s, 1H), 8.00 (d, 1H, J 9.0), 8.06 (br s, 1H1), 8.37 (br s, 1H), 8.44 (d, 1H, J 5.5), 8.56 (s, 1H), 10.04 (s, 1H), 10.11 (s, 1H), 13.07 (br s, 1H). HRMS m/z 453.2259 [M+H]+.

N-(5-((4-Ethylpiperazin-1-yl)methyl)pyridin-2-yl)-5-fluoro-4-(6-phenylimidazo[1,2-a]pyridin-3-yl)pyrimidin-2-amine (68). Prepared by reaction of 3-(2-chloro-5-fluoropyrimidin-4-yl)-6-phenylimidazo[1,2-a]pyridine (250 mg, 770 μmol) with 5-((4-ethylpiperazin-1-yl)methyl)pyridin-2-amine (181 mg, 821 μmol) using general synthetic procedure K. A beige solid (163 mg, 42%). $^1$H NMR (DMSO-$d_6$) δ 0.98 (app s, 3H), 2.00-2.50 (m, 10H), 3.27 (s, 2H), 7.39 (d, 1H, J 8.5), 7.42-7.51 (m, 1H), 7.47 (d, 2H, J 7.0), 7.68 (d, 2H, J 6.5), 7.85 (d, 1H, J 8.5), 7.86 (s, 2H), 7.20 (d, 1H, 19.5), 8.45 (d, 1H, J 3.0), 8.67 (s, 1H), 10.27 (s, 1H), 10.36 (s, 11H). HRMS m/z 509.2572 [M+H]+.

N-(5-(4-(Dimethylamino)piperidin-1-yl)pyridin-2-yl)-5-fluoro-4-(6-phenylimidazo[1,2-a]pyridin-3-yl)pyrimidin-2-amine (69). Prepared by reaction of 3-(2-chloro-5-fluoropyrimidin-4-yl)-6-phenylimidazo[1,2-a]pyridine (380 mg, 1.17 mmol) with 5-(4-(dimethylamino)piperidin-1-yl)pyridin-2-amine (381 mg, 1.73 mol) using general synthetic procedure K. A yellow solid (17 mg, 3%). $^1$H NMR (DMSO-$d_6$) δ 1.44 (app q, 2H, J 12.0), 1.80 (d, 2H, J 11.5), 2.10-2.20 (m, 1H), 2.20 (s, 6H), 3.43 (d, 2H, J 11.0), 7.09 (d, 1H, J 9.0), 7.41-7.51 (m, 1H), 7.47 (d, 2H, J 7.5), 7.66 (d, 1H, J 8.5), 7.68 (d, 2H, J 7.0), 7.73 (s, 1H), 7.84 (d, 1H, J 9.0), 7.90 (d, 1H, J 9.5), 8.41 (d, 1H, J 3.5), 8.61 (d, 1H, J 2.0), 9.99 (s, 1H), 10.20 (s, 1H) (two proton signals (CH$_2$) not observed due to overlapping with H$_2$O or DMSO residual peak). HRMS m z 509.2572 [M+H]+.

Example 2 Biological Activity

Kinase Assays

Inhibition of FLT3(WT), FLT3(ITD) and FLT3(D835Y) and CDKs were determined using ADP Glo Kinase assays (Promega Corporation, Madison, WI, USA). For example, FLT3 kinase reaction is performed with buffer (40 nM Tris base pH 7.5, 20 mM MgCl$_2$, 0.4 mM DTT, 0.1 mg/mL BSA), Poly (4:1) Glu, Tyr peptide substrate, $K_m$, ATP for each kinase (FLT3-WT: 200 μM, FLT3-ITD: 100 μM and FLT3-D835Y: 35 μM) and each FLT3 kinase (FLT3-WT: 20 nM, FLT3-ITD: 20 nM and FLT3-D835Y: 5 nM) respectively in a total assay volume of 5 μL. Serial dilutions of 1:3 were prepared for test compounds for 10 concentrations (from 10 μM to 0.5 nM). The kinase reactions are run for an optimised time period (FLT3-WT: 120 min, FLT3-ITD: 80 min, FLT3-D835Y: 100 min) at room temperature and then the reaction was stopped by adding 5 μL of ADP Glo reagent. After incubation at room temperature in the dark for 40 min, 8 μL of kinase detection reagent was added to each well and incubated for 30-40 min. Luminescence was measured using an EnVision Multilabel plate reader (PerkinElmer, Buckinghamshire, UK) with an integration time of 1 see per well. Positive and negative controls were performed in 0.5% DMSO in the presence and absence of each FLT3 kinase, respectively. Similarly, kinase reaction for CDK4/D1 and CDK6/D3 was performed with reaction buffer (40 nM Tris base pH 7.5, 20 mM MgCl$_2$, 0.4 mM DTT), 0.1 mg/ml BSA and RB-CTF substrate (retinoblastoma protein1 C-terminal fraction). For CDK9/CyclinT1, the kinase reaction was performed with the standard assay buffer and Kinase Dilution Buffer and RBER-IRStide substrate. Half-maximal inhibition (IC$_{50}$) values were calculated using a 4-parameter logistic non-linear regression model with Graphpad prism (Version 6.0). Apparent inhibition constants ($K_i$) values were calculated from $K_m$ (ATP) and IC$_{50}$ values for the respective kinases. The results are shown in Table 2.

Proliferation Assay

Compounds from Example 1 were subjected to a standard MTT (3-(4,5-dimethylthiazol-2-yl)-2,5-diphenyltetrazolium bromide) and resazurin assays on solid tumor cell lines and leukemia cell lines, respectively, as previously reported (Wang S et al., *J Med Chem* 47:1662-1675, 2004 and Diab S. et al. *CheMedChem* 9:962-972, 2014). Compound concentrations required to inhibit 50% of cell growth (GI$_{50}$) were calculated using non-linear regression analysis. The results are shown in Table 2.

TABLE 2

Enzymatic and cellular activity of example compounds

| | CDK inhibition $K_i$ (μM) or residual enzymatic activity (%) at 10 μM or 1 μM* | | | | | | FLT3 inhibition $K_i$ (μM) or residual enzymatic activity (%) at 1 μM | | | 72 h Growth inhibition GI$_{50}$ (μM) | |
|---|---|---|---|---|---|---|---|---|---|---|---|
| Cmpd | CDK1B | CDK2E1 | CDK4D1 | CDK6D3 | CDK7HMAT1 | CDK9T1 | WT | ITD | D835Y | MV-4-11 | U937 |
| 1 | 1.335 | 69%* | 0.116 | 0.900 | 1.185 | 0.037 | 0.056 | 0.005 | 0.003 | 0.009 | 0.497 |
| 2 | 1.985 | — | 0.155 | 1.055 | 1.700 | 0.085 | 33% | 0.235 | 0.049 | 0.035 | 0.504 |
| 3 | 3.460 | 49% | 1.975 | >10 | NI | 0.519 | 0.039 | 0.016 | 0.008 | 0.020 | 2.850 |
| 4 | 1.481 | 72%* | 38% | 2.896 | 74% | 28% | 0.077 | 0.021 | 0.028 | 0.038 | 3.357 |
| 5 | 48% | 81%* | 53% | 23% | 84% | 28% | 45% | 0.063 | 0.045 | 0.075 | 6.197 |
| 6 | 50% | 85%* | 48% | 24% | 70% | 1.384 | 0.134 | 0.042 | 0.025 | 0.035 | 11.365 |
| 7 | 0.148 | 0.084 | 0.218 | 0.370 | 43% | 0.041 | 34% | 0.015 | 0.017 | 0.124 | 0.512 |
| 8 | 27% | 59%* | 27% | 40% | 82% | 0.289 | 0.185 | 0.012 | 0.017 | 0.030 | 1.413 |
| 9 | 94% | 64%* | 46% | 32% | 76% | 28% | 0.117 | 0.030 | 0.009 | 0.015 | 0.797 |
| 10 | 41% | 58%* | 34% | 36% | 55% | 23% | 0.083 | 0.006 | 0.010 | 0.002 | 3.127 |
| 11 | 38% | 97%* | 46% | >5 | 60% | 32% | 0.044 | 0.035 | 0.009 | 0.014 | 3.903 |
| 12 | 70% | 67%* | 93% | 42% | 86% | 29% | 0.031 | 0.007 | 0.019 | 0.009 | 0.400 |
| 13 | 2.449 | 52%* | 0.419 | 2.402 | 77% | 0.163 | 0.058 | 0.050 | 0.011 | 0.006 | 1.474 |
| 14 | 94% | 56%* | 69% | 92% | 78% | 0.699 | 0.209 | 0.161 | 0.118 | 0.007 | 0.664 |
| 15 | 64% | 88%* | 77% | 91% | 65% | 0.680 | 0.187 | 0.111 | 0.042 | 0.005 | 1.479 |
| 16 | 81% | 90%* | 78% | 99% | 60% | 0.762 | 23% | 0.426 | 0.048 | 0.018 | 2.921 |
| 17 | >0.5 | 52%* | 0.340 | 76% | 0.148 | 0.427 | 0.109 | 0.007 | 0.027 | 0.002 | 0.690 |
| 18 | 69% | 97%* | 48% | 100% | 99% | 0.318 | 0.592 | 0.333 | 0.054 | 0.023 | 8.700 |
| 19 | 96% | 82%* | 53% | 65% | 54% | 33% | 0.360 | 0.189 | 0.032 | 0.017 | 6.709 |
| 20 | 100% | 83%* | 70% | 77% | 66% | 38% | 36% | 0.127 | 0.058 | 0.060 | 4.037 |
| 21 | 95% | 86%* | 78% | 102% | 97% | >5 | 0.060 | 0.083 | 0.003 | 0.017 | 4.560 |

TABLE 2-continued

Enzymatic and cellular activity of example compounds

| | CDK inhibition $K_i$ (μM) or residual enzymatic activity (%) at 10 μM or 1 μM* | | | | | | FLT3 inhibition $K_i$ (μM) or residual enzymatic activity (%) at 1 μM | | | 72 h Growth inhibition $GI_{50}$ (μM) | |
|---|---|---|---|---|---|---|---|---|---|---|---|
| Cmpd | CDK1B | CDK2E1 | CDK4D1 | CDK6D3 | CDK7HMAT1 | CDK9T1 | WT | ITD | D835Y | MV-4-11 | U937 |
| 22 | 100% | 83%* | 64% | 102% | 106% | >5 | 0.828 | 0.026 | 0.092 | 0.002 | >10 |
| 23 | 59% | 76%* | 50% | 71% | 55% | 0.421 | 0.031 | 0.007 | 0.012 | 0.001 | 0.323 |
| 24 | 35% | 24%* | 66% | 61% | 1.185 | 0.125 | 0.037 | 0.018 | 0.003 | 0.025 | 0.466 |
| 25 | 95%* | 40%* | 75%* | 52%* | 0.186 | 0.071 | 0.047 | 0.016 | 0.025 | 0.005 | 0.765 |
| 26 | 95%* | 73%* | 73%* | 73%* | 83%* | 36%* | 0.101 | 0.029 | 0.085 | 0.004 | 0.538 |
| 27 | 88%* | 89%* | 70%* | 70%* | 93%* | 31%* | 0.009 | 0.006 | 0.002 | 0.002 | 0.883 |
| 28 | 98%* | 86%* | 77%* | 80%* | 91%* | 61%* | 0.087 | 0.025 | 0.009 | 0.006 | 1.493 |
| 29 | 100%* | 47%* | 59%* | 59%* | 82%* | 36%* | >0.5 | 0.196 | 0.216 | 0.043 | 0.393 |
| 30 | 96%* | 51%* | 55%* | 58%* | 77%* | 33%* | 0.202 | 0.178 | 0.066 | 0.072 | 4.040 |
| 31 | 50%* | 0.301 | 37%* | 38%* | — | 0.308 | 0.093 | 0.060 | 0.019 | 0.005 | 19.140 |
| 32 | 93%* | 65%* | 67%* | 70%* | 84%* | 82%* | 0.330 | 0.254 | 0.100 | 0.024 | 0.821 |
| 33 | 98%* | 84%* | 60%* | 79%* | 88%* | 72%* | 0.214 | 0.187 | 0.383 | 0.003 | 1.857 |
| 34 | 99%* | 75%* | 55%* | 77%* | 80%* | 100%* | >0.5 | 0.237 | 0.559 | 0.066 | 2.492 |
| 35 | 81%* | 100%* | 77%* | 76%* | 81%* | 91%* | >0.5 | >0.5 | >0.5 | 0.007 | >10 |
| 36 | 96%* | 89%* | 58%* | 76%* | 96%* | 99%* | >0.5 | 25% | >0.5 | 0.012 | 1.360 |
| 37 | 96%* | 91%* | 78%* | 78%* | 103%* | 39%* | >0.5 | 0.998 | >0.5 | 0.010 | 2.420 |
| 38 | 99%* | 82%* | 70%* | 70%* | 102%* | 85%* | >0.5 | 0.056 | 0.243 | 0.044 | 2.908 |
| 39 | 101%* | 92%* | 95%* | 85%* | — | 69%* | >0.5 | 0.018 | >0.5 | 0.038 | >10 |
| 40 | 97%* | 93%* | 55%* | 78%* | 104%* | 82%* | 0.441 | 0.574 | 0.398 | 0.001 | 1.337 |
| 41 | 98%* | 81%* | 54%* | 89%* | 79%* | 42%* | 0.490 | 0.034 | 0.417 | 0.001 | 1.285 |
| 42 | 95%* | 46%* | 52%* | 64%* | 80%* | 0.607 | 0.002 | 0.014 | 0.003 | 0.005 | 1.564 |
| 43 | 92%* | 75%* | 70%* | 70%* | 75%* | 0.475 | 0.038 | 0.044 | 0.018 | 0.006 | 3.573 |
| 44 | 91%* | 66%* | 63%* | 68%* | — | 93%* | >0.5 | 0.167 | 0.362 | 0.387 | >10 |
| 45 | 71%* | 49%* | 34%* | 46%* | — | 0.111 | 0.025 | 0.015 | 0.013 | 0.023 | 1.958 |
| 46 | 87%* | 86%* | 63%* | 86%* | — | 0.083 | 0.016 | 0.005 | 0.008 | 0.007 | 2.399 |
| 47 | 79%* | 103%* | 72%* | 85%* | — | 62% | >0.5 | 0.489 | >0.5 | 0.545 | 0.645 |
| 48 | 90%* | 73%* | 76%* | 71%* | — | 43%* | 0.161 | 0.049 | 0.052 | 0.048 | 1.880 |
| 49 | — | — | — | — | — | — | — | 0.030 | — | 0.017 | 0.121 |
| 50 | 62%* | 74%* | 40%* | 63%* | 57%* | 48%* | 0.035 | 0.180 | 0.015 | 0.007 | 0.127 |
| 51 | — | 0.116 | — | — | — | — | 0.169 | 0.250 | 0.052 | 0.072 | 0.350 |
| 52 | — | 52%* | — | — | — | — | >0.5 | 0.421 | 0.584 | 0.213 | 0.691 |
| 53 | — | 99%* | — | — | — | — | >0.5 | >0.5 | >0.5 | 0.382 | 2.503 |
| 54 | — | — | — | — | — | 52%* | 0.004 | 0.400 | 0.003 | 0.009 | 4.330 |
| 55 | — | — | — | — | — | — | — | 0.044 | — | 0.049 | 0.471 |
| 56 | — | — | — | — | — | — | — | 0.016 | — | 0.022 | 0.339 |
| 57 | — | — | — | — | — | — | — | 0.006 | — | 0.004 | 0.728 |
| 58 | — | — | — | — | — | — | — | 0.049 | — | 0.009 | 0.206 |
| 59 | — | — | — | — | — | — | — | 0.018 | — | 0.008 | 0.462 |
| 60 | — | — | — | — | — | — | — | 0.084 | — | 0.019 | 0.243 |
| 61 | — | — | — | — | — | — | — | 0.004 | — | <0.0001 | 0.199 |
| 62 | — | — | — | — | — | — | — | 0.029 | — | 0.006 | 0.773 |
| 63 | — | — | — | — | — | — | — | 0.132 | — | 0.035 | 0.436 |
| 64 | — | — | — | — | — | — | — | 0.308 | — | 0.152 | 0.367 |
| 65 | — | 94%* | — | — | — | 0.140 | — | 0.030 | — | 0.032 | 0.382 |
| 66 | — | 80%* | — | — | — | 0.345 | — | 0.116 | — | 0.174 | 1.090 |
| 67 | — | 0.197 | — | — | — | 0.041 | — | 0.011 | — | 0.017 | 0.018 |
| 68 | — | — | — | — | — | — | — | 0.070 | — | 0.117 | 0.600 |
| 69 | — | — | — | — | — | — | — | 0.016 | — | 0.018 | 0.946 |

(—) not tested

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgment of any form of suggestion that such prior art forms part of the common general knowledge.

It will be appreciated by those skilled in the art that the present disclosure is not restricted in its use to the particular application described. Neither is the present disclosure restricted in its preferred embodiment with regard to the particular elements and/or features described or depicted herein. It will be also appreciated that the disclosure is not limited to the embodiment or embodiments disclosed, but is capable of numerous rearrangements, modifications and substitutions without departing from the scope of the disclosure as set forth and defined by the following claims.

The invention claimed is:

1. A compound of formula I:

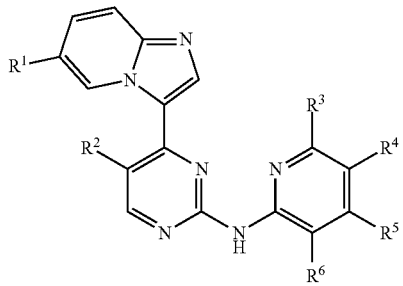

wherein:

$R^1$, $R^2$, $R^3$, $R^5$ and $R^6$ are each independently selected from the group consisting of H, alkyl, aryl, aralkyl, alicyclic, heteroaryl, heterocyclic, halogen, $NO_2$, CN, $CF_3$, OH, O-alkyl, O-aryl, $NH_2$, NH-alkyl, NH-aryl, N-(alkyl)$_2$, N-(aryl)$_2$, N-(alkyl)(aryl), NH-alkyl-N(alkyl)$_2$, COOH, $CONH_2$, CONH-alkyl, CONH-aryl, SH-alkyl, $SO_3H$, $SO_2$-alkyl, $SO_2$-aryl, $SO_2NH_2$, CO-alkyl, CO-aryl, wherein said alkyl, aryl, aralkyl, alicyclic and heterocyclic groups may be optionally substituted with one or more groups selected from halogen, CN, OH, alkyl, O—$C_{1-6}$ alkyl, amino, COOH, $CONH_2$, $CF_3$, $CH(F)_2$ or a heterocyclic group optionally substituted with $C_{1-6}$ alkyl, $CH(F)_2$, COO—$C_{1-6}$ alkyl, or phenylsulfonyl;

$R^4$ is selected from the following:

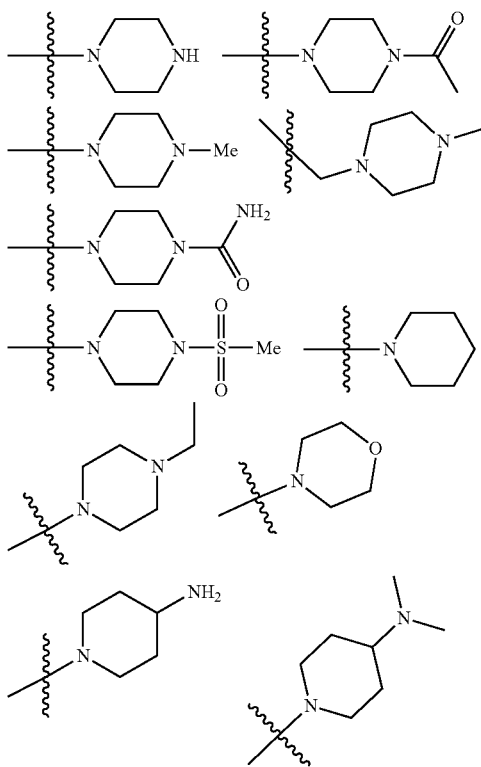
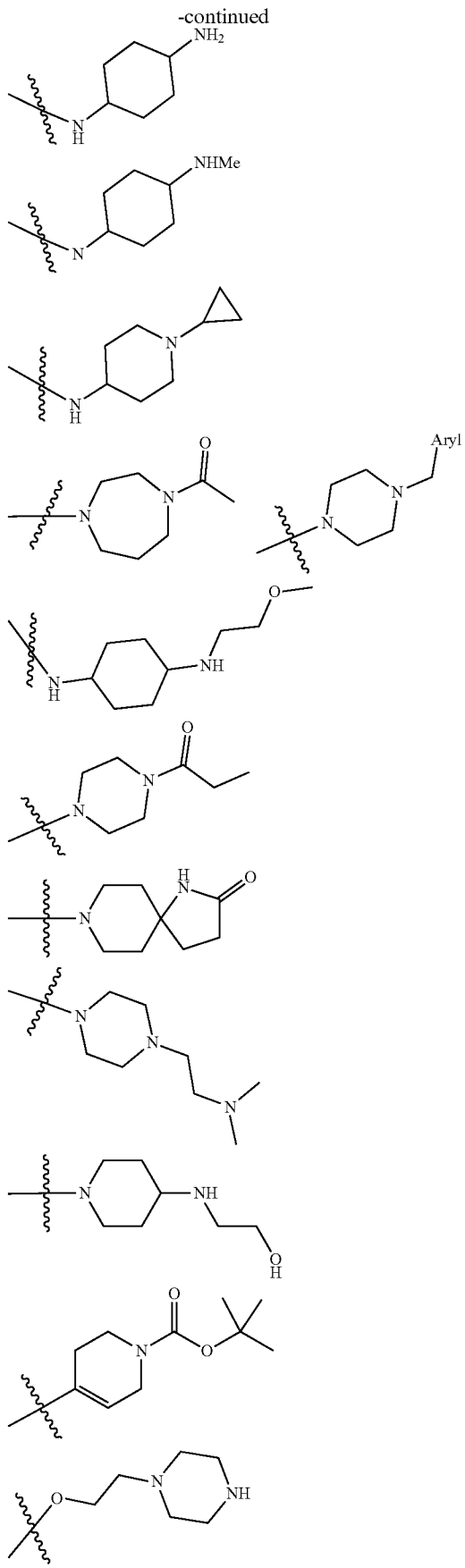

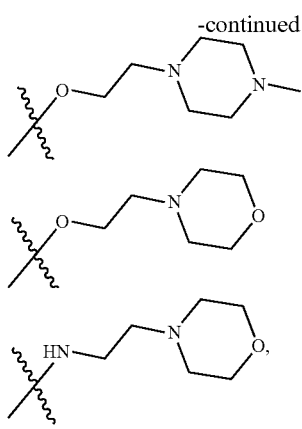

optionally further comprising an alkyl, amino, alkoxy, or ketone bridge to the pyridine group;

or a pharmaceutically acceptable salt or solvate thereof.

2. A compound according to claim 1, wherein $R^1$ is H, alkyl, aryl, CN, $CF_3$, $NH_2$, heterocyclic, O-alkyl, NH-alkyl, NH-alkyl-N(alkyl)$_2$, NH-aryl, N-(alkyl)$_2$, N-(alkyl) (aryl), SH-alkyl, or halogen.

3. A compound according to claim 2, wherein $R^1$ is H, $C_{1-3}$ alkyl, aryl, $CF_3$, or halogen.

4. A compound according to claim 1, wherein $R^1$ is a heteroaryl or heterocyclic group optionally substituted with $C_{1-6}$ alkyl, O—$C_{1-6}$ alkyl, amino, $CH(F)_2$, phenylsulfonyl, or piperazine optionally substituted with $C_{1-6}$ alkyl.

5. A compound according to claim 4, wherein $R^1$ is selected from piperazine optionally substituted with a $C_{1-6}$ alkyl, pyridine optionally substituted with a $C_{1-6}$ alkyl, pyrimidine optionally substituted with $C_{1-6}$ alkyl, O-methyl, $NH_2$ or a piperazine, pyrrole or pyrazole optionally substituted with $C_{1-6}$ alkyl or $CH(F)_2$, piperazine optionally substituted with COO—$C_{1-6}$ alkyl, thiophenyl, furan optionally substituted with a $C_{1-6}$ alkyl, benzofuran, benzo-thiophenyl, indole optionally substituted with $C_{1-6}$ alkyl or phenylsulfonyl, and pyrrolopyridine optionally substituted with phenylsulfonyl.

6. A compound according to claim 1, wherein $R^2$ is H, alkyl, CN or halogen.

7. A compound according to claim 1, wherein at least one of $R^3$, $R^4$, $R^5$ and $R^6$ is $C_{1-6}$ alkyl or halogen.

8. A compound of formula II:

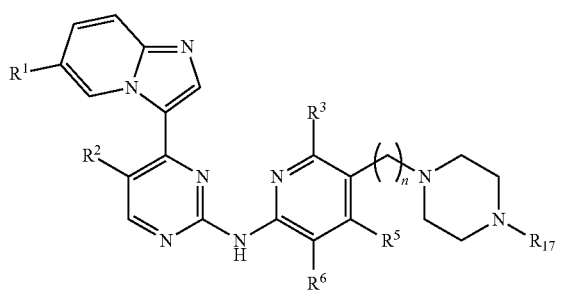

wherein n is 0 or 1, and $R^1$, $R^2$, $R^3$, $R^5$ and $R^6$ are as defined in respect of Formula I in claim 1; and $R^{17}$ is selected from H, alkyl, alkoxy, carbonyl and carboxamide.

9. A compound selected from the group consisting of:
1-(4-(6-((4-(imidazo[1,2-a]pyridin-3-yl)pyrimidin-2-yl) amino)pyridin-3-yl)piperazin-1-yl)ethan-1-one;
1-(4-(6-((4-(6-(thiophen-2-yl)imidazo[1,2-a]pyridin-3-yl)pyrimidin-2-yl)amino)pyridin-3-yl)piperazin-1-yl) ethan-1-one;
1-(4-(6-((5-fluoro-4-(6-methylimidazo[1,2-a]pyridin-3-yl)pyrimidin-2-yl)amino)pyridin-3-yl)piperazin-1-yl) ethan-1-one;
N-(5-((4-ethylpiperazin-1-yl)methyl)pyridin-2-yl)-5-fluoro-4-(6-phenylimidazo[1,2-a]pyridin-3-yl)pyrimidin-2-amine;
N-(5-(4-(dimethylamino)piperidin-1-yl)pyridin-2-yl)-5-fluoro-4-(6-phenylimidazo[1,2-a]pyridin-3-yl)pyrimidin-2-amine;
1-(4-(6-((4-(6-chloroimidazo[1,2-a]pyridin-3-yl)pyrimidin-2-yl)amino)pyridin-3-yl)piperazin-1-yl)ethan-1-one;
1-(4-(6-((4-(6-(trifluoromethyl)imidazo[1,2-a]pyridin-3-yl)pyrimidin-2-yl)amino)pyridin-3-yl)piperazin-1-yl) ethan-1-one;
1-(4-(6-((4-(6-methylimidazo[1,2-a]pyridin-3-yl)pyrimidin-2-yl)amino)pyridin-3-yl)piperazin-1-yl)ethan-1-one;
1-(4-(6-((4-(6-phenylimidazo[1,2-a]pyridin-3-yl)pyrimidin-2-yl)amino)pyridin-3-yl)piperazin-1-yl)ethan-1-one;
1-(4-(6-((4-(6-(pyridin-3-yl)imidazo[1,2-a]pyridin-3-yl) pyrimidin-2-yl)amino)pyridin-3-yl)piperazin-1-yl) ethan-1-one;
1-(4-(6-((4-(6-(benzofuran-2-yl)imidazo[1,2-a]pyridin-3-yl)pyrimidin-2-yl)amino)pyridin-3-yl)piperazin-1-yl) ethan-1-one;
1-(4-(6-((4-(6-(benzo[b]thiophen-2-yl)imidazo[1,2-a] pyridin-3-yl)pyrimidin-2-yl)amino)pyridin-3-yl)piperazin-1-yl)ethan-1-one;
1-(4-(6-((4-(6-(1H-pyrrol-3-yl)imidazo[1,2-a]pyridin-3-yl)pyrimidin-2-yl)amino)pyridin-3-yl)piperazin-1-yl) ethan-1-one;
1-(4-(6-((4-(6-(1H-pyrazol-4-yl)imidazo[1,2-a]pyridin-3-yl)pyrimidin-2-yl)amino)pyridin-3-yl)piperazin-1-yl) ethan-1-one;
1-(4-(6-((4-(6-(furan-3-yl)imidazo[1,2-a]pyridin-3-yl)pyrimidin-2-yl)amino)pyridin-3-yl)piperazin-1-yl)ethan-1-one;
1-(4-(6-((4-(6-(thiophen-3-yl)imidazo[1,2-a]pyridin-3-yl)pyrimidin-2-yl)amino)pyridin-3-yl)piperazin-1-yl) ethan-1-one;
1-(4-(6-((4-(6-(1-methyl-1H-pyrazol-4-yl)imidazo[1,2-a] pyridin-3-yl)pyrimidin-2-yl)amino)pyridin-3-yl)piperazin-1-yl)ethan-1-one;
1-(4-(6-((4-(6-(phenylamino) imidazo[1,2-a]pyridin-3-yl) pyrimidin-2-yl)amino)pyridin-3-yl)piperazin-1-yl) ethan-1-one;
1-(4-(6-((4-(6-(benzofuran-3-yl)imidazo[1,2-a]pyridin-3-yl)pyrimidin-2-yl)amino)pyridin-3-yl)piperazin-1-yl) ethan-1-one;
1-(4-(6-((4-(6-(benzo[b]thiophen-3-yl)imidazo[1,2-a] pyridin-3-yl)pyrimidin-2-yl)amino)pyridin-3-yl)piperazin-1-yl)ethan-1-one;
1-(4-(6-((4-(6-(1-methyl-1H-indol-3-yl)imidazo[1,2-a] pyridin-3-yl)pyrimidin-2-yl)amino)pyridin-3-yl)piperazin-1-yl)ethan-1-one;
1-(4-(6-((4-(6-(1H-indol-3-yl)imidazo[1,2-a]pyridin-3-yl)pyrimidin-2-yl)amino)pyridin-3-yl)piperazin-1-yl) ethan-1-one;

1-(4-(6-((4-(6-(1H-pyrrolo[2,3-b]pyridin-3-yl)imidazo[1,2-a]pyridin-3-yl)pyrimidin-2-yl)amino)pyridin-3-yl)piperazin-1-yl)ethan-1-one;

1-(4-(6-((4-(6-iodoimidazo[1,2-a]pyridin-3-yl)pyrimidin-2-yl)amino)pyridin-3-yl)piperazin-1-yl)ethan-1-one;

N-(5-(4-methylpiperazin-1-yl)pyridin-2-yl)-4-(6-phenylimidazo[1,2-a]pyridin-3-yl)pyrimidin-2-amine;

4-(6-bromoimidazo[1,2-a]pyridin-3-yl)-N-(5-(4-(methylsulfonyl)piperazin-1-yl)pyridin-2-yl)pyrimidin-2-amine;

N-(5-(4-(methylsulfonyl)piperazin-1-yl)pyridin-2-yl)-4-(6-phenylimidazo[1,2-a]pyridin-3-yl)pyrimidin-2-amine;

1-(4-(6-((4-(6-(1H-pyrazol-3-yl)imidazo[1,2-a]pyridin-3-yl)pyrimidin-2-yl)amino)pyridin-3-yl)piperazin-1-yl)ethan-1-one;

1-(4-(6-((4-(6-(1-methyl-1H-pyrazol-3-yl)imidazo[1,2-a]pyridin-3-yl)pyrimidin-2-yl)amino)pyridin-3-yl)piperazin-1-yl)ethan-1-one;

1-(4-(6-((4-(6-(1-(difluoromethyl)-1H-pyrazol-4-yl)imidazo[1,2-a]pyridin-3-yl)pyrimidin-2-yl)amino)pyridin-3-yl)piperazin-1-yl)ethan-1-one;

1 tert-butyl 4-(4-(3-(2-((5-(4-acetylpiperazin-1-yl)pyridin-2-yl)amino)pyrimidin-4-yl)imidazo[1,2-a]pyridin-6-yl)-1H-pyrazol-1-yl)piperidine-1-carboxylate;

1-(4-(6-((4-(6-(5-methylfuran-2-yl)imidazo[1,2-a]pyridin-3-yl)pyrimidin-2-yl)amino)pyridin-3-yl)piperazin-1-yl)ethan-1-one; and 4-(6-(1-methyl-1H-pyrazol-4-yl)imidazo[1,2-a]pyridin-3-yl)-N-(5-(4-methylpiperazin-1-yl)pyridin-2-yl)pyrimidin-2-amine.

10. A pharmaceutical composition or medicament comprising the compound of claim 1 or a pharmaceutically acceptable salt or solvate thereof, and a pharmaceutically acceptable carrier, diluent and/or excipient.

11. A method for modulating protein kinase activity in a cell, comprising introducing to or contacting said cell with an effective amount of the compound of claim 1 or a pharmaceutically acceptable salt or solvate thereof.

12. A method of treating cancer or another proliferative cell disease or condition in a subject, the method comprising administering to said subject a therapeutically effective amount of the compound of claim 1 or a pharmaceutically acceptable salt or solvate, optionally in combination with a pharmaceutically acceptable carrier, diluent and/or excipient, wherein the cancer or proliferative cell disease or condition to be treated is selected from those characterised by over-expression and mutations of FLT3.

13. A pharmaceutical composition or medicament comprising the compound of claim 9 or a pharmaceutically acceptable salt or solvate thereof, and a pharmaceutically acceptable carrier, diluent and/or excipient.

14. A method for modulating protein kinase activity in a cell, comprising introducing to or contacting said cell with an effective amount of the compound of claim 9 or a pharmaceutically acceptable salt or solvate thereof.

15. A method of treating cancer or another proliferative cell disease or condition in a subject, the method comprising administering to said subject a therapeutically effective amount of the compound of claim 9 or a pharmaceutically acceptable salt or solvate thereof, optionally in combination with a pharmaceutically acceptable carrier, diluent and/or excipient, wherein the cancer or proliferative cell disease or condition to be treated is selected from those characterised by over-expression and mutations of FLT3.

* * * * *